US009518276B2

(12) United States Patent
Koivuranta et al.

(10) Patent No.: US 9,518,276 B2
(45) Date of Patent: Dec. 13, 2016

(54) GENETICALLY MODIFIED FUNGI AND THEIR USE IN LIPID PRODUCTION

(75) Inventors: Kari Koivuranta, Espoo (FI); Laura Ruohonen, Espoo (FI); Merja Penttilä, Espoo (FI)

(73) Assignee: TEKNOLOGIAN TUTKIMUSKESKUS VTT, Vtt (FI)

( * ) Notice: Subject to any disclaimer, the term of this patent is extended or adjusted under 35 U.S.C. 154(b) by 349 days.

(21) Appl. No.: 13/806,281

(22) PCT Filed: Jun. 21, 2011

(86) PCT No.: PCT/FI2011/050594
§ 371 (c)(1),
(2), (4) Date: Dec. 21, 2012

(87) PCT Pub. No.: WO2011/161317
PCT Pub. Date: Dec. 29, 2011

(65) Prior Publication Data
US 2013/0102042 A1   Apr. 25, 2013

(30) Foreign Application Priority Data

Jun. 24, 2010   (FI) .................................... 20105733

(51) Int. Cl.
| | | |
|---|---|---|
| C12P 7/04 | (2006.01) | |
| C12P 7/64 | (2006.01) | |
| C12N 9/02 | (2006.01) | |
| C12N 9/10 | (2006.01) | |
| C12N 9/88 | (2006.01) | |
| C12N 9/00 | (2006.01) | |
| C12N 15/80 | (2006.01) | |

(52) U.S. Cl.
CPC ........... *C12P 7/6463* (2013.01); *C12N 9/0008* (2013.01); *C12N 9/1029* (2013.01); *C12N 9/88* (2013.01); *C12N 9/93* (2013.01); *C12N 15/80* (2013.01); *C12P 7/649* (2013.01); *C12Y 102/0101* (2013.01); *C12Y 401/01001* (2013.01); *Y02E 50/13* (2013.01); *Y02P 20/52* (2015.11)

(58) Field of Classification Search
CPC ........ C12N 9/0008; C12N 9/0036; C12P 7/04; C12P 7/16; Y02E 50/10; C07C 67/32; C12Y 203/01009
See application file for complete search history.

(56) References Cited

FOREIGN PATENT DOCUMENTS

| CN | 101892092 A | 11/2010 |
|---|---|---|
| DE | 102004052115 A1 | 4/2006 |
| WO | WO 00/00619 A2 | 1/2000 |
| WO | WO 00/60095 A2 | 10/2000 |
| WO | WO 2005/003322 A2 | 1/2005 |
| WO | WO 2007/136762 A2 | 11/2007 |
| WO | WO 2008/080124 A2 | 7/2008 |
| WO | WO 2008/130372 A2 | 10/2008 |
| WO | WO 2008/151149 A2 | 12/2008 |
| WO | WO 2009/124070 A1 | 10/2009 |
| WO | WO 2009/126890 A2 | 10/2009 |
| WO | WO 2010/068921 A2 | 6/2010 |
| WO | WO 2011/044279 A2 | 4/2011 |

OTHER PUBLICATIONS

Altschul et al., "Gapped BLAST and PSI-BLAST: a new generation of protein database search programs," Nucleic Acids Research, vol. 25, No. 17, 1997, pp. 3389-3402.
Boulton et al., "Correlation of Lipid Accumulation in Yeasts with Possession of ATP: Citrate Lyase," Journal of General Microbiology, vol. 127, 1981, pp. 169-176.
Connerton et al., "Comparison and cross-species expression of the acetyl-CoA synthetase genes of the ascomycete fungi, *Aspergillus nidulans* and *Neurospora crassa*," Molecular Microbiology, vol. 4, No. 3, 1990, pp. 451-460.
Dahlqvist et al., "Phospholipid: diacylglycerol acyltransferase: An enzyme that catalyzes the acyl-CoA-Independent formation of triacylglycerol in yeast and plants," PNAS, vol. 97, No. 12, Jun. 6, 2000, pp. 6487-6492.
EMBL Database, Accession No. Q4PHU1, Jul. 19, 2005, 3 pages.
EMBL Database, Accession No. Q5K8S0, Feb. 15, 2005, 3 pages.
Flikweert et al., "Pyruvate Decarboxylase: An Indispensable Enzyme for Growth of *Saccharomyces cerevisiae* on Glucose," Yeast, vol. 12, 1996, pp. 247-257.
Flipphi et al., "Regulation of the Aldehyde Dehydrogenase Gene (aldA) and Its Role in the Control of the Coinducer Level Necessary for Induction of the Ethanol Utilization Pathway in Aspergillus nidulans," The Journal of Biological Chemistry, vol. 276, No. 10, Mar. 9, 2001, pp. 6950-6958.
Folch et al., "A simple method for the isolation and purification of total lipides from animal tissues," The Journal of Biological Chemistry, vol. 226, No. 1, May 1957, pp. 497-509.
Hiesinger et al., "The acetyl-CoA synthetase gene ACS2 of the yeast *Saccharomyces cerevisiae* is coregulated with structural genes of fatty acid biosynthesis by the transcriptional activators Ino2p and Ino4p," FEBS Letters, vol. 415, 1997, pp. 16-20.

(Continued)

*Primary Examiner* — Kagnew H Gebreyesus
(74) *Attorney, Agent, or Firm* — Birch, Stewart, Kolasch & Birch, LLP

(57) ABSTRACT

The invention refers to fungal cells, and especially to oleaginous fungal cells that have been genetically modified to produce enzymes of the pyruvate dehydrogenase bypass route to enhance their lipid production. Especially the cells are modified to over-express genes encoding pyruvate decarboxylase (PDC), acetaldehyde dehydrogenase (ALD) and/or acetyl-CoA synthetase (ACS), optionally together with a gene encoding diacylglycerol acyltransferase (DAT), or to express genes encoding PDC together with ALD and/or ACS. Methods of producing lipids, biofuels and lubricants using the modified fungi are also disclosed as well as expression cassettes useful therein. A new enzyme having phospholipid: diacylglycerol acyltransferase (PDAT) activity and a polynucleotide encoding it are also disclosed, which are useful in the lipid production. A recombinant *Cryptococcus* cell and its construction is described.

13 Claims, 12 Drawing Sheets

(56) References Cited

OTHER PUBLICATIONS

Hynes et al., "ATP-Citrate Lyase Is Required for Production of Cytosolic Acetyl Coenzyme A and Development in Aspergillus nidulans," Eukaryotic Cell, vol. 9, No. 7, Jul. 2010, pp. 1039-1048.
Ishchuk et al., "Overexpression of pyruvate decarboxylase in the yeast *Hansenula polymorpha* results in increased ethanol yield in high-temperature fermentation of xylose," FEMS Yeast Research, vol. 8, 2008, pp. 1164-1174.
Mach et al., "Transformation of Trichoderma reesei based on hygromycin B resistance using homologous expression signals," Current Genetics, vol. 25, 1994, pp. 567-570.
Meesters et al., "Cloning and expression of the Δ9 fatty acid desaturase gene from Cryptococcus curvatus ATCC 20509 containing histidine boxes and a cytochrome b5 domain," Applied Microbiology and Biotechnology, vol. 47, 1997, pp. 663-667.
Mueller et al., "In Vivo Footprinting of a Muscle Specific Enhancer by Ligation Mediated PCR," Science, vol. 246, Nov. 10, 1989, pp. 780-786.
Nakazawa et al., "Use of the PDR4 Gene as a Dominant Selective Marker in Combination with Cerulenin for Prototrophic Strains in *Saccharomyces cerevisiae*," Journal of Fermentation and Bioengineering, vol. 76, No. 1, 1993, pp. 60-63, 1993.
Postma et al., "Enzymic Analysis of the Crabtree Effect in Glucose-Limited Chemostat Cultures of *Saccharomyces cerevisiae*," Applied and Environmental Microbiology, vol. 55, No. 2, Feb. 1989, pp. 468-477.
Pronk et al., "Pyruvate Metabolism in *Saccharomyces cerevisiae*," Yeast, vol. 12, 1996, pp. 1607-1633.
Ratledge et al., "The Biochemistry and Molecular Biology of Lipid Accumulation in Oleaginous Microorganisms," Advances in Applied Microbiology, vol. 51, 2002, pp. 1-51.
Saint-Prix et al., "Functional analysis of the ALD gene family of *Saccharomyces cerevisiae* during anaerobic growth on glucose: the Nadp+-dependent Ald6p and Ald5p isoforms play a major role in acetate formation," Microbiology, vol. 150, 2004, pp. 2209-2220.
Shiba et al., "Engineering of the pyruvate dehydrogenase bypass in *Saccharomyces cerevisiae* for high-level production of isoprenoids," Metabolic Engineering, vol. 9, 2007, pp. 160-168.
Skory, "Induction of Rhizopus oryzae Pyruvate Decarboxylase Genes," Current Microbiology, vol. 47, 2003, pp. 59-64.
Sorger et al., "Triacylglycerol biosynthesis in yeast," Applied Microbiology and Biotechnology, vol. 61, 2003, pp. 289-299.
Takahashi et al., "Nucleocytosolic Acetyl-Coenzyme A Synthetase is Required for Histone Acetylation and Global Transcription," Molecular Cell, vol. 23, Jul. 21, 2006, pp. 207-217.
Tehlivets et al., "Fatty acid synthesis and elongation in yeast," Biochimica et Biophysica Acta, vol. 1771, 2007, pp. 255-270.
Van Den Berg et al., "The Two Acetyl-coenzyme A Synthetases of *Saccharomyces cerevisiae* Differ with Respect to Kinetic Properties and Transcriptional Regulation," The Journal of Biological Chemistry, vol. 271, No. 46, Nov. 15, 1996, pp. 28953-28959.
Wolff et al., "Identification and analysis of genes involved in the control of dimorphism in Mucor circinelloides (syn. racemosus)," FEMS Yeast Research, vol. 2, 2002, pp. 203-213.
Wynn et al., "Biochemical events leading to the diversion of carbon into storage lipids in the oleaginous fungi *Mucor circinelloides* and *Mortierella alpina*," Microbiology, vol. 147, 2001, pp. 2857-2864.
Singapore Seach Report and Written Opinion dated Feb. 17, 2015 for Singapore Application No. 201209438-9.

GENETICALLY MODIFIED FUNGI AND THEIR USE IN LIPID PRODUCTION

FIELD OF THE INVENTION

The present invention relates to fungi, which have been genetically modified to enhance their lipid production. The invention also relates to a method for preparing the fungi, and to expression cassettes for genetic modification of the fungi. The invention further relates to a method of producing lipids by these fungi. The lipids produced are useful in manufacturing biofuels, lubricants and functional fatty acids. The invention thus also provides a method for producing biofuels and lubricants. Still further the invention provides a new enzyme protein that is useful in the methods, and a nucleic acid encoding it. Even further the invention relates to a recombinant *Cryptococcus* cell, and a method for its construction.

BACKGROUND OF THE INVENTION

Biofuels are current favorites to be the next generation transportation fuels. They are produced from renewable biological sources such as vegetable oils and animal fats. They are biodegradable, non-toxic and have a low emission profile. Due to the limited sources of biodiesel raw materials such as rape seed oil, soy bean oil or palm oil, it is of importance to expand biodiesel raw materials to non-food materials like microbes. The benefits of using microbes for production of oils are: they are affected neither by seasons nor by climates, they are able to produce high lipid contents, and the oils can be produced from a wide variety of sources with short production times, especially from residues with abundant nutrition. Microbiologically produced lipids may also be used e.g. for the production of functional fatty acids.

A few fungal species accumulate remarkable amounts of lipid in the cells. It has been observed that lipids accumulate in these so called oleaginous fungi under nitrogen limited conditions, which has resulted in a hypothesis for effective lipid accumulation (Review Ratledge and Wynn 2002 and references thenceforth). Nitrogen limitation causes activation of the AMP deaminase which utilizes AMP to produce $NH_4$. The decrease in AMP concentration inhibits the activity of mitochondrial isocitrate dehydrogenase (IDH) which is part of the mitochondrial tricarboxylic (TCA) cycle. Reduction in IDH activity results in equilibration of isocitrate to citrate by aconitase. Produced citrate is transferred to the cytosol where it is converted with Coenzyme A (CoA) to acetyl-CoA by ATP:citrate lyase (ACL) with ATP hydrolysis.

Cytosolic acetyl-CoA can be further used in fatty acid synthesis. A comprehensive review on fatty acid synthesis and elongation in yeast, especially in *Saccharomyces cerevisiae*, is that of Tehlivets et al., 1997. In the first step of fatty acid synthesis acetyl-CoA is carboxylated by the addition of carbon dioxide to malonyl-CoA by the enzyme acetyl-CoA carboxylase in an ATP demanding reaction. In the following reactions by the fatty acid synthase systems acyl and malonyl moieties from acyl-CoA and malonyl-CoA, respectively, are transferred to acyl carrier proteins (ACPs), after the acyl chain, typically initiated by acetyl-CoA, is condensed with malonyl-ACP followed by reduction of the 3-ketoacyl-ACP to 3-hydroxyacyl-ACP, dehydration to enoyl-ACP, and a second reduction to a saturated acyl-chain that is extended by two carbon atoms. These synthesis steps are usually repeated seven times resulting in palmitoyl ACP (C16:0). Palmitic acid and intermediates of the fatty acid synthesis after hydrolysed to acyl-CoAs by hydrolase/thioesterase, can be further modified by different elongases and desaturases to different length acyl-chains with or without double bonds. In one cycle of fatty acid synthesis two NADPHs are required in the reduction steps. Acyl-CoAs can be further synthesised to triacylglycerols.

Triacylglycerol synthesis starts from glycerol-3-phosphate or dihydroxyacetone phosphate which is acylated (dihydroxyacetone-phosphate also reduced) to 1-acyl-glycerol-3-phosphate which is further acylated to phosphatidic acid. Phosphatidic acid can be further dephosphorylated to diacylglycerol. Diacylglycerol is further acylated to triacylglycerol mainly by acyl-CoA:diacylglycerol acyltransferase (DGAT) and phospholipid:diacylglycerol acyltransferase (PDAT) utilizing acyl-CoA or phosphatidylcholine, respectively, as acyl donors. The triacylglycerol pathway in yeast *S. cerevisiae* is described in more detail in a mini-review of Sorger and Daum 2003.

Phospholipid:diacylglycerol acyltransferase (PDAT) encoding genes originating from *S. cerevisiae* and *Yarrowia lipolytica* have been expressed in yeasts *S. cerevisiae* and *Y. lipolytica* to enhance their triacylglycerol production (WO00/60095 and WO2005/003322, respectively). WO2009/126890 provides systems for producing engineered oleaginous yeast or fungi that express carotenoids. Oleaginy is promoted e.g. by increased or heterologous expression of DGAT or PDAT, whereas reducing the activity of PDC is expected to promote oleaginy.

Methods of manufacturing biodiesel and other oil-based compounds using glycerol as an energy source in fermentation of oil-bearing microorganisms have been described e.g. in US2009/0004715. Methods of producing lipid-based biofuels from cellulose containing feedstock by heterotrophic fermentation of microorganisms have been described in US2009/0064567. Both publications focus on the use of algae as lipid producers. No details are given. WO2007/136762 provides genetically engineered microorganisms that produce desired products from the fatty acid biosynthetic pathway.

With the above-described triacylglycerol production pathway high triglyceride yields indicated as triglyceride production per used carbon source cannot be achieved or triacylglycerol production per cell biomass cannot be significantly enhanced. In general, lipids especially triglycerides are produced when nitrogen becomes a growth limiting factor at the late logarithmic or early stationary growth phase resulting in a low triglyceride production rate compared e.g. to yeast ethanol production. Additionally, the need of several carbons and reduced cofactors in synthesis of triacylglycerol result in low yield per used carbon. The present invention uses another route for microbial lipid production. In the present invention microbial lipid production rate and yields are enhanced, and the need of reduced cofactors from the outside of the lipid pathway is decreased. The present invention further provides lipid production that is not linked to nitrogen limitation.

SUMMARY OF THE INVENTION

The present invention is based on the use of a pyruvate dehydrogenase bypass route for producing cytosolic acetyl-CoA. The invention makes use of an active cytosolic pathway for acetyl-CoA production, which proceeds via the enzymatic reaction catalyzed by pyruvate decarboxylase (PDC). This pathway is known in Crabtree-positive yeast *S. cerevisiae*, where it is essential for cytosolic acetyl-CoA production, but it has not been characterized in oleaginous yeasts and oleaginous filamentous fungi. In oleaginous fungi another cytosolic pathway for acetyl-CoA production, proceeding via the reaction catalyzed by pyruvate dehydrogenase (PDH) is well known and which has been shown to be essential for cytosolic acetyl-CoA production from pyruvate. This pathway operates via mitochondria and in this pathway a higher fraction of carbon is lost than in the pathway via pyruvate decarboxylase. In the pyruvate decarboxylase pathway, exploited in this invention, a higher fraction of carbon is directed to triacylglycerol and it is not dependent on mitochondrial enzyme activities. Further, it produces NAD(P)H which is needed in the following fatty acid synthesis. The pyruvate dehydrogenase bypass route optionally together with an enhanced diacylglycerol acyltransferase activity as provided by the invention removes many bottlenecks in microbial lipid production.

The invention is directed to genetically modified fungal cells that have been modified to enhance the expression of a nucleic acid encoding PDC, ALD, ACS and/or DAT, and to methods of constructing them.

In particular the invention is directed to a genetically modified oleaginous fungal cell comprising at least one nucleic acid with enhanced expression encoding an enzyme selected from the group consisting of pyruvate decarboxylase (PDC), acetaldehyde dehydrogenase (ALD) and acetyl-CoA synthetase (ACS).

The invention is further directed to a genetically modified fungal cell comprising:
 a) a nucleic acid with modified expression encoding a pyruvate decarboxylase (PDC) enzyme, and
 b) at least one nucleic acid with modified expression encoding an enzyme selected from the group consisting of acetaldehyde dehydrogenase (ALD), acetyl-CoA synthetase (ACS) and diacylglycerol acyltransferase (DAT).

The invention is also directed to a genetically modified fungal cell comprising:
 a) at least one nucleic acid with modified expression encoding an enzyme selected from the group consisting of pyruvate decarboxylase (PDC), acetaldehyde dehydrogenase (ALD) and acetyl-CoA synthetase (ACS), and
 b) a nucleic acid with modified expression encoding a diacylglycerol acyltransferase (DAT) enzyme.

The invention is also directed to a method of producing lipids comprising cultivating the genetically modified fungal cell according to the invention in a medium containing carbon and nitrogen sources, and recovering the lipids produced.

The invention is further directed to a method of producing biofuel, or lubricant said method comprising cultivating the genetically modified fungal cell according to the invention in a medium containing carbon and nitrogen sources, and recovering the lipids produced, and optionally esterifying said lipids to obtain biodiesel or lubricant, or hydrogenizing the lipids to obtain renewable diesel or lubricant.

The invention is still further directed to methods of preparing i.e. constructing a genetically modified fungal cell of the invention, said methods comprising transforming a fungal cell with
 at least one nucleic acid with enhanced expression encoding an enzyme selected from the group consisting of pyruvate decarboxylase (PDC), acetaldehyde dehydrogenase (ALD) and acetyl-CoA synthetase (ACS); or with
 a) a nucleic acid with enhanced expression encoding a pyruvate decarboxylase (PDC) enzyme, and
 b) at least one nucleic acid with enhanced expression encoding an enzyme selected from the group consisting of acetaldehyde dehydrogenase (ALD), acetyl-CoA synthetase (ACS) and diacylglycerol acyltransferase (DAT); or with
 a) at least one nucleic acid with modified expression encoding an enzyme selected from the group consisting of pyruvate decarboxylase (PDC), acetaldehyde dehydrogenase (ALD) and acetyl-CoA synthetase (ACS), and
 b) a nucleic acid with modified expression encoding a diacylglycerol acyltransferase (DAT) enzyme.

In addition the invention is directed to an expression cassette comprising
 a) at least one nucleic acid with modified expression encoding an enzyme selected from the group consisting of pyruvate decarboxylase (PDC), acetaldehyde dehydrogenase (ALD) and acetyl-CoA synthetase (ACS), and
 b) a nucleic acid with modified expression encoding a diacylglycerol acyltransferase (DAT) enzyme.

Conveniently the genetically modified fungal cells are constructed according to the invention by transforming the fungal cell with the nucleic acid(s) encoding said enzyme(s) resulting in enhanced enzyme activity of said enzyme.

Still further the invention is directed to an enzyme protein having phosholipid:diacylglycerol acyltransferase (PDAT) activity and at least 40% sequence identity to SEQ ID NO:52, or an enzymatically active fragment or variant thereof, and to an isolated nucleic acid molecule selected from the group consisting of: a) a nucleic acid encoding said protein, b) a nucleic acid comprising the nucleotide sequence of SEQ ID NO:53 or SEQ ID NO:93, c) a complementary strand of a) or b), and d) a sequence that is degenerate as a result of the genetic code to anyone of sequences a)-c).

The invention is additionally directed to a genetically modified fungal cell comprising a nucleic acid with modified expression encoding said PDAT, and to a method of producing lipids, comprising cultivating said genetically modified fungal cell in a medium containing carbon and nitrogen sources, and recovering the lipids produced.

Still further the invention is directed to the use of a genetically modified fungal cell of the invention for producing lipids, biofuels, biodiesel, renewable diesel or lubricants. The use for producing lipids includes e.g. the use for producing precursors of fatty acids e.g. of functional fatty acids, and for producing the fatty acids or functional fatty acids.

As a still further aspect, the invention is directed to a genetically modified *Cryptococcus* cell, which has been modified to enhance the expression of a heterologous nucleic acid, and to a method of constructing the cell, said method comprising transforming a *Cryptococcus* cell with a nucleic acid encoding a heterologous protein.

Specific embodiments of the invention are set forth in the dependent claims. Other objects, details and advantages of the present invention will become apparent from the following drawings, detailed description and examples.

DETAILED DESCRIPTION OF THE INVENTION

Figure 1:
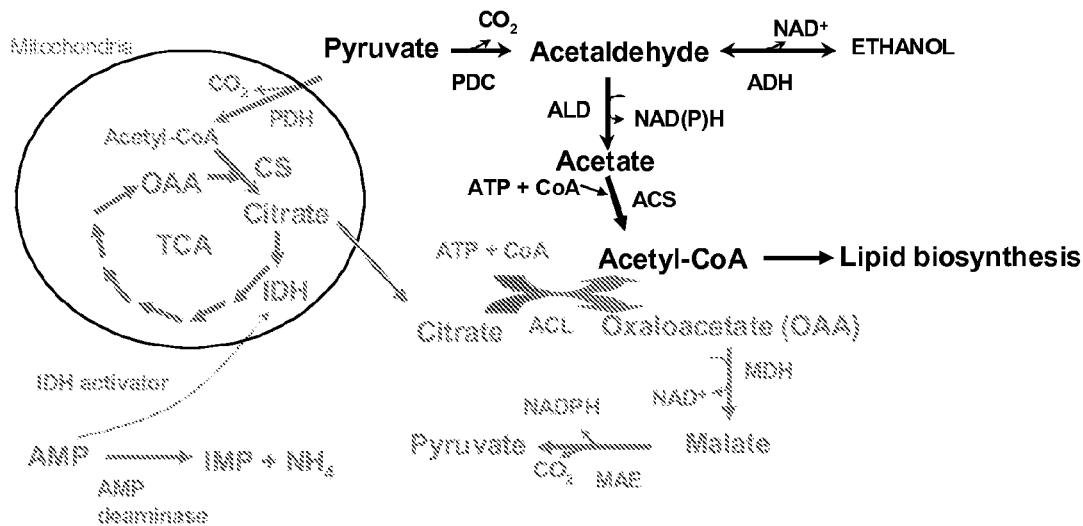
FIG. 1 shows probable metabolic routes for cytosolic acetyl-CoA production via the pyruvate dehydrogenase route in grey, and via the pyruvate dehydrogenase bypass route i.e. the pyruvate decarboxylase route in black.

The presumed pyruvate dehydrogenase (PDH) pathway for producing cytosolic acetyl-CoA is shown in grey in FIG. 1. First cytosolic pyruvate is transported into the mitochondria where it is oxidatively decarboxylated to acetyl-CoA and carbon dioxide by the pyruvate dehydrogenase complex. The resulting acetyl-CoA is then entering the tricarboxylic (TCA) cycle by citrate synthase (CS) which catalyses the condensation reaction of the two-carbon acetate residue from acetyl-CoA and a molecule of four-carbon oxaloacetate (OAA) to form the six-carbon citrate. Citrate is then isomerised to isocitrate which is the substrate for mitochondrial isocitrate dehydrogenase (IDH). Under limited nitrogen supply AMP deaminase activity increases leading to production of IMP and ammonium from AMP. The decrease in the amount of AMP results in decrease in mitochondrial isocitrate dehydrogenase (IDH) activity, whereby the amount of citrate in the mitochondria increases. The mitochondrial citrate is transported into the cytosol, where ATP: citrate lyase (ACL) converts citrate, ATP and CoA into acetyl-CoA and oxaloacetate. The oxaloacetate is degraded by malate dehydrogenase (MDH) to malate, which in turn is converted to pyruvate and carbon dioxide by malic enzyme (MAE) under production of NADPH, which is an important cofactor in fatty acid synthesis. In this invention cytosolic acetyl-CoA is produced via a pyruvate dehydrogenase bypass pathway, which is shown in black in FIG. 1. This pathway is also called the pyruvate decarboxylase pathway. In this pathway pyruvate is decarboxylated to acetaldehyde and carbon dioxide by pyruvate decarboxylase (PDC). Acetaldehyde is further oxidised to acetate by $NADP^+$ (or $NAD^+$)-dependent acetaldehyde dehydrogenase (ALD). Acetate is then converted to acetyl-CoA by acetyl-CoA synthetase (ACS) with ATP and Coenzyme A. In this cytosolic pathway [pyruvate+CoA+ATP+NAD(P)$^+$=Acetyl-CoA+$CO_2$+NAD(P)H+AMP+PPi+H$^+$] the overall acetyl-CoA yield is higher than in the pyruvate dehydrogenase-ATP:citrate lyase pathway [pyruvate+CoA+ATP+NAD$^+$ (in mitochondria)+oxaloacetate (in mitochondria)=Acetyl-CoA+$CO_2$+ADP+Pi+NADH (in mitochondria)+H$^+$+ oxaloacetate (in cytosol)].

Figure 2:
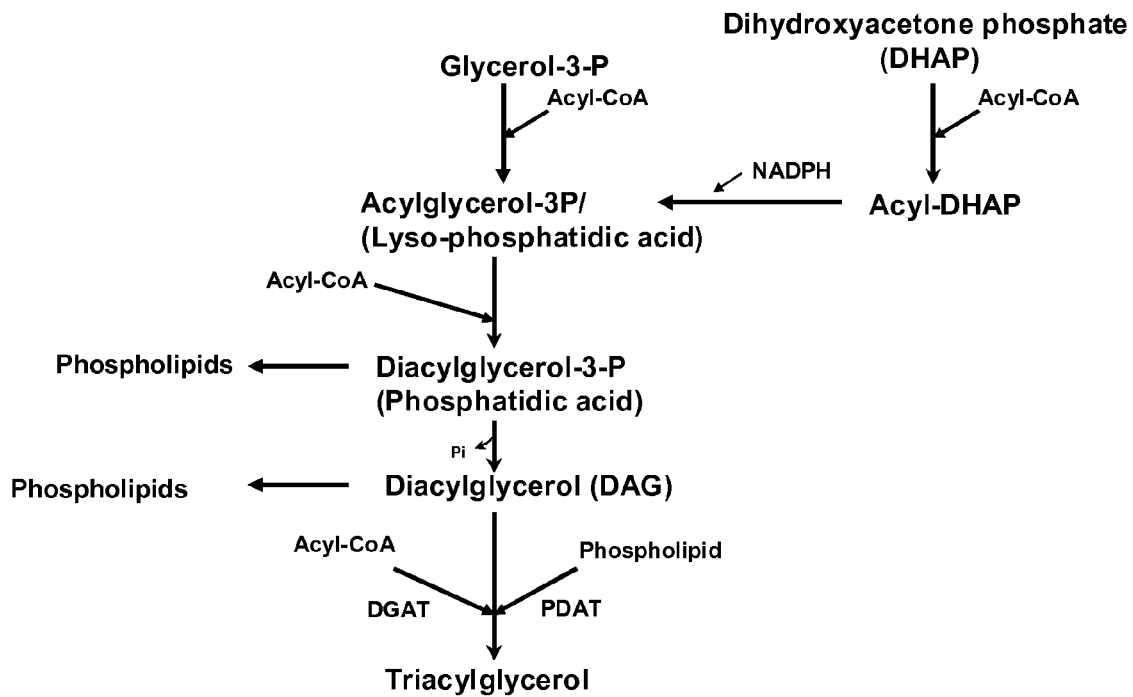
FIG. 2 shows the metabolic route for triacylglycerol production.

Cytosolic acetyl-CoA is used by NADPH-dependent fatty acid synthase (FAS) and other enzymes for the production of acyl-CoA esters of different length, which then are attached to for example glycerol through the triglyceride metabolic pathway shown in FIG. 2. In the last step of this pathway an acyl group from acyl-CoA or from a phospholipid is attached to the diacylglycerol by acyl-CoA:diacylglycerol acyltransferase (DGAT) or phospholipid:diacylglycerol acyltransferase (PDAT).

In the present invention triacylglycerol production of fungi will be enhanced by overexpressing at least one gene, which encodes an enzyme involved in the pyruvate decarboxylate pathway for converting pyruvate to acetyl-CoA as shown in FIG. 1, together with a gene, which encodes an enzyme that catalyses the acylation of diacylglycerol to triacylglycerol as shown in FIG. 2.

Lipid production including triacylglycerol production in the cell is a highly NADPH demanding process. E.g. in production of 1 mole of oleic acid (9-octadecenoic acid) 17 mole of NADPH is needed. NADPH produced by malic enzyme has been proposed to be the main source for NADPH needed in fatty acid synthesis. Said NADPH production occurs totally outside the cytosolic acetyl-CoA production pathway resulting in the consumption of extra carbons in NADPH production, even though the reaction of the malic enzyme is linked to the degradation of the oxaloacetate produced by ATP:citrate lyase. In the present invention fatty acid and further triacylglycerol production is connected directly to NADPH cofactor production by NADP-dependent acetaldehyde dehydrogenase thus reducing the need to produce NADPH outside the triglyceride production pathway resulting in an increased triacylglycerol yield. The $NADP^+$-dependent acetaldehyde dehydrogenase produces simultaneously one NADPH and one acetate molecule from NADP+ and acetaldehyde resulting in production of one mole of NADPH per one mole of pyruvate. This means that half of the NADPH molecules needed in the fatty acid synthesis are produced simultaneously with the cytosolic acetyl-CoA production. This simultaneous NADPH production with lower carbon loss during production of cytosolic acetyl-CoA results in a better yield in fatty acid production following also better yield in triacylglycerol production. In this invention only one carbon is lost from the carbon skeleton downstream of pyruvate prior to cytosolic acetyl-CoA. Additionally, no side reactions are needed to cleave metabolites further outside the triglyceride production pathway. The production of cytosolic acetyl-CoA via the pyruvate dehydrogenase bypass completes the existing pyruvate dehydrogenase pathway for cytosolic acetyl-CoA production.

Triacylglycerols and other lipids are naturally produced in fungi via the pyruvate dehydrogenase pathway during growth, but the main triacylglycerol and lipid accumulation occurs when excess citrate will be available after nitrogen limitation in the late stage of cultivation. This triacylglycerol production in late logarithmic or stationary phases of cultivation results in low triacylglycerol production rates, especially at the early stage of cultivation. In this invention expression of the pyruvate dehydrogenase bypass catalyzed by PDC, ALD, and ACS results in a situation where triacylglycerol accumulation is not linked to nitrogen limitation thus allowing enhanced triacylglycerol production during cultivation resulting in a better triacylglycerol production rate. The earlier triacylglycerol production is further enhanced by expressing an acyltransferase such as a phospholipid:diacylglycerol acyltransferase (PDAT) encoding gene e.g. under a constitutive promoter thus increasing triacylglycerol concentration at the expense of phospholipids.

Contrary to oleaginous yeasts and moulds like *Cryptococcus curvatus* and *Mucor circinelloides*, *S. cerevisiae* lacks the pyruvate dehydrogenase route for acetyl-CoA production. In this Crabtree-positive yeast cytosolic acetyl-CoA, and further fatty acids and triacylglycerols, are produced only via pyruvate dehydrogenase bypass. The essential role of the pyruvate dehydrogenase bypass including the enzymes pyruvate decarboxylate (PDC), acetaldehyde dehydrogenase (ALD) and acetyl-CoA synthetase (ACS) in cytosolic acetyl-CoA and further in lipid production and the role of ALD in the generation of reducing equivalents (NADH and NADPH) in *S. cerevisiae* has been described for example in Flikweert et al. 1996, Pronk et al 1996, Saint-Prix et al 20041 In US2009/0053797 expression of endogenous NADP-dependent acetaldehyde dehydrogenase (ALD6) gene and native or modified endogenous ACS1 gene or *Salmonella enterica* acetyl-CoA synthetase (ACS1) gene in *S. cerevisiae* resulted in an increased concentration of cytosolic acetyl-CoA in the production of isoprenoids. Shiba et al., 2007 found that overexpression of ALD6 and ACS1 in *S. cerevisiae* increased cytosolic acetyl-CoA derived amorphadiene overproduction, whereas overexpression of ACS2 with ALD6 did not. The acetyl-CoA synthetase isoforms ACS1 and ACS2 behave differently in *S. cerevisiae*: ACS1 gene has been shown to be under glucose repression whereas ACS2 gene has been shown to be constitutively expressed and co-regulated with structural genes of fatty acid biosynthesis (van den Berg et al 1996, Hiesinger et al. 1997).

The essential role of the PDH bypass in *S. cerevisiae* has been described: Deletion of three structural genes for pyruvate decarboxylase (PDC1, PDC5 and PDC6) results in loss of growth in a defined glucose medium (Flikweert et al 1996, Pronk et al. 1996), and deletion of two acetyl-CoA synthetase encoding genes ACS1 and ACS2 is lethal on all carbon sources (Takahashi et al 2006 and van den Berg et al 1996), indicating that there is no alternative route for cytosolic acetyl-CoA production in *S. cerevisiae*. The enhanced expression of this pathway has been found to induce cytosolic acetyl-CoA production in *S. cerevisiae* (e.g. US2009/0053797 and WO2008/080124). However, the existence and functionality of the pyruvate dehydrogenase bypass pathway in oleaginous yeasts or moulds has not been described in the literature.

PDC has been characterised e.g. from the *Rhizopus oryzae*, which in addition to lipids produced ethanol (Skory 2003). Also, ALD and ACS have been characterised from some of the oleaginous fungi e.g. *A. nidulans* (Flipphi et al. 2001, Connerton et al. 1990). Still, it has also been shown that deletion of the only cytoplasmic ACS encoding gene from *A. nidulans* had no effect on growth on glucose (Sandeman et al. 1989). Instead, it has been shown in several articles that the cytosolic acetyl-CoA for lipid production will be produced via pyruvate dehydrogenase and ATP: citrate lyase (ACL) in oleaginous fungi (Wynn et al 2001, Boulton and Ratledge 1981). ATP:citrate lyase has been shown to be absent from the non-oleaginous yeasts (Boulton and Ratledge 1981). E.g. ACL is absent from the sequenced members of the Saccharomycotina with the exception of *Y. lipolytica* which is oleaginous yeast. The essential role of ACL for cytosolic acetyl-CoA production has also been shown at a functional level by detecting the ad gene from *A. nidulans*. This deletion strain could not grow in the absence of external sources of cytoplasmid acetyl-CoA, which strongly suggests that ACL activity is required to generate cytoplasmic acetyl-CoA. This also indicates the absence of any pyruvate dehydrogenase bypass pathway, which could compensate ad deletion (Hynes and Murray 2010). The production of cytosolic acetyl-CoA via ATP:citrate lyase in oleaginous fungi is also suggested in the patent applications WO2005/003322 and US2006/094087, where diacylglycerol transferase encoding genes have been expressed to enhance triacylglycerol production.

The term "pyruvate dehydrogenase bypass" refers to an alternative route to the pyruvate dehydrogenase reaction for the conversion of pyruvate to acetyl-CoA. The pyruvate dehydrogenase bypass comprises the enzymes pyruvate decarboxylase (PDC), acetaldehyde dehydrogenase (ALD) and acetyl-CoA synthetase (ACS). It has been shown in literature that the pyruvate dehydrogenase bypass is not essential in Crabtree-negative yeasts.

In the present context the corresponding genes encoding the enzyme proteins are indicated in italics.

The term "PDC" refers to pyruvate decarboxylase enzyme (EC 4.1.1.1). This enzyme catalyses the thiamine pyrophosphate- and $Mg^{2+}$-dependent decarboxylation of pyruvate to acetaldehyde and carbon dioxide. A preferred PDC is one of a Crabtree-positive organism. Preferably the PDC is a fungal PDC, especially of a Crabtree-positive fungus, such as *S. cerevisiae* e.g. PDC1 of *S. cerevisiae* (GenBank accession number CAA54522, version number CAA54522.1). According to one embodiment of the invention the PDC1 contains the amino acid sequence of SEQ ID NO:95, and/or is encoded for example by a polynucleotide containing the nucleotide sequence of SEQ ID NO:94, SEQ ID NO:96 or SEQ ID NO:97.

The term "ALD" refers to acetaldehyde dehydrogenase enzyme (EC 1.2.1.5 and EC 1.2.1.4). This enzyme catalyses the reaction where acetaldehyde is oxidized to acetate, and $NAD^+$ or $NADP^+$-cofactor is reduced to NADH or NADPH, respectively. $NADP^+$-specific ALDs are preferred. In the present invention the ALD is preferably a fungal ALD, more preferably of *S. cerevisiae*, and most preferably it is *S. cerevisiae* ALD6, which is encoded for example by a polynucleotide of SEQ ID NO:48 or 49, and/or comprises the amino acid sequence of SEQ ID NO:47. Further, the ALD is preferably a cytosolic ALD. ALD6 is cytosolic. Cytosolic ALD can be modified from mitochondrial isoforms of ALD by removing the mitochondrial targeting signal from the originally mitochondrial ALD by genetic engineering. The cleavage site of the mitochondrial targeting signal can be decided e.g. with programs designed for this purpose such as MITOPROT. Examples of mitochondrial ALD, which can be modified to be cytosolic are *S. cerevisiae* ALD4 and ALD5 encoding genes. Suitable ALD encoding genes can be found from databases e.g. KEGG Enzyme database and Brenda with EC numbers 1.2.1.4 and 1.2.1.5. Table 1 contains examples of $NAD(P)^+$ dependent acetaldehyde dehydrogenases.

TABLE 1

$NAD(P)^+$ -dependent acetaldehyde dehydrogenase enzymes

| Organism | Accession number of the amino acid sequence | Version number of the amino acid sequence | Database |
| --- | --- | --- | --- |
| Saccharomyces cerevisiae | AAB68304 | AAB68304.1 | GenBank |
| Saccharomyces cerevisiae | DAA07732 | DAA07732.1 | GenBank |
| Saccharomyces cerevisiae | DAA11133 | DAA11133.1 | GenBank |
| Aspergillus niger | A2QMA4 | A2QMA4.1 | TrEMBL |
| Aspergillus niger | A2QiG1 | A2QiG1.1 | TrEMBL |
| Aspergillus niger | A5AAZ8 | A5AAZ8.1 | TrEMBL |
| Aspergillus niger | A2Q9V7 | A2Q9V7.1 | TrEMBL |
| Aspergillus fumigatus | Q4WQP1 | Q4WQP1.1 | TrEMBL |
| Pichia angusta | Q12648 | Q12648 | Swiss-Prot |
| Pichia stipitis | A3M013 | A3M013.2 | TrEMBL |
| Candida dubliniensis | B9W6J2 | B9W6J2.1 | TrEMBL |
| Candida glabrata | CAG59952 | CAG59952.1 | GenBank |
| Kluyveromyces lactis | CAH00079 | CAH00079.1 | Genbank |
| Lachancea thermotolerans | CAR23570 | CAR23570.1 | Genbank |
| Burkholderia xenovorans | Q13WK4 | Q13WK4.1 | TrEMBL |
| Vibrio harveyi | Q56694 | Q56694.1 | Swiss-Prot |
| Mus musculus | P47739 | P47739.1 | Swiss-Prot |
| Mus musculus | Q80VQ0 | Q80VQ0.1 | Swiss-Prot |
| Rattus norvegicus | P11883 | P11883.3 | Swiss-Prot |
| Rattus norvegicus | Q5XI42 | Q5XI42.1 | Swiss-Prot |
| Canis lupus familiaris | A3RF36 | A3RF36.1 | Swiss-Prot |
| Bos taurus | P30907 | P30907.2 | Swiss-Prot |
| Bos taurus | Q1JPA0 | Q1JPA0.1 | Swiss-Prot |
| Homo sapiens | P30838 | P30838.2 | Swiss-Prot |
| Homo sapiens | P43353 | P43353.1 | Swiss-Prot |

The term "cytosolic" refers to a fluid component of the cytoplasm excluding organelle and other suspended intracellular structures.

The term "ACS" refers to acetyl-CoA synthetase enzyme (EC 6.2.1.1). The enzyme catalyses the reaction where acetyl-CoA is formed from acetate and CoA with hydrolysis of ATP. Preferably the ACS is a fungal ACS, more preferably S. cerevisiae ACS, especially S. cerevisiae ACS2. Preferably the ACS encoding gene to be expressed is a gene, which is not under glucose repression and/or which gene product is not subject to post-translational regulation e.g. acetylation, in the original species. In a particular embodiment the ACS contains the sequence of SEQ ID NO:50. Several yeasts such as Candida albicans have genes similar to S. cerevisiae ACS2, which most likely are not under post-translational regulation. This abolishes the need to modify the existing gene. According to one embodiment ACS2 is encoded by a polynucleotide having the sequence of SEQ ID NO:51 or 92.

The term "DAT" refers to diacylglycerol acyltransferase enzyme (EC 2.3.1.X). The enzyme catalyses a reaction where an acyl group is transferred to 1,2-diacylglycerol to the position sn-3. DAT includes both acyl-CoA:diacylglycerol acyltransferase (DGAT, EC 2.3.1.20) and phospholipid:diacylglycerol acyltransferase (PDAT). Preferably the DAT is PDAT.

The term "PDAT" refers to phospholipid:diacylglycerol acyltransferase enzyme (EC 2.3.1.158). The enzyme catalyses a reaction where an acyl group from a phospholipid is transferred to 1,2-diacylglycerol to the position sn-3 via an acyl-CoA-independent mechanism. Preferably the PDAT is of fungal origin, and more preferably of an oleaginous fungus. In one preferred embodiment the PDAT is a Rhizopus oryzae PDAT, and most preferably it is encoded by a polynucleotide that contains the sequence of SEQ ID NO:53 or 93. Preferably the PDAT contains an amino acid sequence having at least 40% identity to SEQ ID NO:52, or an enzymatically active fragment or variant thereof.

In particular preferred embodiments of the invention the encoded enzyme comprises an amino acid sequence with a sequence identity of at least 30%, 40%, 50%, 60%, 70%, 80%, 90%, 95%, 98%, 99% or 100% to SEQ ID NO:95, 47, 50, or 52, or an enzymatically active fragment or variant thereof.

Percent identity of amino acid sequences can conveniently be computed using BLASTP version 2.2.23 software with default parameters. Sequences having an identities score and a positives score of a given percentage, using the BLASTP version 2.2.23 algorithm with default parameters, are considered to be that percent identical or homologous (Altschul et al. 1997).

It is well known that deletion, addition or substitution of one or a few amino acids does not necessarily change the catalytic properties of an enzyme protein. Therefore the invention also encompasses variants and fragments of the given amino acid sequences having the stipulated enzyme activity. The term "variant" as used herein refers to a sequence having minor changes in the amino acid sequence as compared to a given sequence. Such a variant may occur naturally e.g. as an allelic variant within the same strain, species or genus, or it may be generated by mutagenesis or other gene modification. It may comprise amino acid substitutions, deletions or insertions, but it still functions in substantially the same manner as the given enzymes, in particular it retains its catalytic function as an enzyme.

A "fragment" of a given protein sequence means part of that sequence, i.e. a sequence that has been truncated at the N- and/or C-terminal end. It may for example be the mature part of a protein comprising a signal sequence, or it may be only an enzymatically active fragment of the mature protein.

The term "lipid" refers to a group of organic compounds that are relatively or completely insoluble in water but soluble in nonpolar organic solvents. These properties are a result of long hydrocarbon tails, which are hydrophobic in nature. The term thus encompasses fats, oils, waxes, fatty acids, fatty acid derivatives, like phospholipids, glycolipids, acylglycerids such as monoglycerides, diglycerides, and triglycerides and terpenoids such as carotenoids and steroids.

The term "fatty acid" refers to a compound obtainable via condensation of malonyl coenzyme A units by a fatty acid synthase system. They may be saturated or unsaturated. "Functional fatty acid" refers to a fatty acid compound having at least one functional group e.g. a hydroxyl (—OH) or carboxyl (—COOH) group within the fatty acid and being responsible for the characteristic chemical reactions of those molecules.

The term "fatty acid derivative" refers to a compound having at least one esterified fatty acyl group. Fatty acid derivatives include e.g. phospholipids, glycolipids and acylglycerides.

The term "acylglyceride" is synonymous with "acylglycerol" and refers to a compound having a glycerol moiety with one or several hydroxyl groups esterified to a fatty acid.

The terms "monoglyceride" and "monoacylglycerol" refer to a glyceride where one fatty acid residue has been esterified to a glycerol molecule. The fatty acid residue in the monoacylglycerol can be a short or long chain fatty acid with or without double bonds.

The terms "diglyceride" and "diacylglycerol" and "DAG" refer to glyceride where two fatty acid residues have been esterified to a glycerol molecule. Fatty acid residues in diacylglycerol can be short or long chain fatty acids with or without double bonds.

The terms "triglyceride" and "triacylglycerol" and "TAG" refer to a glyceride where three fatty acid residues have been esterified to a glycerol molecule. Fatty acid residues in triacylglycerol can be short or long chain fatty acids with or without double bonds. Triacylglycerol is the major acylglycerol group in oleaginous fungi.

The term "acyl-CoA" refers to a fatty acid residue, which has been esterified to a CoA molecule. Fatty acid residues in acyl-CoA can be short or long chain fatty acids with or without double bonds.

The term "phospholipids" refers to any lipid containing a diglyceride combined with a phosphate group and a simple organic molecule such as choline or ethanolamine.

The term "glycolipid" refers to a lipid attached with a carbohydrate.

The term "fat" refers to a group of organic compounds that are relatively or completely insoluble in water but soluble in nonpolar organic solvents and which are solids at normal room temperature.

The term "oil" refers to a group of organic compounds that are relatively or completely insoluble in water but soluble in nonpolar organic solvents and which are liquids at normal room temperature.

Generally fats and oils are triesters of glycerol and fatty acids.

The term "wax" refers to a compound that may contain long-chain alkanes, esters, polyesters and hydroxyl esters of long-chain primary alcohols and fatty acids.

The term "terpenoid" refers to a compound formally derived from hydrocarbon isoprene.

The term "steroid" refers to a terpenoid lipid compound having a sterane core and additional functional groups. Sterols are special forms of steroids, with a hydroxyl group at the atom C-3 and a skeleton derived from cholestane.

The term "carotenoids" refers to a compound belonging to the category of tetraterpenoids. Structurally they are in the form of a polyene chain, which is sometimes terminated by rings.

In the present invention fungal cells are genetically modified to express particular enzymes. The cells can be genetically modified to produce increased levels of lipid by transforming them with nucleic acids that have been modified to enhance the expression of nucleic acids encoding at least one of PDC, ALD and ACS, together with a nucleic acid that has been modified to enhance the expression of a nucleic acid encoding DAT so as to allow overexpression of the enzymes. A "genetically modified" organism or cell is an organism or cell that comprises an expression modified nucleic acid. It may be a recombinant organism or cell, or a host organism or cell, or a mutant.

"Nucleic acid" is a macromolecule comprising a chain of monomeric nucleotides i.e. a polynucleotide. It can be e.g. DNA such as cDNA or genomic DNA or mRNA, and it can be e.g. recombinantly or synthetically produced, double or single stranded, encompassing both sense and antisense strands.

"Recombinant" nucleic acid refers to an artificial combination of at least two otherwise separated sequences, i.e. to a not naturally occurring combination of nucleic acids.

"Nucleic acid with modified expression" as used herein denotes nucleic acids that are foreign or exogenous to the host meaning that they are not naturally found in said host. The term also includes nucleic acids that are endogenous i.e. naturally found in the host, but which are produced in an unnatural amount e.g. as multiple copies, or nucleic acids that differ in sequence from the naturally occurring nucleic acids but encode the same type of protein. Further, the term includes nucleic acids comprising at least two nucleotide sequences that do not occur in the same relationship to each other in nature, such as e.g. an endogenous protein encoding sequence that is operably linked to a transcriptional control element e.g. a promotor and/or terminator in a way that does not occur in nature. Said promotor and/or terminator can be of endogenous or exogenous origin. High copy number plasmids comprising the protein encoding nucleotide sequence are also considered nucleic acids with modified expression. The above mentioned expression modified nucleic acids encompass recombinant nucleic acids, herein also called heterologous nucleic acids. Alternatively the expression modified nucleic acid can be a mutated nucleic acid. "Modified expression" in this context is used only in the meaning of over-expression i.e. "enhanced expression". The enhanced expression results in overproduction of the expressed protein in the modified organism compared to that in an unmodified organism.

In one embodiment of the invention the nucleic acid with modified expression contains an exogenous gene encoding PDC, ALD, ACS or DAT derived from another organism. The genes encoding PDC, ALD or ACS can be obtained from yeast such as *Saccharomyces cerevisiae, Candida glabrata, Dekkera bruxellensis, Kluyveromyces lactis, Kluyveromyces marxianus, Pichia pastoris, Pichia angusta, Pichia stipitis, Zygosaccharomyces rouxii, Issatchenkia terricola, Debaryomyces hansenii, Candida angusta* and *Pichia guilliermondii*, and the DAT can be obtained from yeast or filamentous fungi such as *Saccharomyces cerevisiae, Candida glabrata, Zygosaccharomyces rouxii, Lachancea thermotolerans, Ashbya gossypii, Cryptococcus curvatus, Cryptococcus albidus, Lipomyces lipofer, Lipomyces starkeyi, Lipomyces tetrasporus, Rhodosporidium toruloides, Rhodotorula glutinis, Rhodotorula graminis, Yarrowia lipolytica, Aspergillus nidulans, Aspergillus oryzae, Fusarium oxysporum, Humicola lanuginose, Mortierella alpina, Mortierella vinacea, Mucor circinelloides, Mucor plumbeus, Penicillium spinulosum,* and *Rhizopus oryzae.* In another embodiment the enzyme genes to be expressed are endogenous genes, the promotor of which is replaced with another promotor, preferably a constitutive promotor, or the existing promotor is modified to become a constitutive promotor.

Proteins or polynucleotides "derived from", "originated from" or "obtained from" a particular organism encompass products isolated from said organism, as well as modifications thereof. A protein derived from a particular organism may be a recombinantly produced product, which is identical to, or a modification of the naturally occurring protein. The protein may also be modified e.g. by glycosylation, phosphorylation or other chemical modification. Products derived from the particular organism also encompass mutants and natural variants of the products, where one or more nucleic acid and/or amino acid is deleted, inserted and/or substituted.

Expression of any combination of the genes of the pyruvate dehydrogenase bypass route may be linked to expression of the DAT encoding gene. The expression of the DAT encoding gene may for example be combined to the expression of an ALD encoding gene, or an ACS encoding gene, or a PDC encoding gene. In another embodiment both ASC and ALD, or both PDC and ACS, or PDC and ALD, are overexpressed, and in still another all PDC, ALD and ACS are overexpressed together with the DAT encoding gene. In one specific embodiment of the invention the expression of *S. cerevisiae* ALD encoding gene ALD6 is linked to the expression of a PDAT encoding gene.

Alternatively expression of PDC may be combined with expression of ACS and/or ALD thus providing the combinations PDC+ALD, PDC+ACS and PDC+ALD+ACS. These combinations may be expressed with or without further expressing a gene encoding DAT, such as PDAT.

"Fungal" "fungus" and "fungi" as used herein refers to yeast and filamentous fungi i.e. moulds. A genetically modified fungal cell is also referred to as host cell.

The yeast host cell may be selected for example from the genera *Cryptococcus, Candida, Galactomyces, Hansenula, Lipomyces, Rhodosporidium, Rhodotorula, Trichosporon* and *Yarrowia*. Preferably the yeast host cell is selected from the group consisting of *Candida* sp., *Cryptococcus curvatus, Cryptococcus albidus, Galactomyces geotrichurn, Hansenula ciferri, Lipomyces lipofer, Lipomyces* ssp., *Lipomyces starkeyi, Lipomyces tetrasporus, Rhodosporidium toruloides, Rhodotorula glutinis, Trichosporon pullulans* and *Yarrowia lipolytica*. In one embodiment the yeast is selected from the phylum *Basidiomycota*, which includes *Cryptococcus, Rhodotorula* and *Rhodosporidiurn*. Most preferably it is *Cryptococcus curvatus*.

The filamentous fungus host cell may be selected from the genera *Aspergillus, Cunninghamella, Fusarium, Glomus, Humicola, Mortierella, Mucor, Penicillium, Pythium* and *Rhizopus*. Preferably the filamentous fungus is selected from the group consisting of *Aspergillus nidulans, Aspergillus oryzae, Aspergillus terreus, Aspergillus niger, Cuninghamella japonica, Fusarium oxysporum, Glomus caledonius, Humicola lanuginose, Mortierella isabellina, Mortierella pusilla, Mortierella vinacea, Mucor circinelloides, Mucor*

*plumbeus, Mucor ramanniana, Penicillium lilacinum, Penicillium spinulosum, Pythium ultimum* and *Rhizopus oryzae*. According to one embodiment the filamentous fungus belongs to subphylum Mucoromycotina, which includes *Mucor* and *Mortierella*. Most preferably it is *Mucor circinelloides*.

According to one preferred embodiment the fungal host cell is an oleaginous fungus. The term "Oleaginous fungi" refers to yeasts or filamentous fungi, which accumulate at least 10%, 12.5%, 15%, 17.5%, preferably at least 20% or even at least 25% (w/w) of their biomass as lipid. They may even accumulate at least 30%, 40%, 50%, 60%, 70%, 80% (w/w) or more of their biomass as lipids. The biomass is usually measured as cell dry weight (CDW). Oleaginous fungi are found e.g. in genera *Cryptococcus, Candida, Galactomyces, Hanseluna, Lipomyces, Rhodosporidium, Rhodotorula, Trichosporon, Yarrowia, Aspergillus, Cunninghamella, Fusarium, Glomus, Humicola, Mortierella, Mucor, Penicillium, Pythium* and *Rhizopus*, and especially in species *Candida* sp., *Cryptococcus curvatus, Cryptococcus albidus, Galactomyces geotrichum, Hansenula ciferri, Lipomyces lipofer, Lipomyces* ssp., *Lipomyces starkeyi, Lipomyces tetrasporus, Rhodosporidium toruloides, Rhodotorula glutinis, Trichosporon pullulans, Yarrowia lipolytica, Aspergillus nidulans, Aspergillus oryzae, Aspergillus terreus, Aspergillus niger, Cuninghamella japonica, Fusarium oxysporum, Glomus calcdonius, Humicola lanuginose, Mortierella isabellina, Mortierella pusilla, Mortierella vinacea, Mucor circinelloides, Mucor plumbeus, Mucor ramanniana, Penicillium lilacinum, Penicillium spinulosum, Pythium ultimum* and *Rhizopus oryzae*. In one embodiment it is a Crabtree-negative oleaginous yeast, and in another embodiment it is a Crabtree-positive filamentous fungus. In still another embodiment the filamentous fungus is Crabtree-negative, or the yeast is Crabtree-positive. *Saccharomyces* yeasts including *S. cerevisiae* are not oleaginous fungi. A "Crabtree-positive" organism is one that is capable of producing ethanol in the presence of oxygen, whereas a "Crabtree-negative" organism is not.

According to one preferred embodiment the host cell is a *Cryptococcus*, and especially *Cryptococcus curvatus*. Genetically modified *Cryptococcus curvatus* strains have not been described in literature (Meesters et al. 1997). Routinely, in yeast expression systems *S. cerevisiae* promoters and terminators, original genes without codon optimisation or codon-optimised for *S. cerevisiae* are used. In this invention we showed that it is possible to express genes successfully in *C. curvatus* when using endogenous promoters and terminators i.e. which originate from the species wherein the expression cassette will be transformed, and an expressed gene that is codon-optimised according to codon usage of the species wherein the expression cassette will be transformed, or its close relative, which has a genome that is known at a level where codon-optimisation is possible. Such a close relative is e.g. *Ustilago maydis*. In a preferred embodiment the promotors are constitutive promotors, especially from the glycolysis pathway.

Promoters and terminators of oleaginous fungi might contain sites for different regulatory elements and transcription factors than the promoters and terminators of *S. cerevisiae* due to the different nature of the strains: *S. cerevisiae* can grow and produce ethanol under anaerobic conditions whereas *C. curvatus* does not produce ethanol at all, and lipids it produces under aerobic conditions. Also the codon usage differs in *S. cerevisiae* and in *C. curvatus*: E.g. *S. cerevisiae* codons and genome are adenine and thymine rich, whereas the ratio of guanine and cytosine is much higher in *C. curvatus* (Meesters et al. 1997).

It is also important to use endogenous promoters and terminators with resistance markers to detect transformants after transformations. Due to the fact that the genome of *C. curvatus* is not known different procedures described in this invention can be carried out to clone endogenous promoters and terminators. Preferably constitutive promoters are used.

The fungal cell can be genetically modified by transforming it with a heterologous nucleic acid that encodes a heterologous protein. "Heterologous" in this context means not naturally occurring. In one embodiment, the cell is transformed with a heterologous nucleic acid that encodes at least one of PDC, ALD and ACS, and a heterologous nucleic acid comprising a nucleic acid that encodes DAT, operably linked to allow expression of the genes encoding said enzymes. DNA isolation, enzymatic treatment and genetical modifications may be carried out using standard molecular biology methods as described e.g. Sambrook and Russell (2001). The promoter and terminator regions of the genes of interest can be cloned e.g. from a yeast or filamentous fungus strain of interest by polymerase chain reaction (PCR) using gene specific oligonucleotides designed based on known published gene sequences of strains of the same species or other species or gene sequences of the strain of interest. Oligonucleotides designed based on the sequence of the strain of interest are preferred.

New gene fragments from yeast and filamentous fungus species or strains with unknown genomic sequences can be cloned by PCR by using degenerative primers. The term "degenerative primer" refers to mixtures of similar kinds of synthesized primers differing from each other by one nucleotide. Degenerative primers for cloning of specific gene fragments from desired species or strains are designed based on known characterised or putative gene sequences.

A person skilled in art can use known characterised gene sequences as templates in a Blast search to find out other characterised or putative gene sequences. Another possibility is to search specific gene sequences by enzymes names from databases containing genomic sequences of species from different genome sequencing projects. These kinds of databases are found for example, but not excluding, in Broad Institute's Fungal Genome Initiative sequence projects. In the searches of specific gene sequences species that are closely related to the yeast and filamentous fungus species of interest are preferred. After a set of specific gene sequences has been found nucleotide sequence alignments are carried out with appropriate programs e.g. Clustal W, resulting in a consensus sequence, which is used in designing degenerative primers. Designed degenerative primers are used in a PCR reaction with DNA of the yeast or filamentous fungus strain of interest as a template. Resulting PCR fragments are gel isolated and sequenced directly or after being cloned into plasmids. Detected sequences are used in Blast searches to confirm that right gene fragments have been cloned.

An unknown promoter and/or terminator region of a gene of interest can be cloned by a chromosome walking method. The term "chromosome walking" refers to sequential isolation of clones carrying overlapping sequences of a known gene region and an unknown sequence of an adjacent gene region produced by ligation-mediated PCR amplification method (Mueller and Wold 1989). Gene specific oligonucleotides corresponding to a known sequence of a gene of interest are designed and used in PCR reactions with linker specific oligonucleotides. The known sequence of the gene of interest may originate e.g. from a sequence of a gene fragment generated in a PCR reaction with degenerative oligos or from a gene sequence published in sequence databases. The resulting PCR fragments are gel isolated and sequenced directly or after being cloned into plasmids. Detected sequences are used in Blast searches to confirm that right gene fragments have been cloned. If needed, the chromosome walking experiment will be repeated so many times that desired length of promoter or terminator region has been cloned. The existence of the sequence of the promoter or terminator region of the desired gene is confirmed by usual bioinformatics methods e.g. with multiple sequence alignment.

A strain specific gene fragment containing the promoter and/or terminator region of the gene of interest can also be cloned by conventional library screening methods described e.g. in Sambrook and Russell (2001). The sequences of the oligonucleotides used in PCR reactions to clone desired promoter or terminator regions can also contain sequences of restriction sites of specific restriction enzymes in addition to the gene specific sequence. The PCR fragment containing the desired promoter or terminator will be cloned into plasmid e.g. pBluescript and sequenced.

Promoters used in expression cassettes can be promoters of constitutively expressed genes e.g. of 3-phosphoglycerate dehydrogenase (PGK), triose phosphate isomerase (TPI) or enolase (ENO). Alternatively, the promoter used in the expression cassette can be a promoter of a gene, which is expressed under specific cultivation conditions.

"Expression cassette" as used herein refers to a nucleic acid construct that comprises a transcription initiation or transcription control sequence, e.g. a promotor, operably linked to a coding region for the protein to be transcribed, and preferably a transcription termination region. In addition it conveniently comprises one or more marker regions, i.e. regions encoding a selection marker.

Genes to be expressed can be cloned directly from the desired species or strains by conventional molecular biology methods e.g. by using PCR. More preferably the genes to be expressed are synthesised using a codon optimised nucleotide sequence based on the known codon usage of the host strain. If the codon usage of the host strain or host species is not known, the gene to be expressed can be codon optimised based on the known codon usage of a closely related species of the host strain. Alternatively, the gene to be expressed can be synthesised according to a known amino acid sequence by translating the amino acid sequence into a DNA sequence, preferably into a codon-optimised DNA sequence. The term "codon optimization" refers to an optimization of a synthetic nucleotide sequence encoding expressed genes to enhance gene product production in a host strain. Codon optimization can occur by replacing existing codons of the original gene by the codons used more often in the host strain. In codon optimisation also internal TATA-boxes, chisites, ribosomal entry sites, AT-rich or GC-rich sequence stretches, repeated sequences, RNA secondary structures and cryptic splice donor and acceptor sites can be avoided. Additionally in codon optimisation sequences of restriction sites of specific restriction enzymes can be avoided. Preferably, in a synthesised gene sequence the CTG codon will be avoided due to its different coding in different fungi (leucine or serine).

A nucleic acid that is "degenerate as a result of the genetic code" to a given sequence, means that it contains one or more different codons, but encodes for the same amino acids. A "polynucleotide" as used herein may be a single or double stranded polynucleic acid. The term encompasses genome DNA, cDNA and RNA.

A "synthetic gene" or "synthetic nucleotide sequence" is an artificially designed gene or sequence, which has been synthesised into a physical DNA sequence.

The gene to be expressed is cloned between a promoter and terminator. An expression cassette of the gene to be expressed with promoter and terminator, and a marker gene can be transformed. The marker gene can be under its own promoter and terminator, but preferably it is under a functional promoter and terminator from another species, or more preferably under a functional promoter and terminator of the host strain. Markers to be used can be antibiotic markers like genes for hygromycin, geneticin and cerulenin resistances or other dominant marker like the melibiase gene. Additionally genes of the amino acid synthesis can be used as markers with auxotrophic fungi. The gene to be expressed can be transformed into the yeast or filamentous fungus as a plasmid to produce epitopic transformants, or as a DNA fragment containing the expression cassette to produce transformants with the expression cassette integrated into the genome of the host strain.

Expression cassettes containing the marker gene and gene to be expressed can be transformed in the same DNA fragment, or the expression cassettes of marker gene and gene to be expressed can be in separate DNA fragments. Transformation methods contain chemical, protoplast, electroporation methods. Transformants can be selected based on their ability to grow on a medium (solid or liquid) containing antibiotics, or a medium lacking some essential component e.g. an amino acid, or transformants can be selected based on different phenotype such as colour reaction of the transformants in specific conditions.

The DNA level of the transformants can be characterised by PCR or by Southern analysis using conventional molecular biology methods. Additionally enzyme activities of the expressed gene can be assayed as indicated in the example 27 or as described e.g. in Dahlqvist et al. 2000 and Postma et al. 1989.

The gene to be expressed can be an endogenous gene, whereby the promoter region can be replaced with a promoter of a constitutively expressed gene, or with a promoter of a gene, which is expressed under specific cultivation conditions. Additionally, expression of an endogenous gene can be enhanced by classical mutagenesis.

The genetically modified fungi of the present invention are capable of producing increased levels of lipids, and especially of triacylglycerols. The increase may be at least a 1.5, 3, 5 or 10 fold increase in lipid or triacylglycerol concentration in transformants compared to the unmodified host strain during cultivation. Alternatively, it may be at least a 1.5, 3, 5 or 10 fold increase in lipid or triacylglycerol yield per used carbon source (e.g. glucose) in transformants compared to the unmodified host strain. It may also refer to a 1.5, 3, 5 or 10 fold increase in lipid or triacylglycerol production rate (mg/l/h) compared to the unmodified host strain. This increase in lipid or triacylglycerol production can be detected either intracellularly or in the amount of lipids and triacylglycerols in culture medium.

The genetically modified fungi are cultivated in a medium containing appropriate carbon and nitrogen sources together with other optional ingredients like yeast extract, peptone, minerals and vitamins, such as $KH_2PO_4$, $Na_2HPO_4$, $MgSO_4$, $CaCl_2$, $FeCl_3$, $ZnSO_4$, citric acid, $MnSO_4$, $CoCl_2$, $CuSO_4$, $Na_2MoO_4$, $FeSO_4$, $H_3BO_4$, D-biotin, CaPantothenate, nicotinic acid, myoinositol, thiamine, pyridoxine, p-aminobenzoic acid. The invention works at a wide range of C/N ratios about from 20 to 160 under microaerobic (50 ml medium in 250 ml flask with 100 rpm shaking) and aerobic (50 ml medium in 250 ml flask with 250 rpm shaking or 1-2 vvm in bioreactors) conditions from the beginning of the cultivation to the end of cultivation as far as up to at least 8 days. The host cells used are preferably such that are able not only to use hexoses, such as glucose, but also pentoses such as xylose, and arabinose, or even glycerol as carbon source. Preferably the carbon source is a hexose and/or pentose sugars containing material such as cellulose or hemicellulose. The genetically modified host cells are preferably grown on agricultural or industrial waste materials e.g. cellulose or hemicellulose containing materials, which makes the lipid production economically and environmentally beneficial.

After cultivation, the yeast or filamentous fungal cells are normally separated from the culture medium. Lipids are recovered from the cells typically by using non-polar organic solvents, such as hexane. Prior to extraction, cells can be dried and/or disrupted. Alternatively, the lipids can be recovered directly from the culture medium, which of course is an advantage. This is especially convenient when the host cell is *Cryptococcus*, such as *C. curvatus*. Preferably lipid extraction is carried out to obtain lipids which mainly contain triacylglycerol (TAG). The lipid fraction can also contain mono- and diglycerides, free fatty acids, phospholipids, glycolipids and other lipids.

The lipids, and especially the TAG and the fatty acids, obtained can be used for preparing biofuels and lubricants. Said lipids may be directly used as biofuel or lubricant, but usually they are further processed to e.g. biodiesel or renewable diesel and/or lubricant formulations. "Biofuel" as used herein refers to fuel that has been at least partially biologically produced.

"Biodiesel" consists essentially of fatty acid methyl esters and is typically produced by transesterification in which the acylglycerides are converted to fatty acid methyl esters. According to EU directive 2003/30/EU biodiesel refers to a methyl-ester produced from vegetable oil or animal oil, of diesel quality to be used as biofuel. More broadly, biodiesel refers to long-chain alkyl esters, such as methyl, ethyl or propyl esters, from vegetable oil or animal fat of diesel quality. In the present content biodiesel can also be produced from fungal lipids.

"Renewable diesel" refers to fuel which is produced by hydrogen treatment (hydrogenation or hydroprocessing) of lipids of animal, vegetable or fungal origin, or their mixtures. Renewable diesel can be produced also from waxes derived from biomass by gasification and Fischer-Tropsch synthesis. Optionally, in addition to hydrogen treatment, isomerization or other processing steps can be performed. In hydrogen treatment, acylglycerides are converted to corresponding alkanes (paraffins). The alkanes (paraffins) can be further modified by isomerization or by other process alternatives. These processes can also produce hydrocarbons which are suitable for jet fuel or gasoline applications.

"Lubricant" refers to a substance, such as grease, lipid or oil that reduces friction when applied as a surface coating to moving parts. Two other main functions of a lubricant are heat removal and dissolving impurities. Applications of lubricants include, but are not limited to uses in internal combustion engines as engine oils, additives in fuels, in oil-driven devices such as pumps and hydraulic equipment, or in different types of bearings. Typically lubricants contain 75-100% base oil and the rest is additives. In the present invention at least part of the base oil is of fungal origin. Viscosity index is used to characterise base oil. Typically high viscosity index is preferred.

Lubricants or at least the base oil for lubricants may be prepared in the same way as described above for the biofuels. Usually conventional additives such as viscosity modifyers, antioxidants, pour point modifyers etc. are added to the base oil to obtain the lubricant.

The lipids, and especially the TAG and the fatty acids obtained can also be used for precursors for functional fatty acids. Said lipids are further processed to release fatty acyls which can be used in the production of functional fatty acids, like dicarboxylic acids and epoxides, which can be further converted into products like polyesters, polyurethane, coatings and resins.

The following examples are provided to illustrate the invention, but are not intended to limit the scope thereof. The enzyme names used are based on sequence homology.

Example 1A

Cloning of *Cryptococcus curvatus* TEF (CcTEF1) Promoter and Terminator Region

A genomic ~800 bp fragment of the *C. curvatus* TEF gene was amplified by PCR with degenerate primers identified as SEQ ID NO:1 (Yeast TEF1), and SEQ ID NO:2 (Yeast TEF4), using *C. curvatus* (C-01440, VTT Culture Collection) genomic DNA as the template. The degenerative primers were designed based on a consensus sequence of the putative TEF1 genes of *Ustilago maydis, Candida guilliermondii* and *Candida tropicalis*. The detected genomic fragment was sequenced.

Genomic fragments containing the CcTEF1 promoter region were obtained with ligation-mediated PCR amplification (Mueller, P. R. and Wold, B. 1989). A mixture of a linker identified as SEQ ID NO:3 (PCR linker I), and a linker identified as SEQ ID NO:4 (PCR linker II) was ligated to PvuII digested *C. curvatus* genomic DNA with T4 DNA ligase (New England BioLabs). Samples of the ligation mixtures were used as templates for 50 µl PCR reactions containing 0.1 µM of a primer identified as SEQ ID NO: 3 (PCR linker I), and 1 µM of a primer identified as SEQ ID NO:5 (CC_TEF2). The reaction mixture was heated at 94° C. for 3 minutes after 2 U of Dynazyme EXT was added. The reactions were cycled 30 times as follows: 1 minute at 94° C., 2 minutes at 60° C. and 2 minutes at 72° C., with final extension of 10 minutes at 72° C. A diluted sample of this first PCR-amplification was used as the template in a nested PCR reaction (50 µl) containing 0.05 µM of a primer identified as SEQ ID NO:3 (PCR Linker I), and 0.5 µM of a primer identified as SEQ ID NO:6 (CC_TEF1). The reaction mixture was heated at 94° C. for 3 minutes after 2 U of Dynazyme EXT was added. The reactions were then cycled 30 times as follows: 1 minute at 94° C., 2 minutes at 60° C. and 2 minutes at 72° C., with final extension of 10 minutes at 72° C.

A ~800 bp fragment was isolated and sequenced. Nested primers identified as SEQ ID NO:7 (CC_TEF6), and SEQ ID NO:8 (CC_TEF5) were designed and used in a ligation-mediated PCR amplification together with oligonucleotides identified as SEQ ID NO:3 (PCR linker I), and a linker identified as SEQ ID NO:4 (PCR linker II) similarly as above except that NruI-digested *C. curvatus* DNA was used. A ~2000 bp PCR fragment was isolated and sequenced.

The *C. curvatus* TEF1 promoter was PCR amplified using primers identified as SEQ ID NO:9 (CC_TEF10), and SEQ ID NO:10 (CC_TEF11) and the *C. curvatus* genomic DNA as the template. A PCR fragment was digested with SacII and XbaI. A 1276 bp fragment was gel isolated and ligated to a SacII and XbaI-digested pBluescript KS-plasmid (Stratagene). The resulting plasmid was designated pKK58. Plasmid pKK58 contains *C. curvatus* TEF1 promoter.

A genomic fragment containing the CcTEF1 terminator region was obtained with a ligation-mediated PCR amplification with *C. curvatus* TEF1 gene specific oligonucleotides identified as SEQ ID NO:11 (CC_TEF3), and SEQ ID NO:12 (CC_TEF4) together with oligonucleotides identified as SEQ ID NO:3 (PCR Linker I) and SEQ ID NO:4 (PCR Linker II) similarly as above except that NruI-digested *C. curvatus* DNA was used. A ~1600 bp PCR fragment was isolated and sequenced.

The *C. curvatus* TEF1 terminator was PCR amplified using primers identified as SEQ ID NO:13 (CC_TEF7) and SEQ ID NO:14 and the *C. curvatus* genomic DNA as the template. A PCR fragment was digested with XmaI and EcoRI. A 358 bp fragment was gel isolated and ligated to XmaI and EcoRI-digested pBluescript KS-plasmid. The resulting plasmid was designated pKK55. Plasmid pKK55 contains the *C. curvatus* TEF1 terminator.

Example 1B

Cloning of *Cryptococcus curvatus* TPI (CcTPI1) Promoter and Terminator Region

A genomic fragment of the *C. curvatus* TPI1 gene was amplified by PCR from genomic *C. curvatus* (C-01440, VTT Culture Collection) DNA with degenerative primers identified as SEQ ID NO:15 (Yeast TPI5), and SEQ ID NO:16 (Yeast TPI8). The degenerative primers were designed based on a consensus sequence of the TPI1 genes of *Ustilago maydis* and *Cryptococcus neoformans*. A ~800 bp genomic fragment was isolated and sequenced.

A genomic fragment containing the CcTPI1 promoter region was obtained with a ligation-mediated PCR amplification with TPI1 gene specific oligonucleotides identified as SEQ ID NO:17 (CC_TPI2), and SEQ ID NO:18 (CC_TPI1), together with oligonucleotides identified as SEQ ID NO:3 (PCR Linker I) and SEQ ID NO:4 (PCR Linker II), similarly as in Example 1A except that EcoRV-digested *C. curvatus* DNA was used. A ~1300 bp PCR fragment was isolated and sequenced.

The *C. curvatus* TPI1 promoter was PCR amplified by using primers identified as SEQ ID NO:19 (CC_TPI7) and SEQ ID NO:20 (CC_TPI_9) and the *C. curvatus* DNA as the template. A PCR fragment was digested with BamHI and SbfI. A 851 bp fragment was gel isolated and ligated to a BamHI and PstI-digested pBluescript KS-plasmid. The resulting plasmid was designated pKK63. Plasmid pKK63 contains the *C. curvatus* TPI1 promoter.

A genomic fragment containing the CcTPI1 terminator region was obtained with a ligation-mediated PCR amplification with TPI1 gene specific oligonucleotides identified as SEQ ID NO:21 (CC_TPI 4) and SEQ ID NO:22 (CC_TPI3), together with oligonucleotides identified as SEQ ID NO:3 (PCR Linker I) and SEQ ID NO:4 (PCR Linker II), similarly as in Example 1A except that EcoRV-digested *C. curvatus* DNA was used. A ~1200 bp PCR fragment was isolated and sequenced.

The *C. curvatus* TPI1 terminator was PCR amplified by using primers identified as SEQ ID NO:23 (CC_TPI5) and SEQ ID NO:24 (CC_TPI6) and the *C. curvatus* genomic DNA as the template. A PCR fragment was digested with XbaI and BamHI. A 361 bp fragment was gel isolated and ligated to a XbaI and BamHI—digested pBluescript KS—plasmid. The resulting plasmid was designated pKK61. Plasmid pKK61 contains *C. curvatus* TPI1 terminator.

Example 1C

Cloning of *Cryptococcus curvatus* ENO (CcENO1) Promoter and Terminator Region

A genomic fragment of the *C. curvatus* ENO1 gene was amplified by PCR from genomic *C. curvatus* (C-01440, VTT Culture Collection) DNA with degenerative primers identified as SEQ ID NO:25 (YeastENO5) and SEQ ID NO:26 (YeastENO10). The degenerative primers were designed based on a consensus sequence of ENO1 genes of *Ustilago maydis* and *Cryptococcus neoformans*. A ~1000 bp genomic fragment was isolated and sequenced.

A genomic fragment containing the CcENO1 promoter region was obtained with a ligation-mediated PCR amplification with ENO1 gene specific oligonucleotides identified as SEQ ID NO:27 (CC_ENO2) and SEQ ID NO:28 (CC_ENO1), together with oligonucleotides identified as SEQ ID NO:3 (PCR Linker I) and SEQ ID NO:4 (PCR Linker II), similarly as in Example 1A except that PvuII-digested *C. curvatus* DNA was used.

A ~600 bp fragment was isolated and sequenced. Nested primers identified as SEQ ID NO:29 (CC_ENO5) and SEQ ID NO:30 (CC_ENO6) were designed and used in a ligation-mediated PCR amplification together with oligonucleotides identified as SEQ ID NO:3 (PCR Linker I) and SEQ ID NO:4 (PCR Linker II) similarly as above except that SspI-digested *C. curvatus* DNA was used. A ~2000 bp PCR fragment was isolated and sequenced.

The *C. curvatus* ENO1 promoter was PCR amplified by using primers identified as SEQ ID NO:31 (CC_ENO9) and SEQ ID NO:32 (CC_ENO10) and the *C. curvatus* genomic DNA as the template. A PCR fragment was digested with EcoRI. A 1214 bp fragment was gel isolated and ligated to a EcoRI-digested pBluescript KS-plasmid. The resulting plasmid was designated pKK74. Plasmid pKK74 contains the *C. curvatus* ENO1 promoter.

A genomic fragment containing the CcENO1 terminator region was obtained with a ligation-mediated PCR amplification with ENO1 gene specific oligonucleotides identified as SEQ ID NO:33 (CC_ENO4) and SEQ ID NO:34 (CC_ENO3), together with oligonucleotides identified as SEQ ID NO:3 (PCR Linker I) and SEQ ID NO:4 (PCR Linker II), similarly as in Example 1A except that NruI-digested *C. curvatus* DNA was used. A ~1100 bp PCR fragment was isolated and sequenced.

The *C. curvatus* ENO1 terminator was PCR amplified by using primers identified as SEQ ID NO:35 (CC_ENO7) and SEQ ID NO:36 (CC_ENO8), and the *C. curvatus* genomic DNA as the template. A PCR fragment was digested with HindIII. A 375 bp fragment was gel isolated and ligated to a HindIII-digested pBluescript KS-plasmid. The resulting plasmid was designated pKK60. Plasmid pKK60 contains the *C. curvatus* ENO1 terminator.

Example 1D

Cloning of *C. curvatus* GPD (CcGPD1) Terminator Region

A genomic fragment containing the CcGPD1 terminator region was obtained with a ligation-mediated PCR amplification with GPD1 gene specific oligonucleotides identified as SEQ ID NO:37 (CC_GPD3) and SEQ ID NO:38

(CC_GPD4), together with oligonucleotides identified as SEQ ID NO:3 (PCR Linker I) and SEQ ID NO:4 (PCR Linker II), similarly as in Example 1A except that SspI-digested *C. curvatus* DNA was used. A ~1800 bp fragment was isolated and partially sequenced. GPD1 gene specific oligonucleotides were designed according to the *C. curvatus* GPD1 gene (GenBank Accession number AF126158, version number AF126158.1) sequence.

The *C. curvatus* GPD1 terminator was PCR amplified by using primers identified as SEQ ID NO:39 (CC_GPD6) and SEQ ID NO:40 (CC_GPD7), and the *C. curvatus* genomic DNA as the template. A PCR fragment was digested with XbaI and BamHI. A 336 bp fragment was gel isolated and ligated to a XbaI and BamHI-digested pBluescript KS-plasmid. The resulting plasmid was designated pKK54. Plasmid pKK54 contains *C. curvatus* GPD1 terminator.

Example 2A

Cloning of the *E. coli* Hygromycin Resistance Gene; Construction of a Plasmid (pKK76) Having the *E. coli* Hygromycin Resistance Gene Under the Control of the CcTEF1 Promoter and the CcTPI1 Terminator The *E. coli* hygromycin (hph) gene, that confers resistance to hygromycin B, was PCR amplified using primers identified as SEQ ID NO:41 (Hph 5) and SEQ ID NO:42 (Hph 3), and the plasmid pRLMEX30 (Mach et al. 1994) DNA as the template. A PCR fragment was digested with SpeI. A 1048 bp fragment was gel isolated and ligated to SpeI-digested pBluescript KS-plasmid and sequenced. The resulting plasmid was designated pKK52.

Plasmid pKK58 was digested with SacII and SbfI. A 1272 bp fragment was gel isolated. Plasmid pKK52 was digested with SbfI. A 1034 bp fragment was gel isolated. Plasmid pKK58 contains the *C. curvatus* TEF1 promoter and plasmid pKK61 contains the *C. curvatus* TPI1 terminator. The 1272 bp fragment originating from plasmid pKK58 and the 1034 bp fragment originating from the pKK52 plasmid were ligated to a 3285 bp fragment obtained by digesting a plasmid designated as pKK61 with SacII and SbfI. The resulting plasmid was designated pKK76. Plasmid pKK76 contains the *E. coli* hygromycin gene under the control of the *C. curvatus* TEF1 promoter and the *C. curvatus* TPI1 terminator.

Example 2B

Cloning of the *E. coli* G418 Resistance Gene; Construction of a Plasmid (pKK67) Having the *E. coli* Geneticin Resistance Gene Under the Control of the CcTEF1 Promoter and the CcTPI1 Terminator The *E. coli* G418 resistance gene was PCR amplified using primers identified as SEQ ID NO:43 (Kan 5) and SEQ ID NO:44 (Kan 3), and the plasmid pPIC9K (Invitrogen) DNA as the template. A PCR fragment was digested with SpeI. A 838 bp fragment was gel isolated and ligated to SpeI-digested pBluescript KS-plasmid and sequenced. The resulting plasmid was designated pKK51.

Plasmid pKK58 was digested with SacII and SbfI. A 1272 bp fragment was gel isolated. Plasmid pKK51 was digested with SbfI. A 824 bp fragment was gel isolated. The 1272 bp fragment originating from pKK58 plasmid and the 824 bp fragment originating from pKK51 plasmid were ligated to a 3285 bp fragment obtained by digesting a plasmid designated pKK61 with SacII and SbfI. Plasmid pKK58 contains the *C. curvatus* TEF1 promoter and plasmid pKK61 contains the *C. curvatus* TPI1 terminator. The resulting plasmid was designated pKK67. Plasmid pKK67 contains the *E. coli* G418 resistance gene under the control of the *C. curvatus* TEF1 promoter and the *C. curvatus* TPI1 terminator.

Example 2C

Cloning of *S. cerevisiae* Cerulenin Resistance Gene; Construction of a Plasmid (pKK91) Having the *S. cerevisiae* Cerulenin Resistance Gene Under the Control of the CcTEF1 Promoter and the CcTPI1 Terminator The *S. cerevisiae* cerulenin resistance gene was PCR amplified using primers identified as SEQ ID NO:45 (CERR 5) and SEQ ID NO:46 (CERR 3), and the plasmid pSH47Y DNA as the template. Plasmid pSH47Y contains the cerulenin resistance gene from the plasmid pCR1 (Nakazawa et al. 1993). A PCR fragment was digested with SbfI. A 1685 bp fragment was gel isolated and ligated to PstI-digested pBluescript KS-plasmid and sequenced. The resulting plasmid was designated pKK80.

Plasmid pKK80 was digested with PstI. A 1685 bp fragment was gel isolated and ligated to a 4557 bp fragment obtained by digesting a plasmid designated as pKK67 with SbfI. Plasmid pKK67 contains the *E. coli* G418 resistance gene linked to a *C. curvatus* TEF1 promoter and *C. curvatus* TEF1 terminator. The resulting plasmid was designated pKK91. Plasmid pKK91 contains the *S. cerevisiae* cerulenin resistance gene under the control of the *C. curvatus* TEF1 promoter and the *C. curvatus* TPI1 terminator.

Example 3A

Construction of a Plasmid (pKK81, FIG. 3) Containing the Hygromycin Resistance Gene Under the Control of the CcTEF1 Promoter and the CcTPI1 Terminator and the *S. cerevisiae* ALD6 Encoding Gene Under the Control of the CcENO1 Promoter and the CcTEF1 Terminator The plasmid UmALD (Geneart AG, Germany) contains a *S. cerevisiae* ALD6 (SEQ ID NO:47) encoding gene which has been codon optimized according to *Ustilago maydis* yeast codon usage (SEQ ID NO:48) with flanking SbfI restriction sites. The plasmid RoALD (Geneart AG, Germany) contains a *S. cerevisiae* ALD6 (SEQ ID NO:47) encoding gene which has been codon optimized according to *Rhizopus oryzae* filamentous fungus codon usage (SEQ ID NO:49) with flanking SbfI restriction sites and an *E. coli* kanamycin resistance gene. Plasmid UmALD was digested with SfiI. A 1554 bp fragment was gel isolated and ligated to a 2258 bp fragment obtained by digesting a plasmid RoALD with SfiI. The resulting plasmid was designated as pKK50. The plasmid pKK50 contains a *S. cerevisiae* ALD6 (SEQ ID NO:47) encoding gene which has been codon optimized according to *Ustilago maydis* yeast codon usage (SEQ ID NO:48) with flanking SbfI restriction sites and an *E. coli* kanamycin resistance gene.

Plasmid pKK74 was digested with EcoRI and SbfI. A 1204 bp fragment was gel isolated. Plasmid pKK55 was digested with EcoRI and SbfI. A 347 bp fragment was gel isolated. The 1204 bp fragment originating from plasmid pKK74 and the 347 bp fragment originating from plasmid pKK55 were ligated to a 2961 bp fragment obtained by digesting a plasmid designated pKK74 with EcoRI. Plasmid pKK74 contains *C. curvatus* ENO1 promoter and plasmid pKK55 contains *C. curvatus* TEF1 terminator. The resulting plasmid was designated as pKK77pre.

Plasmid pKK50 was digested with SbfI. A 1514 bp fragment was gel isolated and ligated to a 4517 bp fragment obtained by digesting plasmid pKK77pre with SbfI. The resulting plasmid was designated as pKK77. The plasmid pKK77 contains the *S. cerevisiae* ALD6 encoding gene under the control of the CcENO1 promoter and the CcTEF1 terminator.

Figure 3:
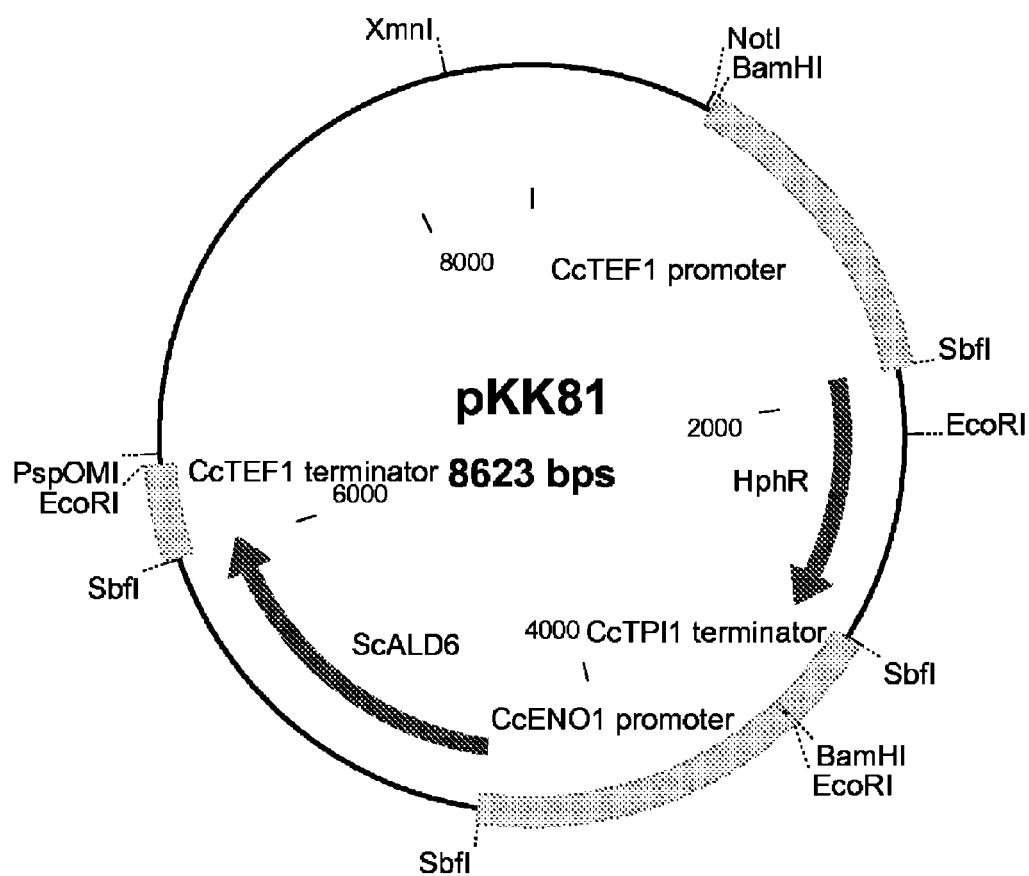
FIG. 3 is a diagram depicting plasmid pKK81.

Plasmid pKK76 was digested with BamHI and XmnI. A 2652 bp fragment was gel isolated and ligated to a 6031 bp fragment obtained by digesting plasmid pKK77 with BamHI. The plasmid pKK76 contains the *E. coli* hygromycin resistance gene under the control of the CcTEF1 promoter and the CcTPI1 terminator. The resulting plasmid was designated as pKK81 (FIG. 3).

Example 3B

Generation of a Genetically Modified *C. Curvatus* (Y23/81) with an Integrated ALD6 Encoding Gene and Hygromycin Resistance Gene by Transforming Wild-type *C. curvatus* with Digested Plasmid pKK81 (FIG. 3, Ex. 3A)

Plasmid pKK81 was restricted with NotI and PspOMI, and the resulting linear DNA was used to transform a wild-type *C. curvatus* strain ATCC 20509 designated as Y23 by electroporation using a standard electroporation method.

The transformed cells were screened for hygromycin resistance. Several hygromycin-resistant colonies were analysed at DNA level by PCR. The transformants originating from the transformation of *C. curvatus* with NotI and PspOMI cut pKK81 and containing a *S. cerevisiae* ALD6 encoding gene under the control of the CcENO1 promoter and the CcTEF1 terminator were designated as Y23/81-8, Y23/81-51, Y23/81-59, Y23/81-66 and Y23/81-69.

Example 4A

Construction of a Plasmid (pKK82, FIG. 4) Containing the G418 Resistance Gene Under the Control of the CcTEF1 Promoter and the CcTPI1 Terminator and the *S. cerevisiae* ALD6 Encoding Gene Under the Control of the CcENO1 Promoter and the CcTEF1 Terminator Plasmid pKK67 was digested with BamHI and XmnI. A 2442 bp fragment was gel isolated and ligated to a 6031 bp fragment obtained by digesting a plasmid pKK77 with BamHI. The plasmid pKK67 contains the *E. coli* G418 resistance gene under the control of the CcTEF1 promoter and the CcTPI1 terminator and the plasmid pKK77 contains *S. cerevisiae* ALD6 encoding gene under the control of the CcENO1 promoter and the CcTEF1 terminator. The resulting plasmid was designated as pKK82 (FIG. 4).

Example 4B

Figure 4:
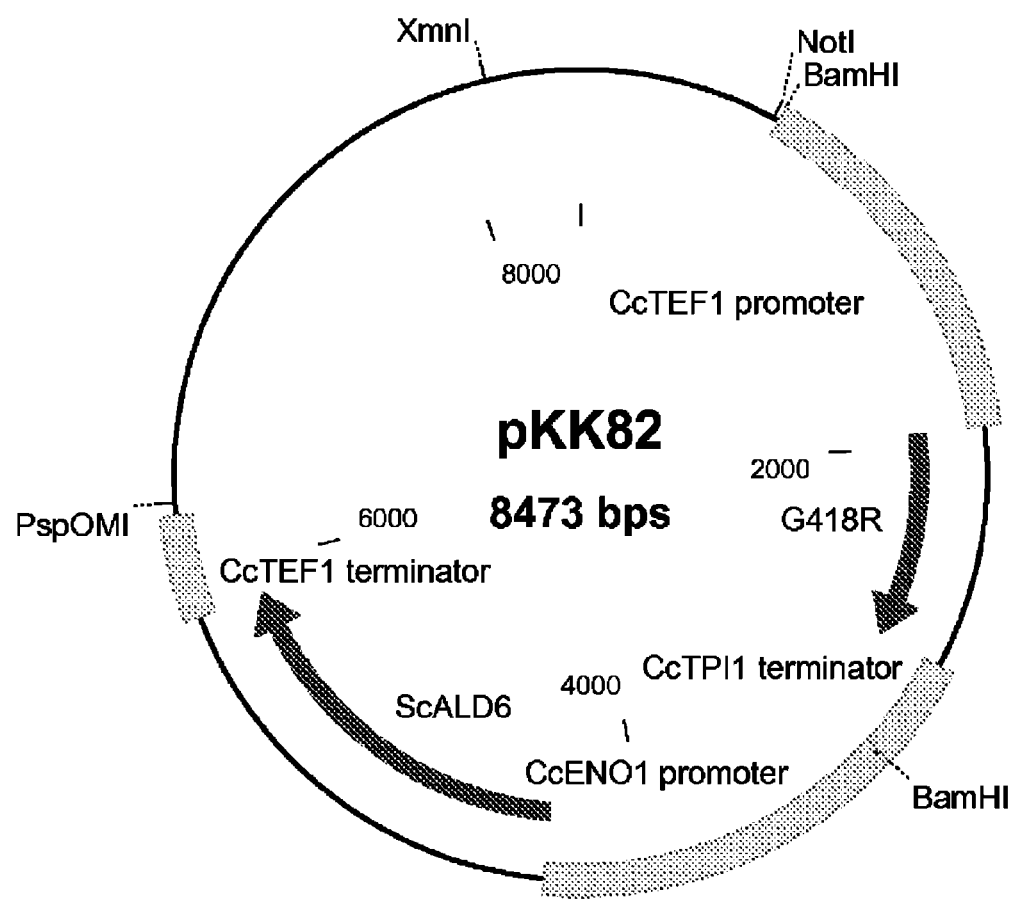
FIG. 4 is a diagram depicting plasmid pKK82.

Generation of a Genetically Modified *C. curvatus* (Y23/82) with an Integrated ALD6 Encoding Gene and G418 Resistance Gene by Transforming Wild-type *C. curvatus* with Digested Plasmid pKK82 (FIG. 4, Ex. 4A)

Plasmid pKK82 was restricted with NotI and PspOMI, and the resulting linear DNA was used to transform wild-type *C. curvatus* strain ATCC 20509 designated as Y23 by electroporation. The transformed cells were screened for G418 resistance. Several G418-resistant colonies were analysed at DNA level by PCR. The transformants originating from the transformation of *C. curvatus* with NotI and PspOMI cut pKK82 and containing *S. cerevisiae* ALD6 encoding gene under the control of the CcENO1 promoter and the CcTEF1 terminator were designated as Y23/82-1, Y23/82-2, Y23/82-4 and Y23/82-13.

Example 5A

Construction of a Plasmid (pKK86, FIG. 5) Containing the Hygromycin Resistance Gene Under the Control of the CcTEF1 Promoter and the CcTPI1 Terminator and the *S. cerevisiae* ACS2 Encoding Gene Under the Control of the CcTPI1 Promoter and the CcENO1 Terminator Plasmid pKK63 was digested with BamHI and SbfI. A 851 bp fragment was gel isolated and ligated to a 3295 bp fragment obtained by digesting plasmid pKK60 with BamHI and SbfI. The plasmid pKK63 contains the CcTPI1 promoter and the plasmid pKK60 contains the CcENO1 terminator. The resulting plasmid was designated as pKK78pre.

The plasmid UmACS contains the *S. cerevisiae* ACS2 (SEQ ID NO:50) encoding gene which has been codon optimized according to *Ustilago maydis* yeast codon usage (SEQ ID NO:51) with flanking SbfI restriction sites. Plasmid UmACS was digested with SbfI and DraI. A 2060 bp fragment was gel isolated and ligated to a 4146 bp fragment obtained by digesting plasmid pKK78pre with SbfI. The resulting plasmid was designated as pKK78.

Plasmid pKK76 was digested with BamHI and DraI. A 2652 bp fragment was gel isolated and ligated to a 6206 bp fragment obtained by digesting plasmid pKK78 with BamHI. The plasmid pKK76 contains the *E. coli* hygromycin resistance gene under the control of the CcTEF1 promoter and the CcTPI1 terminator. The resulting plasmid was designated as pKK86 (FIG. 5).

Example 5B

Figure 5:
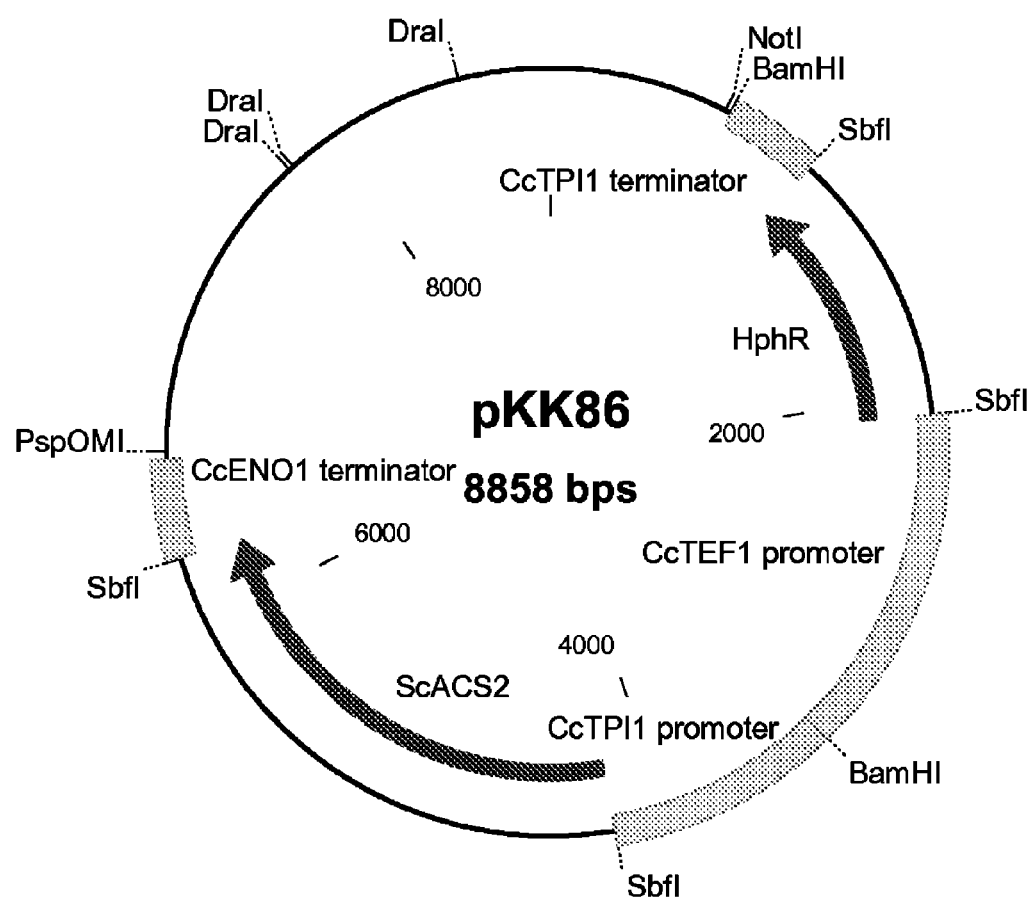
FIG. 5 is a diagram depicting plasmid pKK86.

Generation of a Genetically Modified *C. curvatus* (Y23/86) with an Integrated ACS2 Encoding Gene and Hygromycin Resistance Gene by Transforming Wild-Type *C. curvatus* with Digested Plasmid pKK86 (FIG. 5, Ex. 5A)

Plasmid pKK86 was restricted with NotI and PspOMI, and the resulting linear DNA was used to transform a wild-type *C. curvatus* strain ATCC 20509 designated as Y23 by electroporation. The transformed cells were screened for hygromycin resistance. Several hygromycin-resistant colonies were analysed at DNA level by PCR. The transformants originating from the transformation of *C. curvatus* with NotI and PspOMI cut pKK86 and containing *S. cerevisiae* ACS2 encoding gene under the control of the CcTPI1 promoter and the CcENO1 terminator were designated as Y23/86-86, Y23/86-92, Y23/86-93, Y23/86-98 and Y23/86-100.

Example 6A

Construction of a Plasmid (pKK95, FIG. 6) Containing the Cerulenin Resistance Gene Under the Control of the CcTEF1 Promoter and the CcTPI1 Terminator and the *R. oryzae* PDAT Encoding Gene Under the Control of the CcTPI1 Promoter and the CcGPD1 Terminator Plasmid pKK54 was digested with KpnI and SbfI. A 394 bp fragment was gel isolated and ligated to a 3742 bp fragment obtained by digesting plasmid designated as pKK63 with KpnI and SbfI. The plasmid pKK54 contains the CcGPD1 terminator and the plasmid pKK63 contains the CcTPI1 promoter. The resulting plasmid was designated as pKK93pre. Plasmid UmPDAT was digested with SbfI. A 1844 bp fragment was gel isolated and ligated to a 4136 bp fragment obtained by digesting plasmid pKK93pre with SbfI. The plasmid UmPDAT contains a *R. oryzae* PDAT (SEQ ID NO:52) encoding gene which has been codon optimized according to *U. maydis* yeast codon usage (SEQ ID NO:53) with flanking SbfI restriction sites. The resulting plasmid was designated as pKK93.

The plasmid pKK93 was digested with EcoRI and DraI. A 3029 bp fragment was gel isolated and ligated to a 6242 bp fragment obtained by digesting plasmid pKK91 with EcoRI. The plasmid pKK91 contains the *S. cerevisiae* cerulenin resistance gene under the control of the CcTEF1 promoter and the CcTPI1 terminator. The resulting plasmid was designated as pKK95 (FIG. 6).

Example 6B

Figure 6:
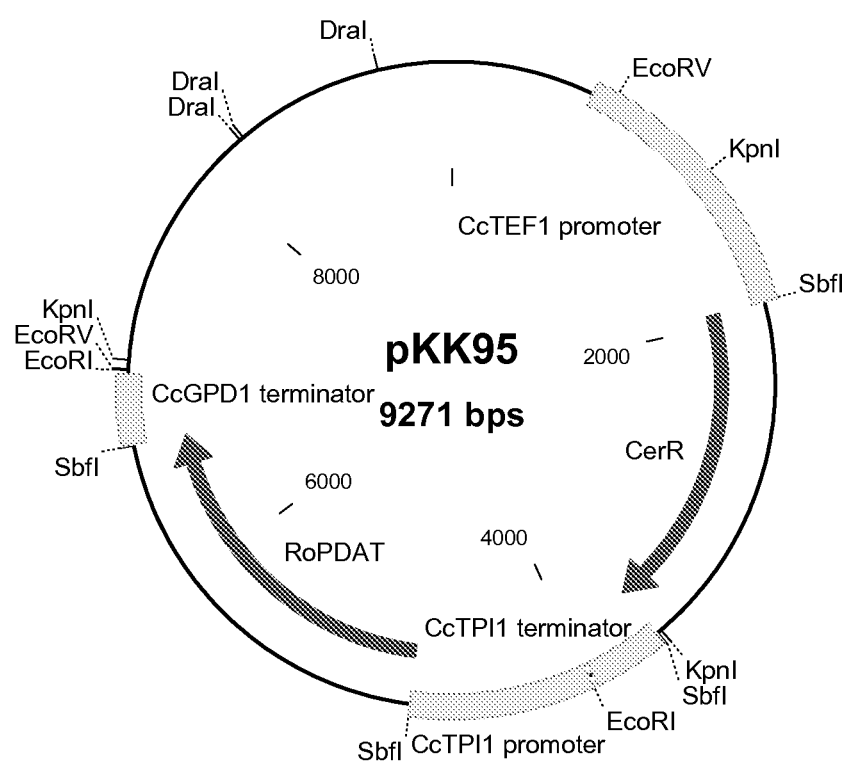
FIG. 6 is a diagram depicting plasmid pKK95.

Generation of a Genetically Modified *C. curvatus* (Y23/95) with an Integrated PDAT Encoding Gene and Cerulenin Resistance Gene by Transforming Wild-type *C. curvatus* with Digested Plasmid pKK95 (FIG. 6, Ex. 6A)

Plasmid pKK95 was restricted with EcoRV, and the resulting linear DNA was used to transform a wild-type *C. curvatus* strain ATCC 20509 designated as Y23 by electroporation. The transformed cells were screened for cerulenin resistance. Several cerulenin-resistant colonies were analysed at DNA level by PCR. The transformants originating from the transformation of *C. curvatus* with EcoRV cut pKK95 and containing the *R. oryzae* PDAT encoding gene under the control of the CcTPI1 promoter and the CcGPD1 terminator were designated as Y23/95-87, Y23/95-98, Y23/95-99, Y23/95-104 and Y23/95-109.

Example 7A

Construction of a Plasmid (pKK85, FIG. 7) Containing the Hygromycin Resistance Gene Under the Control of the CcTEF1 Promoter and the CcTPI1 Terminator and the *S. cerevisiae* ALD6 Encoding Gene Under the Control of the CcENO1 Promoter and the CcTEF1 Terminator and the *S. cerevisiae* ACS2 Encoding Gene Under the Control of the CcTPI1 Promoter and the CcENO1 Terminator Plasmid pKK77 was digested with EcoRI and XmnI. A 3073 bp fragment was gel isolated and ligated to a 6206 bp fragment obtained by digesting plasmid pKK78 with EcoRI. The plasmid pKK77 contains the *S. cerevisiae* ALD6 encoding gene under the control of the CcENO1 promoter and the CcTEF1 terminator and the plasmid pKK78 contains the *S. cerevisiae* ACS2 encoding gene under the control of the CcTPI1 promoter and the CcENO1 terminator. The resulting plasmid was designated as pKK84. The plasmid pKK76 was digested with BamHI and XmnI. A 2652 bp fragment was gel isolated and ligated to a 9279 bp fragment obtained by digesting pKK84 with BamHI. The plasmid pKK76 contains the hygromycin resistance gene under the control of the CcTEF1 promoter and the CcTPI1 terminator. The resulting plasmid was designated as pKK85 (FIG. 7).

Example 7B

Figure 7:
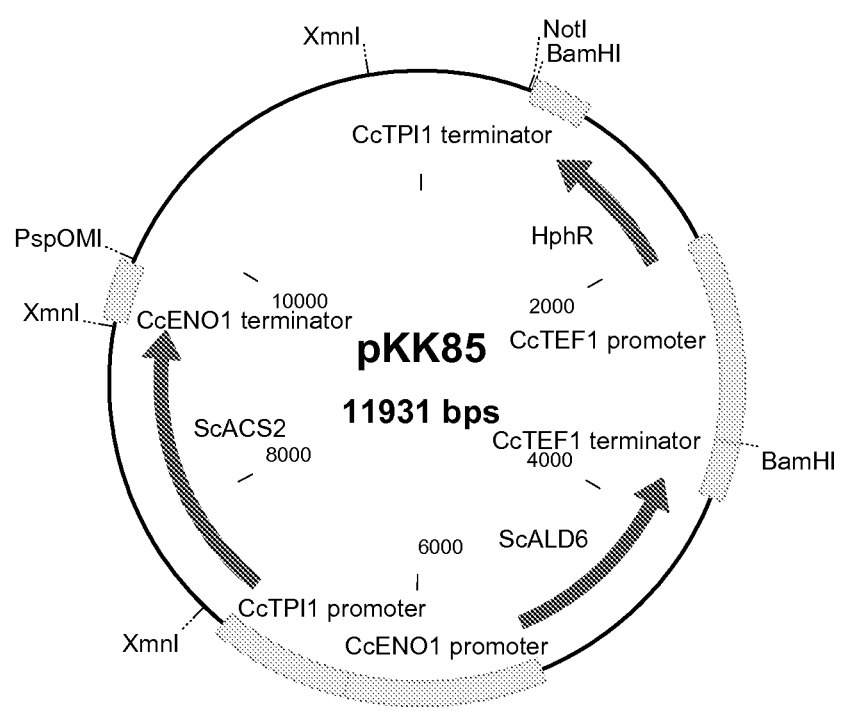
FIG. 7 is a diagram depicting plasmid pKK85.

Generation of a Genetically Modified *C. curvatus* (Y23/85) with an Integrated ALD6 Encoding and ACS2 Encoding Genes and Hygromycin Resistance Gene by Transforming Wild-type *C. curvatus* with Digested Plasmid pKK85 (FIG. 7, Ex. 7A)

Plasmid pKK85 was restricted with NotI and PspOMI, and the resulting linear DNA was used to transform wild-type *C. curvatus* strain ATCC 20509 designated as Y23 by electroporation. The transformed cells were screened for hygromycin resistance. Several hygromycin-resistant colonies were analysed at DNA level by PCR. The transformants originating from the transformation of *C. curvatus* with NotI and PspOMI cut pKK85 and Containing the *S. cerevisiae* ALD6 encoding gene under the control of the CcENO1 promoter and the CcTEF1 terminator and the *S. cerevisiae* ACS2 encoding gene under the control of the CcTPI1 promoter and the CcENO1 terminator were designated as Y23/85-119, Y23/85-125, Y23/85-128, Y23/85-129 and Y23/85-139.

Example 8

Generation of a Genetically Modified *C. curvatus* (Y23/81/95) with an Integrated ALD6 Encoding and PDAT Encoding Genes and Hygromycin and Cerulenin Resistance Genes by Transforming Genetically Modified Strain Y23/81-51 (Ex. 3B) with Plasmid pKK95 (FIG. 6, Ex. 6A)

Plasmid pKK95 was restricted with EcoRV and the resulting linear DNA was used to transform a genetically modified strain Y23/81-51 by electroporation. The transformed cells were screened for cerulenin and hygromycin resistance. Several cerulenin and hygromycin resistance colonies were analysed at DNA level by PCR. The transformants originating from the transformation of genetically modified strain Y23/81-51 with EcoRV cut pKK95 and containing the *S. cerevisiae* ALD6 encoding gene under the control of the CcENO1 promoter and the CcTEF1 terminator and the *R. oryzae* PDAT encoding gene under the control of the CcTPI1 promoter and the CcGPD1 terminator were designated as Y23/81/95-18 and Y23/81/95-42.

Example 9

Generation of a Genetically Modified *C. curvatus* (Y23/85/95) with an Integrated ALD6, ACS2 and PDAT Encoding Genes and Hygromycin and Cerulenin Resistance Genes by Transforming Genetically Modified Strain Y23/85-128 (Ex. 7B) with Plasmid pKK95 (FIG. 6, Ex. 6A)

Plasmid pKK95 was restricted with EcoRV and the resulting linear DNA was used to transform a genetically modified strain Y23/85-128 by electroporation. The transformed cells were screened for cerulenin and hygromycin resistance. Several cerulenin and hygromycin resistance colonies were analysed at DNA level by PCR. The transformants originating from the transformation of genetically modified strain Y23/85-128 with EcoRV cut pKK95 and containing the *S. cerevisiae* ALD6 encoding gene under the control of the CcENO1 promoter and the CcTEF1 terminator, the *S. cerevisiae* ACS2 encoding gene under the control of the CcTPI1 promoter and the CcENO1 terminator and *R. oryzae* PDAT encoding gene under the control of the CcTPI1 promoter and the CcGPD1 terminator were designated as Y23/85/95-4 and Y23/85/95-68.

Example 10

Cloning of *Mucor circinelloides* TPI (McTPI1) Promoter and Terminator Region

A genomic fragment of the *M. circinelloides* TPI1 gene was amplified by PCR from genomic *M. circinelloides* f. *griseocyanus* (D-82202, VTT Culture Collection) DNA with degenerate primers identified as SEQ ID NO:54 (Mould TPI1) and SEQ ID NO:55 (Mould TPI3). The degenerate primers were designed based on a consensus sequence of TPI1 genes of *Rhizopus oryzae, Fusarium oxysporum, Aspergillus fumigatus, A. terreus* and *A. nidulans*. A ~400 bp genomic fragment was isolated and sequenced.

A genomic fragment containing the McTPI1 promoter region was obtained with a ligation-mediated PCR amplification with TPI1 gene specific oligonucleotides identified as SEQ ID NO:56 (MC_TPI2) and SEQ ID NO:57 (MC_TPI1), together with oligonucleotides identified as SEQ ID NO:3 (PCR Linker I) and SEQ ID NO:4 (PCR Linker II), similarly as in Example 1A except that SspI-digested *M. circinelloides* DNA was used. A ~1500 bp PCR fragment was isolated and sequenced.

The *M. circinelloides* TPI1 promoter was PCR amplified by using primers identified as SEQ ID NO:58 (MC_TPI7) and SEQ ID NO:59 (MC_TPI_8), and the *M. circinelloides* genomic DNA as the template. A PCR fragment was digested with PstI and BamHI. A 1251 bp fragment was gel isolated and ligated to a PstI and BamHI-digested pBluescript KS-plasmid. The resulting plasmid was designated pKK56. Plasmid pKK56 contains the *M. circinelloides* TPI1 promoter.

A genomic fragment containing the McTPI1 terminator region was obtained with a ligation-mediated PCR amplification with TPI1 gene specific oligonucleotides identified as SEQ ID NO:60 (MC_TPI4) and SEQ ID NO:61 (MC_TPI3), together with oligonucleotides identified as SEQ ID NO:3 (PCR Linker I) and SEQ ID NO:4 (PCR Linker II), similarly as in Example 1A except that NruI-digested *M. circinelloides* DNA was used. A ~1500 bp PCR fragment was isolated and partially sequenced.

The *M. circinelloides* TPI1 terminator was PCR amplified by using primers identified as SEQ ID NO:62 (MC_TPI5) and SEQ ID NO:63 (MC_TPI6), and the *M. circinelloides* genomic DNA as the template. A PCR fragment was digested with XbaI and BamHI. A 347 bp fragment was gel isolated and ligated to a XbaI and BamHI-digested pBluescript KS-plasmid. The resulting plasmid was designated pKK57. Plasmid pKK57 contains the *M. circinelloides* TPI1 terminator.

Example 11

Cloning of *Mucor circinelloides* TEF (McTEF1) Promoter and Terminator Region

A genomic fragment of the *M. circinelloides* TEF1 gene was amplified by PCR from genomic *M. circinelloides* f. *griseocyanus* (D-82202, VTT Culture Collection) DNA with degenerate primers identified as SEQ ID NO:64 (Mould TEF1) and SEQ ID NO:65 (Mould TEF4). The degenerate primers were designed based on a consensus sequence of TEF1 genes of *Rhizopus oryzae, Fusarium oxysporum, Aspergillus terreus* and *A. nidulans*. A ~600 bp genomic fragment was isolated and sequenced.

A genomic fragment containing the McTEF1 promoter region was obtained with a ligation-mediated PCR amplification with TEF1 gene specific oligonucleotides identified as SEQ ID NO:66 (MC_TEF2) and SEQ ID NO:67 (MC_TEF1), together with oligonucleotides identified as SEQ ID NO:3 (PCR Linker I) and SEQ ID NO:4 (PCR Linker II), similarly as in Example 1A except that SspI-digested *M. circinelloides* DNA was used. A ~500 bp PCR fragment was isolated and sequenced. Nested primers identified as SEQ ID NO:68 (MC_TEF6) and SEQ ID NO:69 (MC_TEF5) were designed and used in a ligation-mediated PCR amplification together with oligonucleotides identified as SEQ ID NO:3 (PCR Linker I) and SEQ ID NO:4 (PCR Linker II), similarly as above except that HaeIII-digested *M. circinelloides* DNA was used. A ~1500 bp PCR fragment was isolated and sequenced.

The *M. circinelloides* TEF1 promoter was PCR amplified by using primers identified as SEQ ID NO:70 (MC_TEF9) and SEQ ID NO:71 (MC_TEF10), and the *M. circinelloides* genomic DNA as the template. A PCR fragment was digested with HindIII and PstI and a 1387 bp fragment was gel isolated and ligated to a HindIII and PstI-digested pBluescript KS-plasmid. The resulting plasmid was designated pKK64. Plasmid pKK64 contains the *M. circinelloides* TEF1 promoter.

A genomic fragment containing the McTEF1 terminator region was obtained with a ligation-mediated PCR amplification with TPI1 gene specific oligonucleotides identified as SEQ ID NO:72 (MC_TEF4) and SEQ ID NO:73 (MC_TEF3), together with oligonucleotides identified as SEQ ID NO:3 (PCR Linker I) and SEQ ID NO:4 (PCR Linker II), similarly as in Example 1A except that SspI-digested *M. circinelloides* DNA was used. A ~1100 bp PCR fragment was isolated and sequenced. Nested primers identified as SEQ ID NO:74 (MC_TEF8) and SEQ ID NO:75 (MC_TEF7) were designed and used in a ligation-mediated PCR amplification together with oligonucleotides identified as SEQ ID NO:3 (PCR Linker I) and SEQ ID NO:4 (PCR Linker II), similarly as above except that HpaI-digested *M. circinelloides* DNA was used. A ~1200 bp PCR fragment was isolated and sequenced.

The *M. circinelloides* TEF1 terminator was PCR amplified by using primers identified as SEQ ID NO:76 (MC_TEF11) and SEQ ID NO:77 (MC_TEF12), and the *M. circinelloides* genomic DNA as the template. A PCR fragment was digested with XmaI and EcoRI and a 389 bp fragment was gel isolated and ligated to a XmaI and EcoRI-digested pBluescript KS-plasmid. The resulting plasmid was designated pKK65. Plasmid pKK65 contains the *M. circinelloides* TEF1 terminator.

Example 12

Cloning of *Mucor circinelloides* PGK (McPGK1) Promoter Region

A genomic fragment of the *M. circinelloides* PGK1 gene was amplified by PCR from genomic *M. circinelloides* f. *griseocyanus* (D-82202, VTT Culture Collection) DNA with degenerate primers identified as SEQ ID NO:78 (Mould PGK4) and SEQ ID NO:79 (Mould PGK2). The degenerative primers were designed based on a consensus sequence of PGK1 genes of *Rhizopus oryzae, Fusarium oxysporum, Aspergillus fumigatus, A. oryzae* and *A. nidulans*. A ~250 bp genomic fragment was isolated and sequenced.

A genomic fragment containing the McPGK1 promoter region was obtained with a ligation-mediated PCR amplification with PGK1 gene specific oligonucleotides identified as SEQ ID NO:80 (MC_PGK2) and SEQ ID NO:81 (MC_PGK1), together with oligonucleotides identified as SEQ ID NO:3 (PCR Linker I) and SEQ ID NO:4 (PCR Linker II), similarly as in Example 1A except that SspI-digested *M. circinelloides* DNA was used. A ~1300 bp PCR fragment was isolated and sequenced. Nested primers identified as SEQ ID NO:82 (MC_PGK4) and SEQ ID NO:83 (MC_PGK3) were designed and used in a ligation-mediated PCR amplification together with oligonucleotides identified as SEQ ID NO:3 (PCR Linker I) and SEQ ID NO:4 (PCR Linker II), similarly as above except that HaeIII-digested *M. circinelloides* DNA was used. A ~600 bp PCR fragment was isolated and sequenced.

The *M. circinelloides* PGK1 promoter was PCR amplified by using primers identified as SEQ ID NO:84 (MC_PGK5) and SEQ ID NO:85 (MC_PGK6), and the *M. circinelloides* genomic DNA as the template. A PCR fragment was digested with SacII and XbaI and a 1291 bp fragment was gel isolated and ligated to a SacII and XbaI-digested pBluescript KS-plasmid. The resulting plasmid was designated pKK62. Plasmid pKK62 contains the *M. circinelloides* PGK1 promoter.

Example 13

Cloning of *Mucor circinelloides* GPD (McGPD1) Promoter Region

A genomic fragment containing the McGPD1 promoter region was obtained with a ligation-mediated PCR amplification with *Mucor circinelloides* (Syn. *racemosus*) GPD1 gene (GenBank accession number AJ293012, version number AJ293012.1) specific oligonucleotides identified as SEQ ID NO:86 (MC_GPD2) and SEQ ID NO:87 (MC_GPD1), together with oligonucleotides identified as SEQ ID NO:3 (PCR Linker I) and SEQ ID NO:4 (PCR Linker II), similarly as in Example 1A except that EcoRV-digested *M. circinelloides* (D-82202, VTT Culture Collection) DNA was used. A ~500 bp PCR fragment was isolated and sequenced. Nested primers identified as SEQ ID NO:88 (MC_GPD10) and SEQ ID NO:89 (MC_GPD9) were designed and used in a ligation-mediated PCR amplification together with oligonucleotides identified as SEQ ID NO:3 (PCR Linker I) and SEQ ID NO:4 (PCR Linker II), similarly as above except that StuI-digested *M. circinelloides* DNA was used. A ~1400 bp PCR fragment was isolated and sequenced.

The *M. circinelloides* GPD1 promoter was PCR amplified by using primers identified as SEQ ID NO:90 (MC_GPD11) and SEQ ID NO:91 (MC_GPD12), and the *M. circinelloides* genomic DNA as the template. A PCR fragment was digested with EcoRI and HindIII and a 1440 bp fragment was gel isolated and ligated to a EcoRI and HindIII-digested pBluescript KS-plasmid. The resulting plasmid was designated pKK59. Plasmid pKK59 contains the *M. circinelloides* GPD1 promoter.

Example 14A

Cloning of *E. coli* Hygromycin Resistance Gene; Construction of a Plasmid (pKK69) Having the *E. coli* Hygromycin Resistance Gene Under the Control of the McPGK1 Promoter and the McTPI1 Terminator Plasmid pKK62 was digested with SacII and SbfI. A 1286 bp fragment was gel isolated. Plasmid pKK52 was digested with SbfI. A 1034 bp fragment was gel isolated. The 1286 bp fragment originated from plasmid pKK62 and the 1034 bp fragment originated from plasmid pKK52 were ligated to a 3268 bp fragment obtained by digesting plasmid pKK57 with SacII and SbfI. Plasmid pKK52 contains the *E. coli* hygromycin resistance gene, plasmid pKK62 contains the *M. circinelloides* PGK1 promoter and plasmid pKK57 contains the *M. circinelloides* TPI1 terminator. The resulting plasmid was designated pKK69. Plasmid pKK69 contains the *E. coli* hygromycin resistance gene under the control of the *M. circinelloides* PGK1 promoter and the *M. circinelloides* TPI1 terminator.

Example 14B

Cloning of *S. cerevisiae* Cerulenin Resistance Gene; Construction of a Plasmid (pKK92) Having the *S. cerevisiae* Cerulenin Resistance Gene Under the Control of the McPGK1 Promoter and the McTPI1 Terminator Plasmid pKK80 was digested with PstI. A 1685 bp fragment was gel isolated. Plasmid pKK80 contains the *S. cerevisiae* cerulenin resistance gene. The 1685 bp fragment was ligated to a 4554 bp fragment obtained by digesting plasmid pKK69 with SbfI. Plasmid pKK69 contains the *M. circinelloides* PGK1 promoter and the *M. circinelloides* TPI1 terminator. The resulting plasmid was designated pKK92. Plasmid pKK92 contains the *S. cerevisiae* cerulenin resistance gene under the control of the *M. circinelloides* PGK1 promoter and the *M. circinelloides* TPI1 terminator.

Example 15A

Construction of a Plasmid (pKK75, FIG. 8) Containing the Hygromycin Resistance Gene Under the Control of the McPGK1 Promoter and the McTPI1 Terminator and the *S. cerevisiae* ALD6 Gene Under the Control of the McTPI1 Promoter and the McTEF1 Terminator Plasmid pKK56 was digested with BamHI and PstI. A 1251 bp fragment was gel isolated. Plasmid pKK56 contains the McTPI1 promoter. Plasmid RoALD was digested with SbfI. A 1514 bp fragment was gel isolated. The plasmid RoALD contains the *S. cerevisiae* ALD6 (SEQ ID NO:47) encoding gene which has been codon optimized according to *Rhizopus oryzae* filamentous fungus codon usage (SEQ ID NO:49) with flanking SbfI restriction sites. The 1251 bp fragment originating from the plasmid pKK56 and the 1514 bp fragment originating from the plasmid RoALD were ligated to a 3321 bp fragment obtained by digesting plasmid pKK65 with BamHI and SbfI. Plasmid pKK65 contains the McTEF1 terminator. The resulting plasmid was designated as pKK73. Plasmid pKK73 contains the *S. cerevisiae* ALD6 encoding gene under the control of the *M. circinelloides* TPI1 promoter and the *M. circinelloides* TEF1 terminator.

Plasmid pKK69 was digested with BamHI and XmnI. A 2652 bp fragment was gel isolated and ligated to a 6086 bp fragment obtained by digesting plasmid pKK73 with BamHI. Plasmid pKK69 contains the *E. coli* hygromycin resistance gene under the control of the *M. circinelloides* PGK1 promoter and the *M. circinelloides* TPI1 terminator. The resulting plasmid was designated as pKK75 (FIG. 8).

Example 15B

Figure 8:
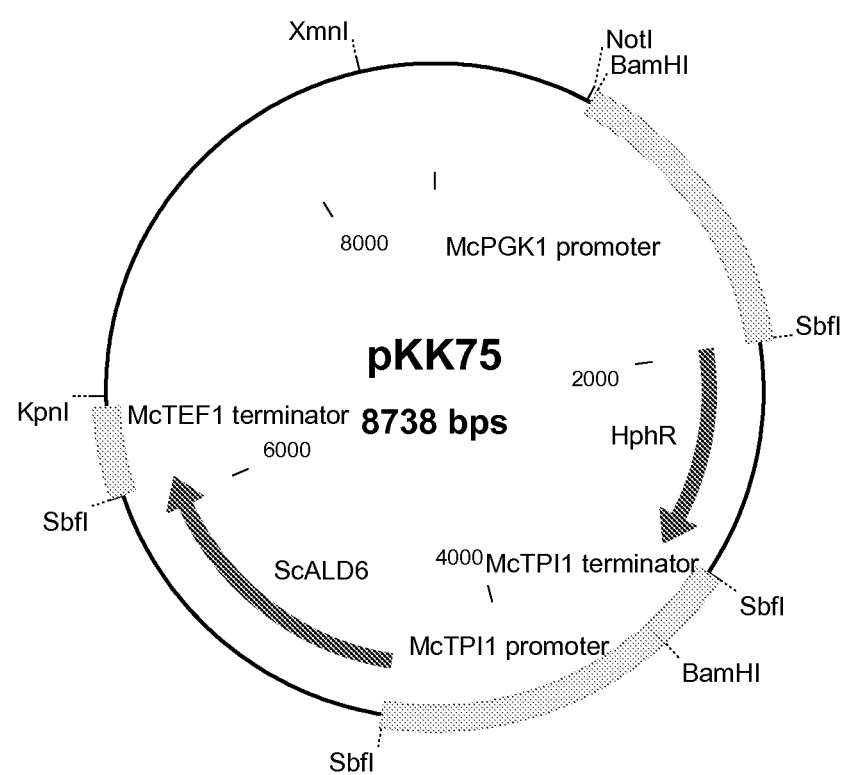
FIG. 8 is a diagram depicting plasmid pKK75.

Generation of a Genetically Modified *Mucor circinelloides* (M22/75) with an Integrated ALD6 Encoding Gene and a Hygromycin Resistance Gene by Transforming Wild-type *M. circinelloides* with Digested Plasmid pKK75 (FIG. 8, Ex. 15A)

Plasmid pKK75 was restricted with KpnI and NotI. A 5866 bp fragment was gel isolated and used to transform a wild-type *M. circinelloides* strain (D-82202, VTT Culture Collection) designated as M22, using a *Mucor protoplast* transformation method (Wolff et. al. 2002). The transformed cells were screened for hygromycin resistance. Several hygromycin-resistant colonies were analysed at DNA level by PCR. The transformants originating from the transformation of the wild-type *M. circinelloides* strain with KpnI and NotI cut pKK75 and containing the *S. cerevisiae* ALD6 encoding gene under the control of the McTPI1 promoter and the McTEF1 terminator were designated as M22/75-80 and M22/75-86.

Example 16A

Construction of a Plasmid (pKK94, FIG. 9) Containing the Hygromycin Resistance Gene Under the Control of the McPGK1 Promoter and the McTPI1 Terminator and the *S. cerevisiae* ALD6 Encoding Gene Under the Control of the McTPI1 Promoter and the McTEF1 Terminator and the *S. cerevisiae* ACS2 Encoding Gene Under the Control of the McTEF1 Promoter and the McTPI1 Terminator Plasmid pKK57 was digested with PstI. A 351 bp fragment was gel isolated and ligated to a 4326 bp fragment obtained by digesting plasmid pKK64 with PstI. The plasmid pKK57 contains the McTPI terminator and the plasmid pKK64 contains the McTEF promoter. The resulting plasmid was designated pKK90Pre. Plasmid RoACS was digested with SbfI. A 2060 bp fragment was gel isolated and ligated to a 4677 bp fragment obtained by digesting plasmid pKK90Pre with SbfI. The plasmid RoACS contains the *S. cerevisiae* ACS2 (SEQ ID NO:50) encoding gene which has been codon optimized according to *Rhizopus oryzae* filamentous fungus codon usage (SEQ ID NO:92) with flanking SbfI restriction sites. The resulting plasmid was designated as pKK90.

Plasmid pKK75 was digested with KpnI followed by removal of the 3' overhangs by T4 DNA polymerase and each of the 4 dNTPs. KpnI (blunt)-digested plasmid pKK75 was digested with NotI and a 5866 bp fragment was gel isolated. The plasmid pKK75 contains the *E. coli* hygromycin resistance gene under the control of the *M. circinelloides* PGK1 promoter and the *M. circinelloides* TPI1 terminator and *S. cerevisiae* ALD6 encoding gene under the control of the *M. circinelloides* TPI1 promoter and the *M. circinelloides* TEF1 terminator. The 5866 bp fragment originating from plasmid pKK75 was ligated to a 6698 bp fragment obtained by digesting plasmid pKK90 with SmaI and NotI. The resulting plasmid was designated as pKK94 (FIG. 9).

Example 16B

Figure 9:
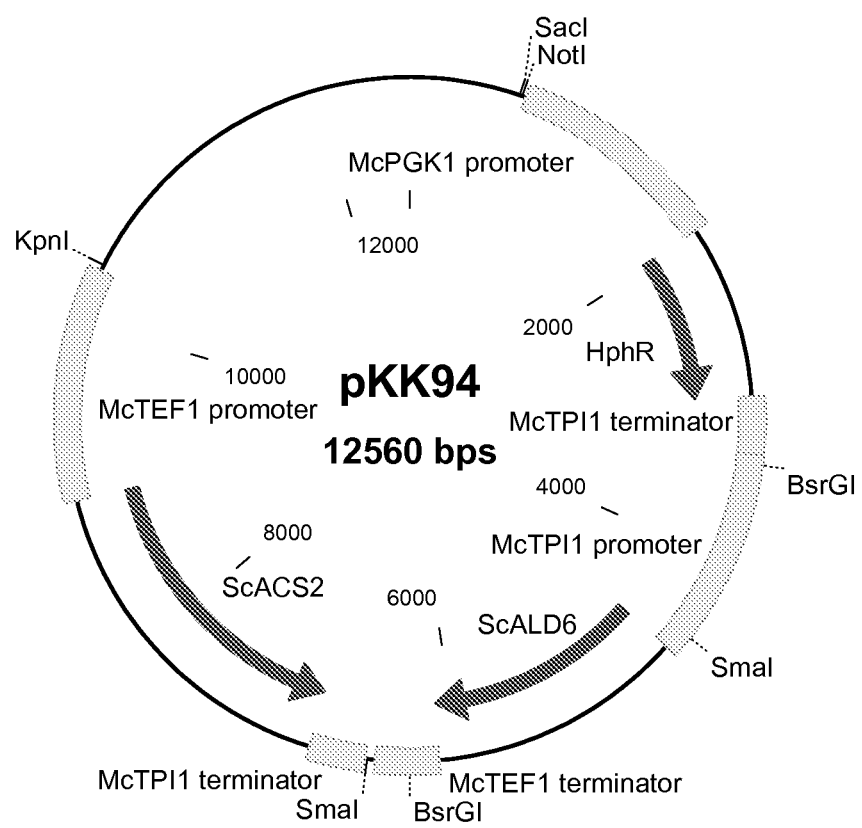
FIG. 9 is a diagram depicting plasmid pKK94.

Generation of a Genetically Modified *Mucor circinelloides* (M22/94) with an Integrated ALD6 and ACS2 Encoding Genes and a Hygromycin Resistance Gene by Transforming Wild-type *M. circinelloides* with Digested Plasmid pKK94 (FIG. 9, Ex. 16A)

Plasmid pKK94 was restricted with KpnI and SacI. A 9701 bp fragment was gel isolated and used to transform a wild-type *M. circinelloides* strain (D-82202, VTT Culture Collection) designated as M22, using the transformation method described in Example 15B. The transformed cells were screened for hygromycin resistance. Several hygromycin resistant colonies were analysed at DNA level by PCR. The transformants originating from the transformation of a wild-type *M. circinelloides* strain with KpnI and SacI cut pKK94 and containing the *S. cerevisiae* ALD6 encoding gene under the control of the McTPI1 promoter and the McTEF1 terminator and *S. cerevisiae* ACS2 encoding gene under the control of the McTEF1 promoter and the McTPI1 terminator were designated as M22/94-12, M22/94-16 and M22/94-24.

Example 17A

Figure 10:
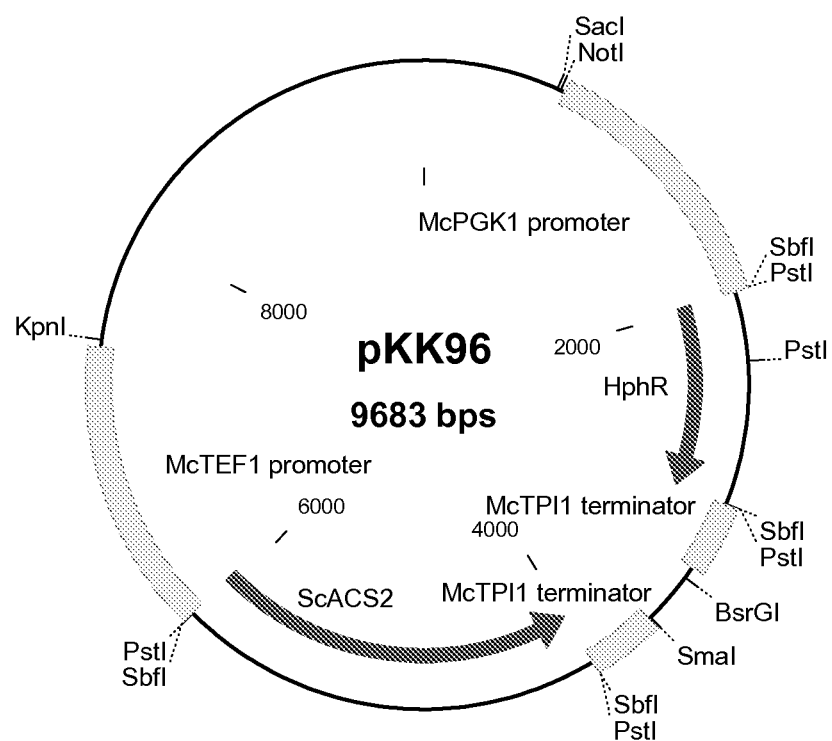
FIG. 10 is a diagram depicting plasmid pKK96.

Construction of a Plasmid (pKK96, FIG. 10) Containing the Hygromycin Gene Under the Control of the McPGK1 Promoter and the McTPI1 Terminator and the *S. cerevisiae* ACS2 Encoding Gene Under the Control of the McTEF1 Promoter and the McTPI1 Terminator Plasmid pKK94 was digested with BsrGI and a 9683 bp fragment was gel isolated and self ligated. The resulting plasmid was designated as pKK96 (FIG. 10). The plasmid pKK96D contains the *S. cerevisiae* ACS2 encoding gene under the control of the McTEF1 promoter and the McTPI1 terminator.

Example 17B

Generation of a Genetically Modified *Mucor circinelloides* (M22/96) with an Integrated ACS2 Encoding Gene and Hygromycin Resistance Gene by Transforming Wild-type *M. circinelloides* with Digested Plasmid pKK96 (FIG. 10, Ex. 17A)

Plasmid pKK96 was restricted with KpnI and SacI. A 6824 bp fragment was gel isolated and used to transform the wild-type *M. circinelloides* strain (D-82202, VTT Culture Collection) designated as M22, using the transformation method described in Example 15B. The transformed cells were screened for hygromycin resistance. Several hygromycin resistant colonies were analysed at DNA level by PCR. The transformants originating from the transformation of the wild-type *M. circinelloides* strain with KpnI and SacI cut pKK96D and containing the *S. cerevisiae* ACS2 encoding gene under the control of the McTEF1 promoter and the McTPI1 terminator were designated as M22/96-1 and M22/96-6.

Example 18A

Construction of a Plasmid (pKK98) Containing the Cerulenin Resistance Gene Under the Control of the McPGK1 Promoter and the McTPI1 Terminator and the *R. oryzae* PDAT Gene Under the Control of the McGPD1 Promoter and the McTEF1 Terminator Plasmid pKK59 was digested with SbfI and XbaI. A 1467 bp fragment was gel isolated and ligated to a 3309 bp fragment obtained by digesting plasmid pKK65 with SbfI and XbaI. The plasmid pKK59 contains the McGPD1 promoter and the plasmid pKK65 contains the McTEF1 terminator. The resulting plasmid was designated as pKK88. Plasmid RoPDAT was digested with SbfI. A 1844 bp fragment was gel isolated and ligated to a 4776 bp fragment obtained by digesting plasmid pKK88 with SbfI. The plasmid RoPDAT contains the *R. oryzae* PDAT (SEQ ID NO:52) encoding gene, which has been codon optimized according to *R. oryzae* codon usage (SEQ. ID. NO 93) with flanking SbfI restriction sites. The resulting plasmid was designated as pKK97.

Plasmid pKK97 was digested with EcoRI. A 3659 bp fragment was gel isolated and ligated to a 6239 bp fragment obtained by digesting plasmid pKK92 with EcoRI. The plasmid pKK92 contains the *S. cerevisiae* cerulenin resistance gene under the control of the McPGK1 promoter and the McTPI1 terminator. The resulting plasmid was designated as pKK98 (FIG. 11).

Example 18B

Figure 11:
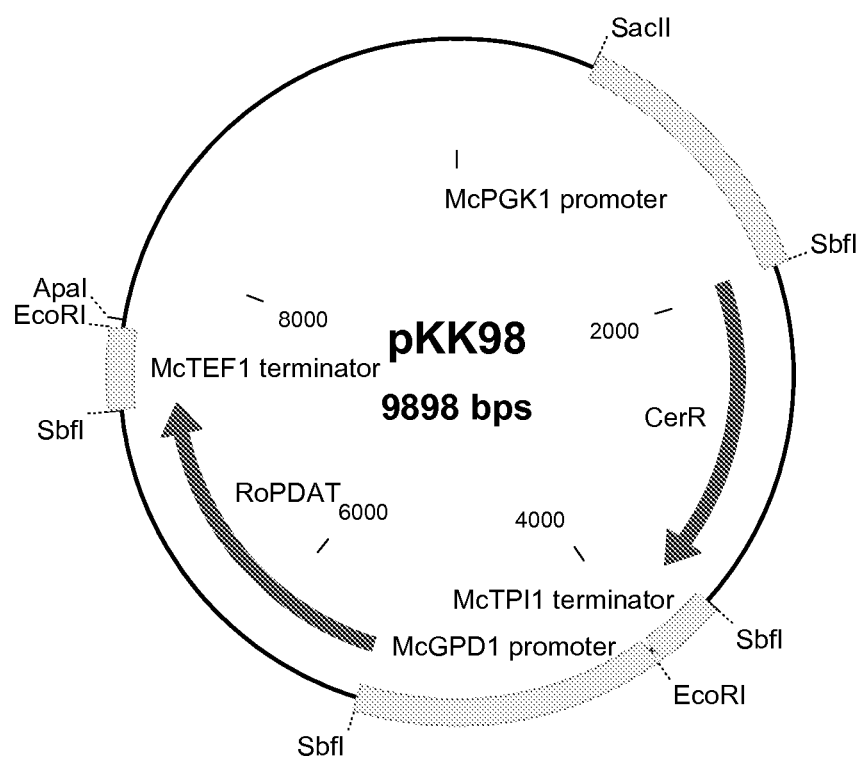
FIG. 11 is a diagram depicting plasmid pKK98.

Generation of a Genetically Modified *Mucor circinelloides* (M22/98) with an Integrated PDAT Encoding Gene and Cerulenin Resistance Gene by Transforming Wild-type *M. circinelloides* with Digested Plasmid pKK98 (FIG. 11, Ex. 18A)

Plasmid pKK98 was restricted with ApaI and SacII. A 7029 bp fragment was gel isolated and used to transform the wild-type *M. circinelloides* strain (D-82202, VTT Culture Collection) designated as M22, using the transformation method described in Example 15B. The transformed cells were screened for cerulenin resistance. Several cerulenin resistant colonies were analysed at DNA level by PCR. The transformants originating from the transformation of the wild-type *M. circinelloides* strain with ApaI and SacII cut pKK98 and containing the *R. oryzae* PDAT encoding gene under the control of the McGPD1 promoter and the McTEF1 terminator were designated as M22/98-16.

Example 19

Generation of a Genetically Modified *Mucor circinelloides* (M22/75/98) with Integrated ALD6 and PDAT Encoding Genes and Hygromycin and Cerulenin Resistance Genes by Transforming Genetically Modified Strain M22/75-86 (Ex 15B) with Digested Plasmid pKK98 (FIG. 11, Ex. 18A)

Plasmid pKK98 was restricted with ApaI and SacII. A 7029 bp fragment was gel isolated and used to transform the genetically modified strain M22/75-86, using the transformation method described in Example 15B. The transformed cells were screened for cerulenin resistance. Several cerulenin resistant colonies were analysed at DNA level by PCR. The transformants originating from the transformation of the recombinant M22/75-86 strain with ApaI and SacII cut pKK98 and containing the *R. oryzae* PDAT encoding gene under the control of the McGPD1 promoter and the McTEF1 terminator and the *S. cerevisiae* ALD6 encoding gene under the control of the McTPI1 promoter and the McTEF1 terminator were designated as M22/75/98-7 and M22/75/98-9.

Example 20

Generation of a Genetically Modified *Mucor circinelloides* (M22/94/98) with Integrated ALD6, ACS2 and PDAT Encoding Genes and Hygromycin and Cerulenin Resistance Genes by Transforming Genetically Modified Strain M22/94-31 (Ex 16B) with Digested Plasmid pKK98 (FIG. 11, Ex. 18A)

Plasmid pKK98 was restricted with ApaI and SacII. A 7029 bp fragment was gel isolated and used to transform the genetically modified strain M22/94-31, using the transformation method described in Example 15B. The transformed cells were screened for cerulenin resistance. Several cerulenin resistant colonies were analysed at DNA level by PCR. The transformants originating from the transformation of the recombinant M22/94-31 strain with ApaI and SacII cut pKK98 and containing the *R. oryzae* PDAT encoding gene under the control of the McGPD1 promoter and the McTEF1 terminator, the *S. cerevisiae* ALD6 encoding gene under the control of the McTPI1 promoter and the McTEF1 terminator and the *S. cerevisiae* ACS2 encoding gene under the control of the McTEF1 promoter and the McTPI1 terminator were designated as M22/94/98-19 and M22/94/98-22.

Example 21

Lipid Extraction and Total Lipid and Triglyceride Concentration Measurements

A lipid extraction method was modified from the protocol of Folch et al., 1957. 0.5 to 2 ml of cell culture was taken into an Eppendorf tube. The sample was centrifuged and the supernatant discarded. The pellet was placed rapidly in liquid nitrogen and stored at −80° C. Alternatively, filamentous fungal cells of 2 to 12 ml culture broth were collected by vacuum filtration through disks of glass microfiber filters (Whatman, England). After washing twice with distilled water, biomass was removed from the filter using a clean spatula and put into 2 ml microfuge tubes, which were placed rapidly in liquid nitrogen and stored at −80° C. In a homogenisation step the frozen pellet was suspended in 500 µl of ice-cold methanol with 0.1% BHT (2,6-Di-tert-butyl-4-methylphenol) and homogenised with a Mixer Mill homogenizer with 5-mm zirconium oxide and 3-mm yttrium stabilized zirconium oxide balls (Retsch) at 25 Hz for 5 min. After homogenisation 1000 µl of chloroform was added and homogenisation repeated. After re-homogenisation 300 µl of 20 mM acetic acid was added and the sample vortexed for 10 min. After vortexing the sample was centrifuged 13000 rpm for 5 min at RT. The lower phase was recovered and 1000 µl of chloroform was added to the remaining phase, vortexed and recentrifuged. The lower phases were combined into pre-weighed 2 ml microfuge tubes, and dried, after which the total lipid content of the sample was determined by gravimetry. Then the lipid sample was redissolved in 1.5 ml of chloroform:methanol (2:1)+0.1% BHT and stored at −20° C. For triacylglycerol analysis 100 to 1500 μl of chloroform:methanol extracted lipids were evaporated and re-dissolved in 200-1000 μl of isopropanol. Triacylglycerols were measured enzymatically from the samples by using the Konelab Triglycerides Kit (Thermo Scientific, Finland) and Cobas Mira automated analyser (Roche) or a microtitre-plate reader (Varioskan, Thermo Electron Corporation). This lipid extraction and total lipid and triglyceride concentration measurements methods were used in the following examples if not otherwise indicated.

Example 22

Microaerobic Shake Flask Characterization of Strains Y23/81-51 and Y23/81-66 (Ex. 3B), Y23/86-86 and Y23/86-92 (Ex. 5B), Y23/95-87 and Y23/95-109 (Ex. 6B) and Y23/85/95-4 (Ex. 9), in Glucose Medium with C/N Ratio of 20

Transformants were separately cultivated in 50 ml of culture medium "glucose CN20" (pH 5.5, 20 g glucose, 0.3 g $(NH_4)_2SO_4$, 7.0 g $KH_2PO_4$, 2.5 g $Na_2HPO_4*2\ H_2O$, 1.5 g $MgSO_4*7H_2O$, 4.0 g Yeast extract, 51 mg $CaCl_2$, 8 mg $FeCl_3*6\ H_2O$ and 0.1 mg $ZnSO_4*7\ H_2O$ per liter). Each flask (250 ml) was inoculated to an $OD_{600}$ of 0.3 with cells grown on yeast peptone plus glucose plates. The cultivations were maintained at a temperature of 30° C. with shaking at 100 rpm. Samples for cell dry weight measurement, lipid extraction and HPLC analysis were withdrawn periodically during cultivation. *Cryptococcus curvatus* wild type strain Y23 was used as a control.

Lipid extraction and triacylglycerol concentration measurement were carried out as described in Example 21. Cell dry weight was determined by centrifuging 1 ml of the culture broth in pre-dried, pre-weighed Eppendorf tubes. After washing with 1 ml of distilled water the cell pellet was dried at 100° C. for 24 hours and weighed again. HPLC analyses for sugars were conducted with a Waters 2690 Separation Module and Water System Interfase Module liquid chromatography coupled with a Waters 2414 differential refractometer and Waters 2487 dual absorbance detector. The liquid chromatography columns were a 100×7.8 mm Fast Acid Analysis column from Bio-Rad and a 300×7.8 mm Aminex HPX-87H column from Bio-Rad. The columns were equilibrated with 2.5 mM $H_2SO_4$ in water at 55° C. and samples were eluted with 2.5 mM $H_2SO_4$ in water at 0.5 ml/min flow rate. Data acquisition was done using Waters Millennium software. This HPLC method was used in all appropriate Examples.

After 48 hours cultivation (Table 2A), when 4 to 8 g/l glucose was left, Y23/81, Y23/86, Y23/95 and Y23/85/95 transformants produced 12, 22, 15 and 24% more triacylglycerols with higher rate, respectively, than the control strain in glucose medium. Triacylglycerol yields per used glucose were also better up to 10% with the transformants compared to the control strain. Additionally Y23/85/95 transformant had 13% higher triacylglycerol yield on biomass than the control strain (12.9 and 11.4% TAG yield on biomass, respectively). In particular, after 24 hours of cultivation (Table 2B), the strains expressing ALD or ACS alone, or ALD and ACS together, had enhanced production of triacylglycerols, measured as concentration (g/l) and as yield per biomass and used glucose, with higher rate (mg/l/h) compared to the control strain.

TABLE 2A

Triacylglycerol (TAG) concentration (g/l), rate (mg/l/h) and yield (%) per used glucose after 48 hours microaerobic cultivation in glucose medium with C/N ratio of 20

| Strain | TAG (g/l) | Yield TAG (% used glucose) | TAG mg/l/h |
| --- | --- | --- | --- |
| Control | 0.72 | 5.88 | 15.0 |
| Y23/81 (ALD) | 0.81 | 5.90 | 16.8 |
| Y23/86 (ACS) | 0.88 | 6.00 | 18.3 |
| Y23/95 (PDAT) | 0.82 | 6.02 | 17.2 |
| Y23/85/95 (ALD + ACS + PDAT) | 0.89 | 6.46 | 18.5 |

TABLE 2B

Triacylglycerol (TAG) concentration (g/l) and yield (%) per biomass (CDW) and used glucose after 24 hours microaerobic cultivation in glucose medium with C/N ratio of 20

| Strain | TAG (g/l) | Yield TAG (% CDW) | Yield TAG (% used glucose) | TAG mg/l/h |
| --- | --- | --- | --- | --- |
| Control | 0.22 | 5.15 | 4.29 | 9.1 |
| Y23/81-66 (ALD) | 0.26 | 6.09 | 4.86 | 10.8 |
| Y23/85-125 (ALD + ACS) | 0.31 | 7.01 | 5.49 | 12.8 |
| Y23/86-86 (ACS) | 0.30 | 6.76 | 5.26 | 12.5 |

This example shows that expression of ALD6, ACS2 and PDAT genes in different combinations enhanced triacylglycerol concentrations and rates of production, and triacylglycerol yields from used glucose or per dry weight in cultivation with low C/N ratios.

Example 23

Aerobic Shake Flask Characterization of Strains Y23/81-8, 51, 59, 66 and 69 (Ex. 3B), Y23/85-119, 125, 128, 129 and 139 (Ex. 7B), Y23/86-86, 92, 93, 98 and 100 (Ex. 5B), Y23/95-99 and 104 (Ex. 6B), Y23/81/95-42 (Ex. 8) and Y23/85/95-4 and 68 (Ex. 9), in Glucose Medium with C/N Ratio of 65

Transformants were separately cultivated in 50 ml of Yeast culture medium II (pH 5.5, 20 g glucose, 0.3 g $(NH_4)_2SO_4$, 7.0 g $KH_2PO_4$, 2.5 g $Na_2HPO_4*2\ H_2O$, 1.5 g $MgSO_4*7H_2O$, 0.6 g Yeast extract, 51 mg $CaCl_2$, 8 mg $FeCl_3*6\ H_2O$ and 0.1 mg $ZnSO_4*7\ H_2O$ per liter). Each flask (250 ml) was inoculated to an $OD_{600}$ of 0.3 with cells grown on yeast peptone plus glucose plates. The cultivations were maintained at a temperature of 30° C. with shaking at 250 rpm. Samples for cell dry weight measurement, lipid extraction and HPLC analysis were withdrawn periodically during cultivation. *Cryptococcus curvatus* wild type strain Y23 was used as a control. Cell dry weight was determined and HPLC analysis was carried out as described in Example 22. Lipid extraction and triacylglycerol measurements as described in Example 21.

After 44 hours cultivation (Table 3A) transformants Y23/81, Y23/85, Y23/86, Y23/95, Y23/81/95 and Y23/85/95 had 4, 3, 6, 1, 12 and 4% better triacylglycerol yields per used glucose, respectively, than the control strain. Additionally, transformants Y23/81/95 and Y23/85/95 had 7-8% higher triacylglycerol yield on biomass than the control strain (42.8, 43.0 and 40.0% TAG yield [/CDW], respectively). After 25 hours cultivation (Table 3B), the strains expressing ALD or ACS alone, or ALD and ACS together, had enhanced production of triacylglycerols, measured as concentration (g/l) and as yield per biomass and used glucose.

TABLE 3A

Maximal triacylglycerol (TAG) yield (%) per used glucose after 44 hours cultivation in glucose medium with C/N ratio of 65

| Strain | Yield TAG (% used glucose) |
|---|---|
| Control | 16.6 |
| Y23/81 (ALD) | 17.3 |
| Y23/85 (ALD + ACS) | 17.2 |
| Y23/86 (ACS) | 17.6 |
| Y23/95 (PDAT) | 16.9 |
| Y23/81/95 (ALD + PDAT) | 18.6 |
| Y23/85/95 (ALD + ACS + PDAT) | 17.4 |

TABLE 3B

Triacylglycerol (TAG) concentration (g/l) and yield (%) per biomass (CDW) and used glucose after 25 hours cultivation in glucose medium with C/N ratio of 65

| Strain | TAG (g/l) | Yield TAG (% CDW) | Yield TAG (% used glucose) | TAG mg/l/h |
|---|---|---|---|---|
| Control | 1.01 | 21.7 | 10.3 | 40.5 |
| Y23/81-51, 66 (ALD) | 1.15 | 26.4 | 12.5 | 46.0 |
| Y23/85-125, 129 (ALD + ACS) | 1.14 | 27.2 | 13.3 | 45.4 |
| Y23/86-92, 100 (ACS) | 1.18 | 22.4 | 12.0 | 47.1 |

This example shows that expression of ALD6, ACS2 and PDAT genes in different combinations enhanced triacylglycerol concentrations and rates of production and triacylglycerol yields from used glucose or per dry weight.

Example 24

Aerobic Shake Flask Characterization of Strains Y23/81-66 (Ex. 3B), Y23/85-125 (Ex. 7B), Y23/86-92 (Ex. 5B), Y23/95-98 (Ex. 6B) and Y23/81/95-18 (Ex. 8) in Glucose Medium with C/N Ratio of 103

Transformants were separately cultivated in 50 ml of Yeast culture medium IV (pH 5.5, 20 g glucose, 0.15 g $(NH_4)_2SO_4$, 7.0 g $KH_2PO_4$, 2.5 g $Na_2HPO_4*2\ H_2O$, 1.5 g $MgSO_4*7H_2O$, 0.45 g Yeast extract, 51 mg $CaCl_2$, 8 mg $FeCl_3*6\ H_2O$ and 0.1 mg $ZnSO_4*7\ H_2O$ per liter). Each flask (250 ml) was inoculated to an $OD_{600}$ of 0.3 with cells grown on yeast peptone plus glucose plates. The cultivations were maintained at a temperature of 30° C. with shaking at 250 rpm. Samples for cell dry weight measurement, lipid extraction and HPLC analysis were withdrawn periodically during cultivation. *Cryptococcus curvatus* wild type strain Y23 was used as a control. Cell dry weight was determined and HPLC analysis was carried out as described in Example 22. Lipid extraction and triacylglycerol measurements as described in Example 21.

After 35 hours cultivation, when 6-8 g/l glucose was left, transformants Y23/81-66, Y23/85-125, Y23/86-92, Y23/95-98 and Y23/81/95-18 had 3, 6, 9, 11 and 11% higher triacylglycerol titre and rate than the control strain, respectively. The transformants Y23/81-66, Y23/85-125, Y23/86-92, Y23/95-98 and Y23/81/95-18 had also 11, 19, 7, 20 and 30% better triacylglycerol yields per used glucose, respectively, than the control strain. Additionally Y23/81/95-18 had 24% higher yield on biomass than the control strain (49.4 and 40.0% TAG yields on biomass, respectively).

TABLE 4

Triacylglycerol (TAG) concentration (g/l), rate (mg/l/h) and yield (%) per used glucose after 35 hours cultivation in glucose medium with C/N ratio of 103

| Strain | TAG (g/l) | Yield TAG (% used glucose) | TAG mg/l/h |
|---|---|---|---|
| Control | 2.00 | 16.2 | 57.1 |
| Y23/81-66 (ALD) | 2.05 | 18.0 | 58.7 |
| Y23/85-125 (ALD + ACS) | 2.11 | 19.3 | 60.3 |
| Y23/86-92 (ACS) | 2.17 | 17.4 | 61.9 |
| Y23/95-98 (PDAT) | 2.22 | 19.4 | 63.5 |
| Y23/81/95-18 (ALD + PDAT) | 2.22 | 21.1 | 63.5 |

This example shows that expression of ALD6, ACS2 and PDAT genes in different combinations enhanced triacylglycerol concentrations and rates of production and triacylglycerol yield from used glucose or per dry weight with high C/N ratios.

Example 25

Aerobic Shake Flask Characterization of Strains M22/75-86 (Ex. 15B), M22/96-1 (Ex. 17B), M22/94-24 (Ex. 16B), M22/75/98-9 (Ex. 19) and M22/94/98-19 (Ex. 20), in Glucose Medium with C/N Ratio of 40

Transformants were separately cultivated in 50 ml of mould C/N 40 medium (pH 5.5, 20 g glucose, 1.4 g yeast extract, 2.5 g $KH_2PO_4$, 0.3 g $(NH_4)_2SO_4$, 10 mg $ZnSO_4*7H_2O$, 2 mg $CuSO_4*5H_2O$, 10 mg $MnSO_4$, 0.5 $MgSO_4*7\ H_2O$, 0.1 g $CaCl_2$, 20 mg $FeCl_3*6H_2O$ per liter). Each flask (250 ml) was inoculated with $1*10^7$ spores. The cultivations were maintained at a temperature of 25° C. with shaking at 250 rpm. Samples for cell dry weight measurement, lipid extraction and HPLC analysis were withdrawn periodically during cultivation. *Mucor circinelloides* wild type strain M22 was used as a control. Cell dry weight was determined by vacuum filtration through disks of glass microfiber filters (Whatman, England) of 2 to 24 ml culture broth. After washing twice with distilled water, biomass was removed from the cloth using clean spatula and transferred to pre-dried, pre-weighed 2 ml microfuge tubes in which the mycelia were dried at 100° C. for 48 hours and weighed after cooling in a dessicator. HPLC analysis was carried out as described in Example 22. Lipid extraction and total lipid and triacylglycerol measurements as described in Example 21.

After 46 hours cultivation (Table 5) transformants M22/75-86, M22/96-1, M22/94-24, M22/75/98-9 and M22/94/98-19 produced 21, 9, 18, 91 and 55% more triacylglycerol with higher rate than the control strain, respectively. The transformant M22/75-86, M22/96-1, M22/94-24, M22/75/98-9 and M22/94/98-19 had also 39 (20), 23 (10), 18 (13), 127 (57) and 80 (25) % higher triacylglycerol yield on used glucose (on biomass) than the control strain, respectively. Additionally the transformants M22/75/98-9 and M22/94/98-19 had higher total lipid concentration (0.93-1.09 g/l) and rate (20-24 mg/l/h) with yields on biomass (26.1-31.4%) and on used glucose (6.29-7.52%) than the control strain (0.71 g/l, 15 mg/l/h, 24.6% and 4.09%, respectively).

TABLE 5

Triacylglycerol (TAG) and total lipid concentrations (g/l), rates (mg/l/h) and yields (%) per biomass (CDW; cell dry weight) and used glucose after 46 hours cultivation in glucose medium with C/N ratio of 40

| Strain | TAG g/l | Yield TAG (% CDW) | Yield TAG (% used glucose) | TAG mg/l/h |
|---|---|---|---|---|
| Control | 0.33 | 11.5 | 1.92 | 7.2 |
| M22/75-86 (ALD) | 0.40 | 13.8 | 2.67 | 8.8 |
| M22/96-1 (ACS) | 0.36 | 12.6 | 2.36 | 7.9 |
| M22/94-24 (ALD + ACS) | 0.39 | 13.0 | 2.27 | 8.5 |
| M22/75/98-9 (ALD + PDAT) | 0.63 | 18.1 | 4.35 | 13.7 |
| M22/94/98-19 (ALD + ACS + PDAT) | 0.51 | 14.4 | 3.46 | 11.1 |

| Strain | Lipid g/l | Yield lipid (% CDW) | Yield lipid (% used glucose) | Lipid mg/l/h |
|---|---|---|---|---|
| Control | 0.71 | 24.6 | 4.09 | 15 |
| M22/75-86 (ALD) | 0.76 | 26.1 | 5.04 | 17 |
| M22/96-1 (ACS) | 0.70 | 24.2 | 4.53 | 15 |
| M22/94-24 (ALD + ACS) | 0.71 | 23.5 | 4.10 | 15 |
| M22/75/98-9 (ALD + PDAT) | 1.09 | 31.4 | 7.52 | 24 |
| M22/94/98-19 (ALD + ACS + PDAT) | 0.93 | 26.1 | 6.29 | 20 |

This example shows that expression of ALD6, ACS2 and PDAT genes in different combinations enhanced triacylglycerol and total lipid concentrations and rates of production and triacylglycerol and total lipid yields from used glucose or per dry weight.

Example 26

Aerobic Shake Flask Characterization of Strains M22/75-86 (Ex. 15B), M22/96-1 (Ex. 17B), M22/94-24 (Ex. 16B), M22/75/98-9 (Ex. 19) and M22/94/98-19 (Ex. 20), in Glucose Medium with C/N Ratio of 66

Transformants were separately cultivated in 50 ml of mould C/N 66 medium (pH 5.5, 20 g glucose, 1.0 g yeast extract, 2.5 g $KH_2PO_4$, 0.1 g $(NH_4)_2SO_4$, 10 mg $ZnSO_4 \cdot 7H_2O$, 2 mg $CuSO_4 \cdot 5H_2O$, 10 mg $MnSO_4$, 0.5 g $MgSO_4 \cdot 7 H_2O$, 0.1 g $CaCl_2$, 20 mg $FeCl_3 \cdot 6H_2O$ per liter). Each flask (250 ml) was inoculated with $1*10^7$ spores. The cultivations were maintained at a temperature of 25° C. with shaking at 250 rpm. Samples for cell dry weight measurement, lipid extraction, enzyme activity measurement and HPLC analysis were withdrawn periodically during cultivation. *Mucor circinelloides* wild type strain M22 was used as a control. Cell dry weight was determined as described in Example 25 and HPLC analysis was carried out as described in Example 22. Lipid extraction and total lipid and triacylglycerol measurements as described in Example 21.

After 93 hours cultivation, when 2-6 g/l glucose was left, transformants M22/75-86, M22/96-1, M22/94-24, M22/75+98-9 and M22/94+98-19 had produced 34, 30, 45, 186 and 214% more triacylglycerols with higher rate than the control strain. The transformants M22/75-86, M22/96-1, M22/94-24, M22/75+98-9 and M22/94+98-19 also had 63 (24), 68 (30), 62 (43), 229 (72) and 102 (104) % higher triacylglycerol yield on used glucose (on biomass) than the control strain. Additionally, the transformants produced more lipids (0.89-2.29 g/l) with higher rates (9.6-24.6 mg/l/h) and with higher yields on used glucose (6.90-17.68%) and on biomass (37.2-57.7%) than the control strain (0.71 g/l, 7.6 mg/l/h, 4.82% and 30.2%, respectively).

TABLE 6

Triacylglycerol (TAG) and total lipid concentrations (g/l), rates (mg/l/h) and yields (%) per biomass (CDW; cell dry weight) and used glucose after 93 hours cultivation in glucose medium with C/N ratio of 66.

| Strain | TAG g/l | Yield TAG (% CDW) | Yield TAG (% used glucose) | TAG mg/l/h |
|---|---|---|---|---|
| Control | 0.44 | 18.6 | 2.97 | 4.7 |
| M22/75-86 (ALD) | 0.59 | 23.0 | 4.84 | 6.4 |
| M22/96-1 (ACS) | 0.57 | 24.1 | 4.99 | 6.1 |
| M22/94-24 (ALD + ACS) | 0.64 | 26.6 | 4.82 | 6.9 |
| M22/75/98-9 (ALD + PDAT) | 1.26 | 31.9 | 9.76 | 13.6 |
| M22/94/98-19 (ALD + ACS + PDAT) | 1.38 | 37.9 | 9.00 | 14.8 |

| Strain | Lipid g/l | Yield lipid (% CDW) | Yield lipid (% used glucose) | Lipid mg/l/h |
|---|---|---|---|---|
| Control | 0.71 | 30.2 | 4.8 | 7.6 |
| M22/75-86 (ALD) | 0.96 | 37.2 | 7.8 | 10.3 |
| M22/96-1 (ACS) | 0.89 | 37.3 | 7.7 | 9.6 |
| M22/94-24 (ALD + ACS) | 0.91 | 37.6 | 6.9 | 9.8 |
| M22/75/98-9 (ALD + PDAT) | 2.29 | 57.7 | 17.7 | 24.6 |
| M22/94/98-19 (ALD + ACS + PDAT) | 2.00 | 55.1 | 13.1 | 21.5 |

This example shows that expression of ALD6, ACS2 and PDAT genes in different combinations enhanced triacylglycerol and total lipid concentrations and rates of production and triacylglycerol and total lipid yields from used glucose or per dry weight with high C/N ratios.

Example 27

Microaerobic Shake Flask Characterization of Strains Y23/81-51 and Y23/81-66 (Ex. 3B), Y23/85-125 and Y23/85-128 (Ex. 7B), Y23/86-86 and Y23/86-92 (Ex. 5B), Y23/95-87 and Y23/95-109 (Ex. 6B) and Y23/85/95-4 (Ex. 9), in Xylose Medium with C/N Ratio of 20

Transformants were separately cultivated in 50 ml of culture medium "xylose CN20" (pH 5.5, 20 g xylose, 0.3 g $(NH_4)_2SO_4$, 7.0 g $KH_2PO_4$, 2.5 g $Na_2HPO_4 \cdot 2 H_2O$, 1.5 g $MgSO_4 \cdot 7H_2O$, 4.0 g Yeast extract, 51 mg $CaCl_2$, 8 mg $FeCl_3 \cdot 6 H_2O$ and 0.1 mg $ZnSO_4 \cdot 7 H_2O$ per liter). Each flask (250 ml) was inoculated to an $OD_{600}$ of 0.3 with cells grown on yeast peptone plus glucose plates. The cultivations were maintained at a temperature of 30° C. with shaking at 100 rpm. Samples for cell dry weight measurement, lipid extraction, enzyme activity measurement and HPLC analysis were withdrawn periodically during cultivation. *Cryptococcus curvatus* wild type strain Y23 was used as a control.

Lipid extraction and triacylglycerol concentration measurements were carried out as described in Example 21. Cell dry weight was determined and HPLC analysis was carried out as described in Example 22.

At the end of cultivation samples for acetaldehyde dehydrogenase and acetyl-CoA synthetase activity measurements were taken. Cells were harvested by centrifugation and washed once with 100 mM Tris-HCl pH 7.0. Washed cells were stored at −20° C. Frozen cells were melted and washed once with 100 mM Tris-HCl pH 7.0 and suspended in 100 mM Tris-HCl pH 7.0, 1 mM DTT buffer containing EDTA-free protease inhibitors (Roche, USA). Cell disruption was carried out with 0.5 mm diameter glass beads (Sigma Chemicals Co, USA) in a Fast Prep homogenizer (Thermo Scientific, USA). Cell debris was removed by centrifugation and supernatant was used in enzyme activity measurements. Acetaldehyde dehydrogenase and acetyl-CoA synthetase activity measurements were carried out with a Konelab Arena automatic analyzer (Thermo Scientific, Finland). The acetaldehyde dehydrogenase reaction mixture contained (final concentration) 50 mM potassium phosphate pH 7.0, 15 mM pyrazole, 0.4 mM DTT, 10 mM $MgCl_2$, 0.4 mM NADP and cell extract. The reaction was started with 0.1 mM acetaldehyde. The formation of NADPH was followed at 340 nm. One unit was defined as the amount of formation of 1 μmol of NADPH per min. The acetyl-CoA synthetase reaction mixture contained (final concentration) 100 mM Tris-HCl pH 7.5, 10 mM L-malate pH 7.5, 0.2 mM Coenzyme A, 8 mM ATP, 1 mM NAD, 10 mM $MgCl_2$, 3 U/ml malate dehydrogenase, 0.4 U/ml citrate synthase and cell extract. The reaction was started with 100 mM potassium acetate. The formation of NADH was followed at 340 nm. One unit was defined as the amount of formation of 1 μmol of NADH per min.

After 24 hours cultivation the transformants Y23/81, Y23/85, Y23/86, Y23/95 and Y23/85/95 produced 13-31% more triacylglycerol with 5-38% higher yield on biomass than the control strain. The transformants Y23/81, Y23/86, Y23/95 and Y23/85/95 also had 4-12% higher yields on used xylose than the control strain. The transformants having ALD (ACS) encoding gene expressed had 21.5 to 42.7 (1.5 to 1.9) times higher ALD (ACS) activity than the control strain.

TABLE 7

Triacylglycerol (TAG) concentration (g/l), rate (mg/l/h) and yields (%) per biomass (CDW; cell dry weight) and used xylose after 24 hours microaerobic cultivation in xylose medium with C/N ratio of 20

| Strain | TAG (g/l) | Yield TAG (% CDW) | Yield TAG (% used xylose) | TAG mg/l/h |
|---|---|---|---|---|
| Control | 0.16 | 4.33 | 3.46 | 6.8 |
| Y23/81 (ALD) | 0.20 | 5.98 | 3.61 | 8.2 |
| Y23/85 (ALD + ACS) | 0.18 | 4.54 | 3.46 | 7.3 |
| Y23/86 (ACS) | 0.21 | 5.33 | 3.86 | 8.9 |
| Y23/95 (PDAT) | 0.20 | 5.55 | 3.68 | 8.4 |
| Y23/85/95 (ALD + ACS + PDAT) | 0.20 | 5.55 | 3.72 | 8.2 |

TABLE 8

Relative acetaldehyde dehydrogenase (ALD) and acetyl-CoA synthetase (ACS) activities in microaerobic cultivation in xylose with C/N ratio of 20 compared to the control strain ALD and ACS activities

| Strain | ALD | ACS |
|---|---|---|
| Control | 1 | 1 |
| Y23/81 (ALD) | 42.7 | 1.2 |
| Y23/85 (ALD + ACS) | 27.3 | 1.9 |
| Y23/86 (ACS) | 4.3 | 1.5 |
| Y23/95 (PDAT) | 2.3 | 1.2 |
| Y23/85/95 (ALD + ACS + PDAT) | 21.5 | 1.5 |

This example shows that expression of ALD6, ACS2 and PDAT genes in different combinations enhanced triacylglycerol concentrations and rates of production and triacylglycerol yields from used xylose or per dry weight with low C/N ratios. Additionally, the example shows that acetaldehyde dehydrogenase (ALD) and acetyl-CoA synthetase (ACS) enzymes are expressed in active forms.

Example 28

Aerobic Shake Flask Characterization of Strains Y23/81-8 and 59 (Ex. 3B), Y23/85-119 and 128 (Ex. 7B), Y23/86-86 and 92 (Ex. 5B), Y23/95-99 and 109 (Ex. 6B), Y23/81/95-18 and 42 (Ex. 8) and Y23/85/95-4 and 68 (Ex. 9), in Xylose Medium with C/N Ratio of 103

Transformants were separately cultivated in 50 ml of Yeast xylose culture medium IV (pH 5.5, 20 g xylose, 0.15 g $(NH_4)_2SO_4$, 7.0 g $KH_2PO_4$, 2.5 g $Na_2HPO_4*2\ H_2O$, 1.5 g $MgSO_4*7H_2O$, 0.45 g Yeast extract, 51 mg $CaCl_2$, 8 mg $FeCl_3*6\ H_2O$ and 0.1 mg $ZnSO_4*7\ H_2O$ per liter). Each flask (250 ml) was inoculated to an $OD_{600}$ of 0.3 with cells grown on yeast peptone plus glucose plates. The cultivations were maintained at a temperature of 30° C. with shaking at 250 rpm. Samples for cell dry weight measurement, lipid extraction and HPLC analysis were withdrawn periodically during cultivation. *Cryptococcus curvatus* wild type strain Y23 was used as a control. Cell dry weight was determined and HPLC analysis was carried out as described in Example 22. Lipid extraction and triacylglycerol measurements as described in Example 21.

After 52 hours cultivation the transformants Y23/81, Y23/85, Y23/86, Y23/95, Y23/81/95 and Y23/85/95 had produced 23, 19, 50, 52, 40 and 75% more triacylglycerol than the control strain. The transformants Y23/81, Y23/85, Y23/86, Y23/95, Y23/81/95 and Y23/85/95 had also 35, 47, 59, 60, 103 and 111% higher triacylglycerol yield on biomass and 11, 11, 15, 28, 66 and 63% higher triacylglycerol yield on used xylose than the control strain. Additionally the transformants Y23/81, Y23/85, Y23/86, Y23/95, Y23/81/95 and Y23/85/95 had higher lipid concentration (2.40-2.90 g/l) and rate (46-56 mg/l/h) with higher yield on biomass (56.5-78.8%) than the control strain (2.35 g/l, 45 mg/l/h and 52.2%, respectively). The transformants Y23/81/95 and Y23/85/95 had also higher lipid yield on used xylose (29.0-31.6%) than the control strain (25.6%).

TABLE 9

Triacylglycerol (TAG) and total lipid concentrations (g/l), rates (mg/l/h) and yields (%) per biomass (CDW; cell dry weight) after 52 hours cultivation in xylose medium with C/N ratio of 103. Triacylglycerol yield (%) from used xylose is also indicated.

| Strain | TAG (g/l) | Yield TAG (% CDW) | Yield TAG (% used xylose) | TAG mg/l/h |
|---|---|---|---|---|
| Control | 0.60 | 13.3 | 6.52 | 19.0 |
| Y23/81 (ALD) | 0.83 | 17.9 | 7.23 | 26.4 |
| Y23/85 (ALD + ACS) | 0.79 | 19.6 | 7.26 | 25.0 |
| Y23/86 (ACS) | 0.90 | 21.1 | 7.52 | 28.5 |
| Y23/95 (PDAT) | 0.91 | 21.3 | 8.37 | 28.8 |
| Y23/81/95 (ALD + PDAT) | 0.84 | 27.0 | 10.8 | 26.6 |
| Y23/85/95 (ALD + ACS + PDAT) | 1.05 | 28.0 | 10.7 | 33.3 |

| Strain | Lipid (g/l) | Yield lipid (% CDW) | Lipid mg/l/h |
|---|---|---|---|
| Control | 2.35 | 52.2 | 45 |
| Y23/81 (ALD) | 2.90 | 62.3 | 56 |
| Y23/85 (ALD + ACS) | 2.53 | 62.9 | 49 |
| Y23/86 (ACS) | 2.58 | 60.6 | 50 |
| Y23/95 (PDAT) | 2.40 | 56.5 | 46 |
| Y23/81/95 (ALD + PDAT) | 2.45 | 78.8 | 47 |
| Y23/85/95 (ALD + ACS + PDAT) | 2.85 | 76.0 | 55 |

This example shows that expression of ALD6, ACS2 and PDAT genes in different combinations enhanced triacylglycerol and total lipid concentrations and rates of production and triacylglycerol and total lipid yields per dry weight and triacylglycerol yields from used xylose with high C/N ratios.

Example 29

Aerobic Shake Flask Characterization of Strains M22/75-80 (Ex. 15B), M22/96-6 (Ex. 17B), M22/98-16 (Ex. 18B), M22/94-16 (Ex. 16B), M22/75/98-7 (Ex. 19) and M22/94/98-22 (Ex. 20), in Xylose Medium with C/N Ratio of 66

Transformants were separately cultivated in 50 ml of mould xylose C/N 66_medium (pH 5.5, 20 g xylose, 1.0 g yeast extract, 2.5 g $KH_2PO_4$, 0.1 g $(NH_4)_2SO_4$, 10 mg $ZnSO_4*7H_2O$, 2 mg $CuSO_4.5H_2O$, 10 mg $MnSO_4$, 0.5 g $MgSO_4*7 H_2O$, 0.1 g $CaCl_2$, 20 mg $FeCl_3*6H_2O$ per liter). Each flask (250 ml) was inoculated with $1*10^7$ spores. The cultivations were maintained at a temperature of 25° C. with shaking at 250 rpm. Samples for cell dry weight measurement, lipid extraction, enzyme activity measurement and HPLC analysis were withdrawn periodically during cultivation. *Mucor circinelloides* wild type strain M22 was used as a control. Cell dry weight was determined as described in Example 25, and HPLC analysis was carried out as described in Example 22. Lipid extraction and total lipid and triacylglycerol measurements as described in Example 21.

After 143 hours cultivation the transformants M22/75-80, M22/96-6, M22/98-16, M22/75/98-7 and M22/94/98-22 had higher TAG concentration (0.33-0.48 g/l TAG) compared to the control strain (0.28 g/l TAG). The all transformants had also higher TAG yield (%) per biomass (13.71-17.78%) than the control strain (12.15%) and the transformants M22/96-6, M22/98-16, M22/75/98-7 and M22/94/98-22 had also higher TAG yield (%) per used xylose (4.83-6.23%) than the control strain (3.97%). Additionally the transformants M22/75/98-7 and M22/94/98-22 had higher lipid concentration (0.79-1.13 g/l), rate (9.2-10.8 mg/l/h) and lipid yields on biomass (48.9-55.6%) and on used xylose (17.1-18.3%) than the control strain (0.92 g/l, 6.4 mg/l/h, 40.0% and 13.0%, respectively).

TABLE 10

Triacylglycerol (TAG) and total lipid concentrations (g/l), rates (mg/l/h) and yields (%) per biomass (CDW; cell dry weight) and used xylose after 143 hours cultivation in xylose medium with C/N ratio of 66

| Strain | TAG (g/l) | Yield TAG (% CDW) | Yield TAG (% used xylose) | TAG mg/l/h |
|---|---|---|---|---|
| Control | 0.28 | 12.2 | 3.97 | 1.9 |
| M22/75-80 (ALD) | 0.33 | 14.8 | 3.45 | 2.3 |
| M22/96-6 (ACS) | 0.33 | 15.3 | 5.40 | 2.3 |
| M22/94-16 (ALD + ACS) | 0.27 | 13.7 | 3.67 | 1.9 |
| M22/98-16 (PDAT) | 0.48 | 13.7 | 4.83 | 3.3 |
| M22/75/98-7 (ALD + PDAT) | 0.48 | 17.8 | 6.23 | 3.3 |
| M22/94/98-22 (ALD + ACS + PDAT) | 0.45 | 16.1 | 5.31 | 3.1 |

| Strain | Lipid (g/l) | Yield lipid (% CDW) | Yield lipid (% used xylose) | Lipid mg/l/h |
|---|---|---|---|---|
| Control | 0.92 | 40.0 | 13.0 | 6.4 |
| M22/75-80 (ALD) | 1.00 | 44.8 | 10.5 | 7.0 |
| M22/96-6 (ACS) | 0.90 | 41.5 | 14.7 | 6.3 |
| M22/94-16 (ALD + ACS) | 0.82 | 41.6 | 11.1 | 5.7 |
| M22/98-16 (PDAT) | 1.62 | 46.4 | 16.4 | 11.3 |
| M22/75/98-7 (ALD + PDAT) | 1.32 | 48.9 | 17.1 | 9.2 |
| M22/94/98-22 (ALD + ACS + PDAT) | 1.54 | 55.6 | 18.3 | 10.8 |

This example shows that expression of ALD6, ACS2 and PDAT genes in different combinations enhanced triacylglycerol and total lipid concentrations and rates of production and triacylglycerol and total lipid yields from used xylose or per dry weight with high C/N ratios.

Example 30

Production of Triacylglycerol or Lipid by Strains of *C. curvatus* Modified by Addition of Genes Encoding ALD and PDAT (Y23/81/95-18, Ex. 8) or ALD and PDAT and ACS (Y23/85/95-4 Ex. 9) in High Cell Density Cultures Grown on Glucose with C/N Ratio of 80

Transformants (Y23/85/95-4 and Y23/81/95-18) were separately cultivated in Multifors bioreactors (max. working volume 500 ml, Infors HT, Switzerland) at pH 4.0, 30° C., in 500 ml medium containing 90 to 96 g glucose, 2.56 g $(NH_4)_2SO_4$, 1.2 g $KH_2PO_4$, 0.3 g $Na_2HPO_4.2H_2O$, 1.5 g $MgSO_4.7H_2O$, 0.1 g $CaCl_2.6H_2O$, 5.26 mg citric acid.$H_2O$, 5.26 mg $ZnSO_4.7H_2O$, 0.1 mg $MnSO_4.4H_2O$, 0.5 mg $CoCl_2.6H_2O$, 0.26 mg $CuSO_4.5H_2O$, 0.1 mg $Na_2MoO_4.2H_2O$, 1.4 mg $FeSO_4.7H_2O$, 0.1 mg $H_3BO_4$, 0.05 mg D-biotin, 1.0 mg CaPantothenate, 5.0 mg nicotinic acid, 25 mg myoinositol, 1.0 mg thiamine.HCl, 1.0 mg pyridoxine.HCl and 0.2 mg p-aminobenzoic acid per liter. The pH was maintained constant by addition of 1 M KOH or 1 M $H_3PO_4$. Cultures were agitated at 1000 rpm (2 Rushton turbine impellors) and aerated at 2 volumes air per volume culture per minute (vvm). Clerol FBA 3107 antifoaming agent (Cognis, Saint-Fargeau-Ponthierry Cedex France, 1 ml l$^{-1}$) was added to prevent foam accumulation. Bioreactors were inoculated to initial OD$_{600}$ of 0.5 to 4.0 with cells grown in the same medium (substituting 1.5 g urea per liter for (NH$_4$)$_2$SO$_4$ and omitting the CaCl$_2$.6H$_2$O) in 50 ml volumes in 250 ml flasks at 30° C. with shaking at 200 rpm for 24 to 42 h. Samples for cell dry weight measurement, lipid extraction and HPLC analysis were withdrawn periodically during cultivation. *Cryptococcus curvatus* wild type strain Y23 was used as the control. For measurement of the yield of triacylglycerol on glucose or biomass, some control cultures contained 58 to 134 g glucose l$^{-1}$.

Lipid extraction and triacylglycerol concentration measurements were carried out as described in Example 21. Cell dry weight was determined by centrifuging 0.5 to 2.0 ml culture broth in pre-dried, pre-weighed 2 ml microfuge tubes. After washing twice with 1.8 ml distilled water, the cell pellet was dried at 100° C. for 48 h and weighed after cooling in a dessicator. HPLC analyses were carried out as described in Example 22.

Table 11 shows that a transformant containing the genes for ALD and PDAT produced 23% more triacylglycerol than Y23, with a 24% increase in the yield on glucose consumed when cells were cultivated to high cell density in bioreactor cultures. A transformant containing the genes for ALD, ACS and PDAT produced 15% more triacylglycerol than Y23, with a 12% increase in the yield on glucose consumed.

TABLE 11

Triacylglycerol produced in pH controlled bioreactor culture of Y23 and transformants of Y23 expressing ALD + PDAT or ALD + ACS + PDAT, with glucose as carbon source and C/N 80. Data is the average of 2 (transformants) or 4 to 9 (Y23) cultures ± standard error of the mean. Percentage increase is shown in parenthesis

| Strain | TAG (g/l) | Yield TAG (% glucose consumed) |
|---|---|---|
| Y23 | 17.3 ± 0.3 | 18.8 ± 1.0 |
| Y23/81/95-18 | 21.3 ± 0.8 | 23.3 ± 1.0 |
| (ALD + PDAT) | (23%) | (24%) |
| Y23/85/95-4 | 19.9 ± 0.1 | 21.1 ± 0.1 |
| (ALD + ACS + PDAT) | (15%) | (12%) |

This example shows that expression of ALD6, ACS2 and PDAT genes in different combinations enhanced triacylglycerol concentrations and triacylglycerol yields from used glucose in high cell density cultures.

Example 31

Production of Triacylglycerol or Lipid by Strains of *C. curvatus* Modified by Addition of Genes Encoding ALD and PDAT (Y23/81/95-18, Ex. 8) or ALD and PDAT and ACS (Y23/85/95-4, Ex. 9) in High Cell Density Cultures Grown on Xylose with C/N Ratio of 80

Transformants (Y23/85/95-4 and Y23/81/95-18) were separately cultivated in Multifors bioreactors as described in Example 30. The medium contained 92 to 118 g xylose per liter, instead of glucose. Bioreactors were inoculated to initial OD$_{600}$ of 17 to 24 with cells grown in low nitrogen medium with glucose as carbon source in the Multifors bioreactors at 30° C., as described for lipid production in Example 30. Alternatively, some cultures of Y23 were inoculated with cells grown in flasks, as described in Example 30, to initial OD$_{600}$ 0.2 to 0.5. Samples for cell dry weight measurement, lipid extraction and HPLC analysis were withdrawn periodically during cultivation. *Cryptococcus curvatus* wild type strain Y23 was used as the control.

Lipid extraction and total lipid and triacylglycerol concentration measurements were carried out as described in Example 21. Cell dry weight was determined as described in Example 30. HPLC analyses were carried out as described in Example 22.

Table 12 shows that a transformant containing the genes for ALD and PDAT produced 7% more triacylglycerol than Y23, with a 17% increase in the yield on xylose consumed and a 3% increase in the yield on biomass when cells were cultivated to high cell density in bioreactor cultures. A transformant containing the genes for ALD, ACS and PDAT produced only 1% more triacylglycerol than Y23, but showed 13% increase in the yield on xylose consumed and 4% increase in yield on biomass.

TABLE 12

Triacylglycerol produced in pH controlled bioreactor culture of Y23 and transformants of Y23 expressing ALD + PDAT or ALD + ACS + PDAT, with xylose as carbon source and C/N 80. Data is the average of 2 (transformants) or 4 (Y23) cultures, ± standard error of the mean. Percentage increase is shown in parenthesis.

| Strain | TAG (g/l) | Yield TAG (% CDW) | Yield TAG (% xylose consumed) |
|---|---|---|---|
| Y23 | 17.9 ± 1.4 | 46.9 ± 4.0 | 17.2 ± 1.2 |
| Y23/81/95-18 | 19.1 ± 0.3 | 48.4 ± 5.7 | 20.2 ± 0.5 |
| (ALD + PDAT) | (7%) | (3%) | (17%) |
| Y23/85/95-4 | 18.1 ± 0.3 | 49.0 ± 3.4 | 19.5 ± 0.0 |
| (ALD + ACS + PDAT) | (1%) | (4%) | (13%) |

Table 13 shows that a transformant containing the genes for ALD and PDAT produced 10% more lipid than Y23, with a 21% increase in the yield on xylose consumed and a 2% increase in the yield on biomass when cells were cultivated to high cell density in bioreactor cultures. A transformant containing the genes for ALD, ACS and PDAT produced 3% more lipid than Y23, with 16% higher yield on xylose consumed and a 3% increase in yield on biomass.

TABLE 13

Lipid produced in pH controlled bioreactor culture of Y23 and transformants of Y23 expressing ALD + PDAT or ALD + ACS + PDAT, with xylose as carbon source and C/N 80. Data is the average of 2 (transformants) or 4 (Y23) cultures, ± standard error of the mean. Percentage increase is shown in parenthesis.

| Strain | Lipid (g/l) | Yield lipid (% CDW) | Yield lipid (% xylose consumed) |
|---|---|---|---|
| Y23 | 20.5 ± 1.3 | 55.9 ± 7.2 | 19.8 ± 2.5 |
| Y23/81/95-18 | 22.5 ± 0.6 | 57.0 ± 1.9 | 23.8 ± 0.8 |
| (ALD + PDAT) | (10%) | (2%) | (21%) |
| Y23/85/95-4 | 21.2 ± 0.1 | 57.5 ± 1.0 | 22.9 ± 0.3 |
| (ALD + ACS + PDAT) | (3%) | (3%) | (16%) |

This example shows that expression of ALD6, ACS2 and PDAT genes in different combinations enhanced triacylglycerol and total lipid concentrations and triacylglycerol and total lipid yields from used xylose or per dry weight in high cell density cultures.

Example 32

Production of Triacylglycerol or Lipid by Strain of *M. circinelloides* Modified by Addition of Genes Encoding ALD and PDAT and ACS (M22/94/98-19, Ex. 20) in pH Controlled Bioreactor Cultures Grown on Glucose with C/N Ratio of 60

Transformant (M22/94/98-19) was cultivated in Braun Biostat® CT bioreactors (2.5 max working volume, B. Braun Biotech International, Sartorius AG, Germany) at pH 5.0, 30° C., in 1.0 to 1.2 l medium containing 53 g glucose, 1.57 g $(NH_4)_2SO_4$, 2.5 g $KH_2PO_4$, 0.2 g $MgSO_4.7H_2O$, 0.1 g $CaCl_2.6H_2O$, 5.26 mg citric acid.$H_2O$, 5.26 mg $ZnSO_4.7H_2O$, 0.1 mg $MnSO_4.4H_2O$, 0.5 mg $CoCl_2.6H_2O$, 0.26 mg $CuSO_4.5H_2O$, 0.1 mg $Na_2MoO_4.2H_2O$, 1.4 mg $FeSO_4.7H_2O$, 0.1 mg $H_3BO_4$, 0.005 mg D-biotin, and 0.05 mg thiamine.HCl per liter. The pH was maintained constant by addition of 1 M KOH or 1 M $H_2PO_4$. Cultures were agitated at 600 rpm (2 Rushton turbine impellors) and aerated at 1 volume air per volume culture per minute (vvm). Polypropylene glycol (mixed molecular weights containing Fluka P1200, Fluka P2000 and Henkel Performance Chemicals Foamaster in a ratio of 4:4;1, 1 ml $l^{-1}$) was added to prevent foam accumulation. Bioreactors were inoculated to an initial biomass concentration of approximately 100 mg $l^{-1}$ with mycelia grown in the same medium with the following modifications: 15 g glucose $l^{-1}$, enough $(NH_4)_2SO_4$ to provide a C/N ratio of 16.2, and additionally 4.0 g agar $l^{-1}$. Pre-cultures were grown in 50 ml volumes in 250 ml flasks at 30° C. with shaking at 200 rpm for 42 to 72 h. Samples for cell dry weight measurement, lipid extraction and HPLC analysis were withdrawn periodically during cultivation. Biomass was separated from the culture supernatant by filtration under vacuum. *Mucor circinelloides* wild type strain M22 was used as the control.

Lipid extraction and total lipid and triacylglycerol concentration measurements were carried out as described in Example 21. Cell dry weight was determined as descriped in Example 25, except that disposable cleaning cloth (X-tra, 100% viscose household cleaning cloth, Inex Partners Oy, Helsinki) was used in vacuum filtration. HPLC analyses were carried out as described in Example 22.

Table 14 shows that a transformant containing the genes for ALD, ACS and PDAT produced 17% more triacylglycerol than Y23, with 8% increase in the yield on glucose consumed, when cells were cultivated in bioreactor cultures.

TABLE 14

Triacylglycerol produced in pH controlled bioreactor cultures of M22 and transformant of M22 expressing ALD + ACS + PDAT, with glucose as carbon source and C/N 60. Percentage increase is shown in parenthesis.

| Strain | TAG (g/l) | Yield TAG (% glucose consumed) |
|---|---|---|
| M22 | 9.8 | 21.9 |
| M22/94/98-19 (ALD + ACS + PDAT) | 11.5 (17%) | 23.6 (8%) |

Table 15 shows that a transformant containing the genes for ALD, ACS and PDAT produced 44% more lipid than M22, with 55% higher yield on glucose consumed and 26% increase in yield of lipid on biomass, when cells were cultivated in bioreactor cultures.

TABLE 15

Lipid produced in pH controlled bioreactor cultures of M22 and transformant of M22 expressing ALD + ACS + PDAT, with glucose as carbon source and C/N 60. Percentage increase is shown in parenthesis.

| Strain | Lipid (g/l) | Yield lipid (% CDW) | Yield lipid (% glucose consumed) |
|---|---|---|---|
| M22 | 10.4 | 59.4 ± 2.8 | 19.7 |
| M22/94/98-19 (ALD + ACS + PDAT) | 14.9 (44%) | 75.4 ± 3.5 (26%) | 30.5 (55%) |

This example shows that expression of ALD6, ACS2 and PDAT genes enhanced triacylglycerol and total lipid concentrations and triacylglycerol and total lipid yields from used glucose or total lipid yield per dry weight in high cell density cultures.

Example 33

Production of Triacylglycerol or Lipid by Strain of *M. circinelloides* Modified by Addition of Genes Encoding ALD and PDAT and ACS (M22/94/98-19, Ex. 20) in pH Controlled Bioreactor Cultures Grown on Xylose with C/N Ratio of 60

Transformant (M22/94/98-19) was cultivated in Braun Biostat CT bioreactors as described in Example 32. The medium contained 44 to 56 g xylose per liter, instead of glucose cultures were supplemented with 1 g peptone per liter and the $(NH_4)_2SO_4$ concentration was reduced to 1.12 g per liter. Samples for cell dry weight measurement, lipid extraction and HPLC analysis were withdrawn periodically during cultivation. *Mucor circinelloides* wild type strain M22 was used as the control.

Lipid extraction and total lipid and triacylglycerol concentration measurements were carried out as described in Example 21. Cell dry weight was determined as described in Example 32. HPLC analyses were carried out as described in Example 22.

Table 16 shows that a transformant containing genes for ALD, ACS and PDAT produced 11% more triacylglycerol than M22, with 10% increased yield on xylose consumed and 9% increased yield on biomass in pH controlled bioreactor cultures.

TABLE 16

Triacylglycerol produced in pH controlled bioreactor cultures of M22 and transformant of M22 expressing ALD + ACS + PDAT, with xylose as carbon source and C/N 60. Percentage increase is shown in parenthesis.

| Strain | TAG (g/l) | Yield TAG (% CDW) | Yield TAG (% xylose consumed) |
|---|---|---|---|
| M22 | 5.6 | 46.5 ± 2.7 | 22.9 |
| M22/94/98-19 (ALD + ACS + PDAT) | 6.2 (11%) | 50.9 ± 1.4 (9%) | 25.1 (10%) |

Table 17 shows that a transformant containing the genes for ALD and ACS and PDAT produced 24% more lipid than M22 and the yield of lipid on biomass was 22% higher than in M22, when mycelia were grown on xylose. The yield of lipid on xylose consumed was increased 18%.

TABLE 17

Lipid produced in pH controlled bioreactor culture of M22 and transformant of M22 expressing ALD + ACS + PDAT, with xylose as carbon source and C/N 60. Percentage increase is shown in parenthesis.

| Strain | Lipid (g/l) | Yield lipid (% CDW) | Yield lipid (% xylose consumed) |
|---|---|---|---|
| M22 | 5.8 | 49.2 ± 4.6 | 24.1 |
| M22/94/98-19 (ALD + ACS + PDAT) | 7.1 (22%) | 58.2 ± 0.6 (18%) | 28.7 (19%) |

This example shows that expression of ALD6, ACS2 and PDAT genes enhanced triacylglycerol and total lipid concentrations and triacylglycerol and total lipid yields from used xylose or per dry weight in high cell density cultures.

Example 34

Construction of a Plasmid Containing a Marker Gene Under the Control of an Endogenous Promoter and Terminator and a Pyruvate Decarboxylase (PDC) Encoding Gene Under the Control of an Endogenous Promoter and Terminator A pyruvate decarboxylase (PDC) encoding gene, such as PDC1 from *S. cerevisiae* (SEQ ID NO:94) which encodes the amino acid sequence of SEQ ID NO:95 is codon optimised. The codon optimised PDC encoding gene with flanking SbfI restriction sites is digested with SbfI and ligated to a plasmid containing an endogenous promoter and terminator, such as plasmid pKK77pre. The resulting plasmid which contains the PDC encoding gene under the control of the endogenous promoter and terminator will be linearised e.g. with BamHI and ligated with a fragment containing the marker gene under the control of the endogenous promoter and terminator. Such fragment can be obtained e.g. by digesting a plasmid pKK67 with BamHI and XmnI. The resulting plasmid contains the PDC encoding gene under the control of the endogenous promoter and terminator and the marker gene under the control of the endogenous promoter and terminator.

Example 35

Generation of Genetically Modified Strain with an Integrated PDC Together with ALD6 and/or ACS2 Encoding Genes and Marker Genes by Transforming Genetically Modified Strains with Plasmid Containing PDC Encoding Gene (Ex 34)

The plasmid containing the PDC encoding gene (Ex. 34) is restricted e.g. with NotI and PspOMI, and the resulting linear DNA containing the PDC encoding gene under the control of the endogenous promoter and terminator and the marker gene under the control of the endogenous promoter and terminator is used to transform e.g. a genetically modified strain Y23/81-51 (Ex. 3B), Y23/86-92 (Ex. 5B) or Y23/85-128 (Ex. 7B) by electroporation or a genetically modified strain M22/75-86 (Ex. 15B), M22/96-1 (Ex. 17B) or M22/94-31 (Ex 16B) using the transformation method described in Example 15B. The transformed cells are screened e.g. for antibiotic resistance. Several transformed colonies are analysed at DNA level by PCR.

Example 36

Aerobic Shake Flask Characterization of Strains Harbouring PDC Together with ALD6 and/or ACS2 Encoding Genes and Marker Genes in Glucose or Xylose Medium with Different C/N Ratios Transformants are separately cultivated in 50 ml of culture medium such as described in Examples 22, 23, 24, 27 or 28. Each flask (250 ml) is inoculated to an $OD_{600}$ of 0.3 with cells grown on yeast peptone plus glucose plates. The cultivations are maintained at a temperature of 30° C. with shaking at 250 rpm. Samples for cell dry weight measurement, lipid extraction and HPLC analysis are withdrawn periodically during cultivation. *Cryptococcus curvatus* wild type strain Y23 is used as a control. Cell dry weight is determined and HPLC analysis is carried out as described in Example 22. Lipid extraction and triacylglycerol measurements as described in Example 21. Alternatively transformants are separately cultivated in 50 ml of culture medium such as described in Examples 25, 26 or 29. Each flask (250 ml) is inoculated with $1*10^7$ spores. The cultivations are maintained at a temperature of 25° C. with shaking at 250 rpm. Samples for cell dry weight measurement, lipid extraction and HPLC analysis are withdrawn periodically during cultivation. *Mucor circinelloides* wild type strain M22 is used as a control. Cell dry weight is determined as described in Example 25 and HPLC analysis is carried out as described in Example 22. Lipid extraction and triacylglycerol measurements as described in Example 21.

The transformants harbouring PDC together with ALD6 and/or ACS2 encoding genes produce more triacylglycerol than the control strain. Additionally the transformants harbouring PDC together with ALD6 and/or ACS2 encoding gene have higher triacylglycerol yield on used carbon than the control strain.

Example 37A

Figure 12:
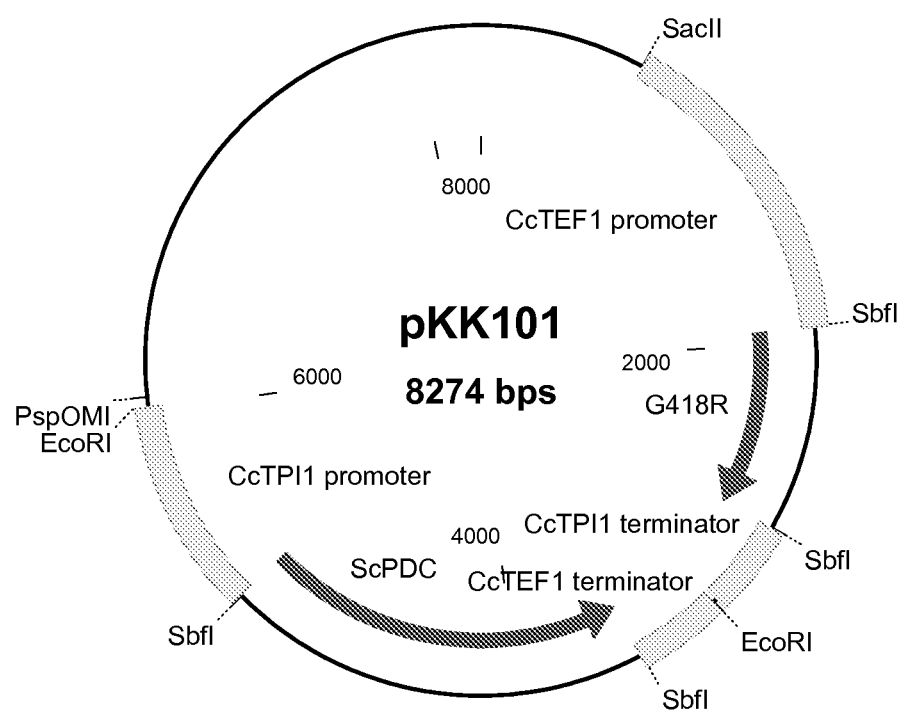
FIG. 12 is a diagram depicting plasmid pKK101.

Construction of a Plasmid (pKK101) Containing the G418 Resistance Gene Under the Control of the CcTEF1 Promoter and the CcTPI1 Terminator and the *S. cerevisiae* PDC1 Encoding Gene Under the Control of the CcTPI1 Promoter and the CcTEF1 Terminator The plasmid Y4_TPIp-PDC-TEFt (Geneart AG, Germany) contains a *S. cerevisiae* PDC1 (SEQ ID NO:95) encoding gene which has been codon optimized according to *Ustilago maydis* yeast codon usage (SEQ ID NO:96) with the CcTPI1 promoter and the CcTEF1 terminator. Plasmid Y4-TPIp-PDC-TEFt was digested with EcoRI. A 2893 bp fragment was gel isolated and ligated to a 5381 bp fragment obtained by digesting a plasmid designated pKK67 (Ex. 2B) with EcoRI. The resulting plasmid was designated as pKK101 (FIG. 12). The plasmid pKK101 contains a *S. cerevisiae* PDC1 encoding gene under the control of the CcTPI1 promoter and the CcTEF1 terminator and the *E. coli* G418 resistance gene under the control of the CcTEF1 promoter and the CcTPI1 terminator.

Example 37B

Generation of Genetically Modified Strains with an Integrated PDC Encoding Gene and G418 Resistance Gene by Transforming Wild-type *C. curvatus* and Genetically Modified Strains Y23/81-66 (Ex. 3B), Y23/85-125 (Ex. 7B), Y23/86-86 (Ex. 5B), Y23/95-99 (Ex. 6B), Y23/81/95-18 (Ex. 8) and Y23/85/95-4 (Ex. 9) with Digested Plasmid pKK101 (FIG. 12, Ex. 37A)

Plasmid pKK101 was restricted with SacII and PspOMI, and the resulting linear DNA was used to transform wild-type *C. curvatus* strain ATCC20509 designated as Y23 and genetically modified strains Y23/81-66, Y23/85-125, Y23/86-86, Y23/95-99, Y23/81/95-18 and Y23/85/95-4 by electroporation. The transformed cells were screened for G418 resistance. Several G418 resistance colonies were analysed at DNA level by PCR. The transformants originating from the transformation of wild-type *C. curvatus* strain ATCC20509 designated as Y23 and genetically modified strains Y23/81-66, Y23/85-125, Y23/86-86, Y23/95-99, Y23/81/95-18 and Y23/85/95-4 with SacII and PspOMI cut pKK101 and containing the *S. cerevisiae* PDC1 encoding gene under the control of the CcTPI1 promoter and the CcTEF1 terminator were designated as Y23/101-55, Y23/101-57, Y23/101-59, Y23/81/101-4, Y23/85/101-13, Y23/85/101-14, Y23/85/101-19, Y23/86/101-23, Y23/95/101-1, Y23/95/101-2, Y23/81/95/101-20, Y23/85/95/101-7 and Y23/85/95/101-8.

Example 38A

Figure 13:
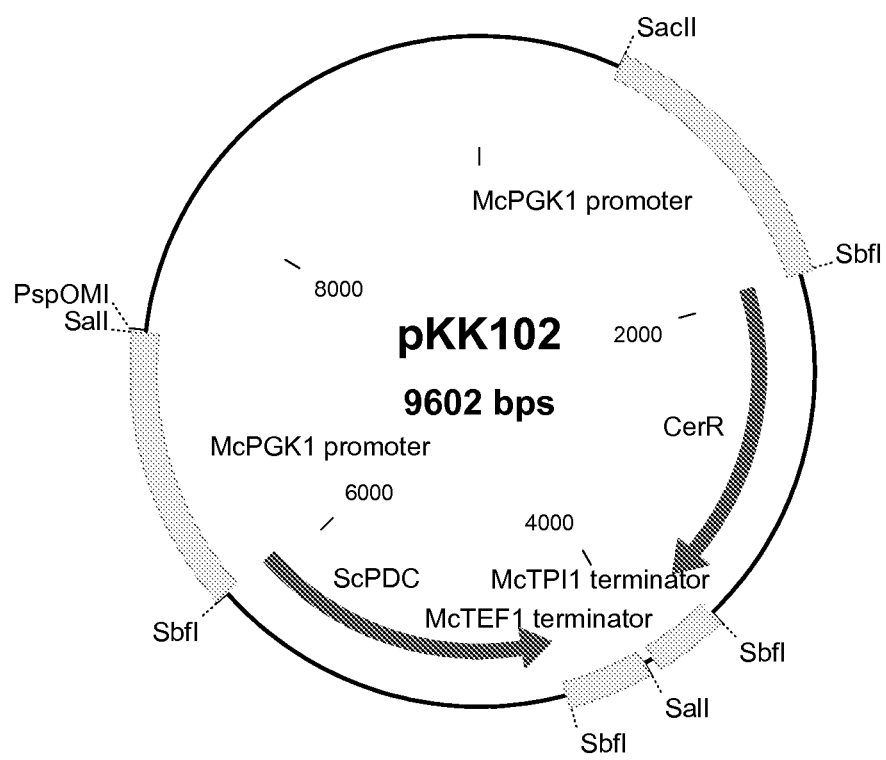
FIG. 13 is a diagram depicting plasmid pKK102.

Construction of a Plasmid (pKK102) Containing the Cerulenin Resistance Gene Under the Control of the McPGK1 Promoter and the McTPI1 Terminator and the *S. cerevisiae* PDC1 Encoding Gene Under the Control of the McPGK1 Promoter and the McTEF1 Terminator The plasmid M22_PGKp-PDC-TEFt (Geneart AG, Germany) contains a *S. cerevisiae* PDC1 (SEQ ID NO:95) encoding gene which has been codon optimized according to *Rhizopus oryzae* filamentous fungus codon usage (SEQ ID NO:97) with the McPGK1 promoter and the McTEF1 terminator. Plasmid M22_PGKp-PDC-TEFt was digested with SalI. A 3363 bp fragment was gel isolated and ligated to a 6239 bp fragment obtained by digesting a plasmid designated pKK92 (Ex. 14B) with SalI. The resulting plasmid was designated as pKK102 (FIG. 13). The plasmid pKK102 contains a *S. cerevisiae* PDC1 encoding gene under the control of the McPGK1 promoter and the McTEF1 terminator and the *S. cerevisiae* cerulenin resistance gene under the control of the McPGK1 promoter and the McTPI1 terminator.

Example 38B

Generation of a Genetically Modified *Mucor circinelloides* (M22/94/102) with Integrated ALD6, ACS1 and PDC1 Encoding Genes and Hygromycin and Cerulenin Resistance Genes by Transforming Genetically Modified Strain M22/94-12 (Ex. 16B) with Digested Plasmid pKK102 (FIG. 13, Ex. 38A)

Plasmid pKK102 was restricted with SacII and PspOMI, and the resulting linear DNA was used to transform the genetically modified strain M22/94-12, using the transformation method described in Example 15B. The transformed cells were screened for cerulenin resistance. Several cerulenin resistant colonies were analysed at DNA level by PCR. The transformant originating from the transformation of the genetically modified strain M22/94-12 with SacII and PspOMI cut pKK102 and containing the *S. cerevisiae* PDC1 encoding gene under the control of the McPGK1 promoter and the McTEF1 terminator was designated as M22/94/102-31.

Example 39

Aerobic Shake Flask Characterization of Strains Y23/101-59 (Ex. 37B), Y23/81/101-4 (Ex. 37B), Y23/85/101-14 (Ex. 37B), Y23/86/101-23 (Ex. 37B), Y23/95/101-2 (Ex. 37B), Y23/81/95/101-20 (Ex. 37B) and Y23/85/95/101-9 (Ex. 37B) in Glucose Medium with C/N Ratio of 153

Transformants were separately cultivated in 50 ml of Glucose-CN153 medium (pH 5.5, 30 g glucose, 0.15 g $(NH_4)_2SO_4$, 7.0 g $KH_2PO_4$, 2.5 g $Na_2HPO_4*2\ H_2O$, 1.5 g $MgSO_4*7H_2O$, 0.45 g Yeast extract, 51 mg $CaCl_2$, 8 mg $FeCl_3*6\ H_2O$ and 0.1 mg $ZnSO_4*7\ H_2O$ per liter). Each flask (250 ml) was inoculated to an $OD_{600}$ of 0.3 with cells grown on yeast peptone plus glucose plates. The cultivations were maintained at a temperature of 30° C. with shaking at 250 rpm. Samples for cell dry weight measurement, lipid extraction and HPLC analysis were withdrawn periodically during cultivation. *Cryptococcus curvatus* wild type strain Y23 was used as a control. Cell dry weight was determined and HPLC analysis was carried out as described in Example 22. Lipid extraction and triacylglycerol measurements as described in Example 21. Lipid extractions from the culture medium i.e. from the supernatant samples recovered after centrifugation of the cell lipid extraction samples or dry weight measurement samples were carried out as follows. To 150 µl of supernatant sample 150 µl of 0.9% NaCl and 150-1500 µl of chloroform:methanol (2:1) was added. The sample was vortexed 2 minutes and sample was incubated at room temperature at 30 min. After incubation sample was centrifuged 10000 rpm for 3 min at RT. The lower phase was recovered into microfuge tubes, dried and redissolved in 1.5 ml of chloroform:methanol (2:1) and stored at −20° C. prior triacylglycerol measurements as described in Example 21. Alternatively, dried lipid pellet was redissolved directly in isopropanol and triacylglycerol was measured as described in Example 21.

After 47 hours cultivation (Table 18), when 17 to 18 g/l glucose was left, Y23/101-59, Y23/85/101-14, Y23/86/101-23, Y23/95/101-2, Y23/81/95/101-20 and Y23/85/95/101-8 transformants produced 52, 78, 9, 27, 32 and 48% more triacylglycerol with higher rate, respectively, than the control strain in glucose medium. Also triacylglycerol yields on biomass and per used glucose were 33 to 83% and 35 to 85% higher in transformants Y23/101-59, Y23/85/101-14, Y23/86/101-23, Y23/95/101-2, Y23/81/95/101-20 and Y23/85/95/101-8 than the control strain, respectively.

TABLE 18

Triacylglycerol (TAG) concentration (g/l), rate (mg/l/h) and yield (%) per biomass (CDW) and used glucose in the yeast cells after 47 hours cultivation in glucose medium with C/N ratio of 153

| Strain | TAG (g/l) | Yield TAG (% CDW) | Yield TAG (% used glucose) | TAG mg/l/h |
|---|---|---|---|---|
| Control | 1.30 | 22.5 | 10.9 | 28 |
| Y23/101-59 (PDC) | 1.98 | 37.1 | 16.3 | 42 |
| Y23/85/101-14 (PDC + ALD + ACS) | 2.31 | 41.1 | 20.2 | 49 |
| Y23/86/101-23 (PDC + ACS) | 1.42 | 29.8 | 15.4 | 30 |
| Y23/95/101-2 (PDC + PDAT) | 1.65 | 30.9 | 14.7 | 35 |
| Y23/81/95/101-20 (PDC + ALD + PDAT) | 1.72 | 36.4 | 16.4 | 37 |
| Y23/85/95/101-8 (PDC + ALD + ACS + PDAT) | 1.93 | 36.6 | 18.1 | 41 |

After 94 hours cultivation (Table 19A), when 6 to 11 g/l glucose was left, Y23/101-59, Y23/85/101-14, Y23/81/95/101-20 and Y23/85/95/101-8 transformants produced 5, 27, 8 and 12% more triacylglycerol with higher rate, respectively, than the control strain in glucose medium. Also triacylglycerol yields on biomass and per used glucose were 9 to 33% and 7 to 38% higher in transformants Y23/101-59, Y23/81/101-4, Y23/85/101-14, Y23/86/101-23, Y23/95/101-2, Y23/81/95/101-20 and Y23/85/95/101-8 than the control strain, respectively. Additionally, triacylglycerol concentration in the culture medium in the cultivations with the transformants Y23/81/101-4 and Y23/86/101-23 was 525 and 350% higher, respectively, than in the cultivation with the control strain (Table 19B). Additionally, the total triacylglycerol yields per used glucose calculated from the intracellular triacylglycerol concentration and the triacylglycerol concentration detected from the culture medium were 13 to 38% higher with the transformants than with the control strain.

TABLE 19A

Triacylglycerol (TAG) concentration (g/l), rate (mg/l/h) and yield (%) per biomass (CDW) and used glucose in the yeast cells after 94 hours cultivation in glucose medium with C/N ratio of 153

| Strain | TAG (g/l) | Yield TAG (% CDW) | Yield TAG (% used glucose) | TAG mg/l/h |
|---|---|---|---|---|
| Control | 4.06 | 43.4 | 17.4 | 43 |
| Y23/101-59 (PDC) | 4.28 | 51.6 | 19.9 | 46 |
| Y23/81/101-4 (PDC + ALD) | 3.39 | 55.7 | 18.6 | 36 |
| Y23/85/101-14 (PDC + ALD + ACS) | 5.17 | 57.9 | 22.7 | 55 |
| Y23/86/101-23 (PDC + ACS) | 4.00 | 53.4 | 21.1 | 43 |
| Y23/95/101-2 (PDC + PDAT) | 3.50 | 47.5 | 20.1 | 37 |
| Y23/81/95/101-20 (PDC + ALD + PDAT) | 4.38 | 62.0 | 24.0 | 47 |
| Y23/85/95/101-8 (PDC + ALD + ACS + PDAT) | 4.55 | 54.4 | 21.5 | 48 |

TABLE 19B

Triacylglycerol (TAG) concentration (g/l) in the culture medium and calculated total TAG concentration (g/l), rate (mg/l/h) and yield (%) per used glucose in cultivation after 94 hours cultivation in glucose medium with C/N ratio of 153

| Strain | TAG (g/l) | Total TAG (g/l) | Yield total TAG (% used glucose) | total TAG mg/l/h |
|---|---|---|---|---|
| Control | 0.04 | 4.10 | 17.6 | 44 |
| Y23/101-59 (PDC) | 0.01 | 4.29 | 20.0 | 46 |
| Y23/81/101-4 (PDC + ALD) | 0.25 | 3.63 | 19.9 | 39 |
| Y23/85/101-14 (PDC + ALD + ACS) | 0.03 | 5.20 | 22.8 | 55 |
| Y23/86/101-23 (PDC + ACS) | 0.18 | 4.18 | 22.1 | 44 |
| Y23/95/101-2 (PDC + PDAT) | 0.01 | 3.51 | 20.2 | 37 |
| Y23/81/95/101-20 (PDC + ALD + PDAT) | 0.03 | 4.42 | 24.2 | 47 |
| Y23/85/95/101-8 (PDC + ALD + ACS + PDAT) | 0.04 | 4.6 | 21.7 | 49 |

This example shows that expression of PDC1, ALD6, ACS2 and PDAT genes in different combinations enhanced triacylglycerol concentrations and rates of production and triacylglycerol yields from used glucose or per dry weight in the yeast cell and/or in the culture medium with high C/N ratio in different stages of the cultivation.

Example 40

Aerobic Shake Flask Characterization of Strains Y23/101-55 (Ex. 37B), Y23/81/101-4 (Ex. 37B), Y23/85/101-19 (Ex. 37B), Y23/86/101-23 (Ex. 37B), Y23/95/101-2 (Ex. 37B) and Y23/85/95/101-7 (Ex. 37B) in Glucose Medium with C/N Ratio of 28

Transformants were separately cultivated in 50 ml of Glucose-CN28 medium (pH 5.5, 30 g glucose, 0.3 g $(NH_4)_2SO_4$, 7.0 g $KH_2PO_4$, 2.5 g $Na_2HPO_4*2\ H_2O$, 1.5 g $MgSO_4*7H_2O$, 4.0 g Yeast extract, 51 mg $CaCl_2$, 8 mg $FeCl_3*6\ H_2O$ and 0.1 mg $ZnSO_4*7\ H_2O$ per liter). Each flask (250 ml) was inoculated to an $OD_{600}$ of 0.3 with cells grown on yeast peptone plus glucose plates. The cultivations were maintained at a temperature of 30° C. with shaking at 250 rpm. Samples for cell dry weight measurement, lipid extraction and HPLC analysis were withdrawn periodically during cultivation. *Cryptococcus curvatus* wild type strain Y23 was used as a control. Cell dry weight was determined and HPLC analysis was carried out as described in Example 22. Lipid extraction from the yeast cells and triacylglycerol measurements were carried out as described in Example 21 and lipid extraction from the culture medium as described in Example 39.

After 46 hours cultivation (Table 20A), when 12 to 14 g/l glucose was left, Y23/101-55, Y23/81/101-4, Y23/85/101-19, Y23/86/101-23, Y23/95/101-2 and Y23/85/95/101-7 transformants produced 18, 17, 20, 24, 7 and 17% more triacylglycerol with higher rate, respectively, than the control strain in glucose medium. Also triacylglycerol yields on biomass and per used glucose were 10 to 35% and 7 to 26% higher with the transformants than the control strain, respectively. After 72 and 94 hours cultivation triacylglycerol concentration in the culture medium with the transformants Y23/81/101-4 and Y23/86/101-23 was 195 and 56% and 35 and 30% higher, respectively, than in the cultivations with the control strain (Table 20B). Additionally, yield of triacylglycerol detected in culture medium per used glucose was 57 to 206% and 36 to 56% higher with the transformants Y23/81/101-4 and Y23/86/101-23 than with the control after 72 and 94 hours cultivation, respectively.

TABLE 20A

Triacylglycerol (TAG) concentration (g/l), rate (mg/l/h) and yield (%) per biomass (CDW) and used glucose in the yeast cells after 46 hours cultivation in glucose medium with C/N ratio of 28

| Strain | TAG (g/l) | Yield TAG (% CDW) | Yield TAG (% used glucose) | TAG mg/l/h |
|---|---|---|---|---|
| Control | 3.10 | 46.6 | 20.6 | 67 |
| Y23/101-55 (PDC) | 3.67 | 51.2 | 24.4 | 80 |
| Y23/81/101-4 (PDC + ALD) | 3.64 | 53.5 | 22.1 | 79 |
| Y23/85/101-19 (PDC + ALD + ACS) | 3.71 | 53.8 | 23.2 | 81 |
| Y23/86/101-23 (PDC + ACS) | 3.84 | 63.1 | 26.0 | 83 |
| Y23/95/101-2 (PDC + PDAT) | 3.31 | 54.7 | 23.3 | 72 |
| Y23/85/95/101-7 (PDC + ALD + ACS + PDAT) | 3.64 | 58.5 | 26.3 | 79 |

TABLE 20B

Triacylglycerol (TAG) concentration (g/l) and yield (%) per used glucose in the culture medium after 72 and 94 hours cultivation in glucose medium with C/N ratio of 28

| Strain | 72 h TAG (g/l) | Yield TAG % (/used glucose) | 94 h TAG (g/l) | Yield TAG (% used glucose) |
|---|---|---|---|---|
| Control | 0.85 | 3.19 | 2.79 | 9.84 |
| Y23/81/101-4 (PDC + ALD) | 2.51 | 9.75 | 4.35 | 15.4 |
| Y23/86/101-23 (PDC + ACS) | 1.15 | 5.00 | 3.62 | 13.4 |

This example shows that expression of PDC1, ALD6, ACS2 and PDAT genes in different combinations enhanced triacylglycerol concentrations and rates of production and triacylglycerol yields from used glucose or per dry weight in the yeast cell and/or in the culture medium with low C/N ratio at different stages of the cultivation.

Example 41

Aerobic Shake Flask Characterization of Strains Y23/101-57 (Ex. 37B), Y23/81/101-4 (Ex. 37B), Y23/85/101-13 (Ex. 37B), Y23/86/101-23 (Ex. 37B), Y23/95/101-1 (Ex. 37B), Y23/81/95/101-20 (Ex. 37B) and Y23/85/95/101-8 (Ex. 37B) in Xylose Medium with C/N Ratio of 103

Transformants were separately cultivated in 50 ml of Yeast culture medium IV (pH 5.5, 20 g xylose, 0.15 g $(NH_4)_2SO_4$, 7.0 g $KH_2PO_4$, 2.5 g $Na_2HPO_4*2\ H_2O$, 1.5 g $MgSO_4*7H_2O$, 0.45 g Yeast extract, 51 mg $CaCl_2$, 8 mg $FeCl_3*6\ H_2O$ and 0.1 mg $ZnSO_4*7\ H_2O$ per liter). Each flask (250 ml) was inoculated to an $OD_{600}$ of 0.3 with cells grown on yeast peptone plus xylose plates. The cultivations were maintained at a temperature of 30° C. with shaking at 250 rpm. Samples for cell dry weight measurement, lipid extraction and HPLC analysis were withdrawn periodically during cultivation. *Cryptococcus curvatus* wild type strain Y23 was used as a control. Cell dry weight was determined and HPLC analysis was carried out as described in Example 22. Lipid extraction from the yeast cells and triacylglycerol measurements were carried out as described in Example 21 and lipid extraction from the culture medium as described in Example 39.

After 47 hours cultivation (Table 21) Y23/101-57, Y23/81/101-4, Y23/85/101-13 and Y23/95/101-1 transformants produced 12, 18, 4 and 5% more triacylglycerol with higher rate, respectively, than the control strain in xylose medium. Also triacylglycerol yields on biomass and per used xylose were up to 28% and 16% higher with the transformants Y23/101-57, Y23/81/101-4, Y23/85/101-13, Y23/86/101-23 and Y23/95/101-1 than the control strain, respectively. Also total lipid concentration, rate and yields on biomass and per used xylose were 8 to 29%, 8 to 29%, 19 to 44% and 11 to 33% higher with the transformants than the control strain, respectively, after 47 hours cultivation in xylose medium.

TABLE 21

Triacylglycerol (TAG) and total lipid concentrations (g/l), rates (mg/l/h) and yields (%) per biomass (CDW) and used xylose in the yeast cells after 47 hours cultivation in xylose medium with C/N ratio of 103

| Strain | TAG (g/l) | Yield TAG (% CDW) | Yield TAG (% used xylose) | TAG mg/l/h |
|---|---|---|---|---|
| Control | 1.90 | 38.5 | 16.0 | 41 |
| Y23/101-57 (PDC) | 2.12 | 44.7 | 18.0 | 45 |
| Y23/81/101-4 (PDC + ALD) | 2.24 | 49.2 | 18.6 | 48 |
| Y23/85/101-13 (PDC + ALD + ACS) | 1.98 | 44.3 | 18.1 | 42 |
| Y23/86/101-23 (PDC + ACS) | 1.85 | 47.7 | 18.3 | 39 |
| Y23/95/101-1 (PDC + PDAT) | 2.00 | 38.5 | 16.5 | 43 |

| Strain | Lipid (g/l) | Yield lipid (% CDW) | Yield lipid (% used xylose) | Lipid mg/l/h |
|---|---|---|---|---|
| Control | 2.40 | 48.5 | 20.2 | 51 |
| Y23/101-57 (PDC) | 2.75 | 57.9 | 23.3 | 59 |
| Y23/81/101-4 (PDC + ALD) | 2.70 | 59.3 | 22.4 | 57 |
| Y23/85/101-13 (PDC + ALD + ACS) | 2.60 | 58.1 | 23.7 | 55 |
| Y23/86/101-23 (PDC + ACS) | 2.70 | 69.7 | 26.8 | 57 |
| Y23/95/101-1 (PDC + PDAT) | 3.10 | 59.6 | 25.6 | 66 |

After 94 hours cultivation (Table 22A) Y23/101-57, Y23/81/101-4, Y23/85/101-13, Y23/86/101-23, Y23/95/101-1, Y23/81/95/101-20 and Y23/85/95/101-8 transformants produced 7, 9, 8, 7, 6, 6 and 4% more triacylglycerol with higher rate, respectively, than the control strain in xylose medium. Also triacylglycerol yields on biomass and per used xylose were 4 to 25% and 5 to 17% higher with the transformants than the control strain, respectively. Triacylglycerol concentration in the culture medium with the transformants Y23/81/101-4 and Y23/86/101-23 was 222 and 156% higher, respectively, than in the cultivations with the control strain (Table 22B). Additionally, the total triacylglycerol yields per used xylose calculated from the intracellular triacylglycerol concentration and the triacylglycerol concentration detected from the culture medium were 7 to 17% higher with the transformants than with the control strain.

TABLE 22A

Triacylglycerol (TAG) concentration (g/l), rate (mg/l/h) and yield (%) per biomass (CDW) and used xylose in the yeast cells after 94 hours cultivation in xylose medium with C/N ratio of 103

| Strain | TAG (g/l) | Yield TAG (% CDW) | Yield TAG (% used xylose) | TAG mg/l/h |
|---|---|---|---|---|
| Control | 4.50 | 72.0 | 23.9 | 48 |
| Y23/101-57 (PDC) | 4.82 | 79.4 | 25.6 | 51 |
| Y23/81/101-4 (PDC + ALD) | 4.92 | 84.2 | 26.1 | 52 |
| Y23/85/101-13 (PDC + ALD + ACS) | 4.85 | 75.1 | 25.7 | 52 |
| Y23/86/101-23 (PDC + ACS) | 4.82 | 88.5 | 25.6 | 51 |
| Y23/95/101-1 (PDC + PDAT) | 4.79 | 79.8 | 25.7 | 51 |
| Y23/81/95/101-20 (PDC + ALD + PDAT) | 4.78 | 89.7 | 27.9 | 51 |
| Y23/85/95/101-8 (PDC + ALD + ACS + PDAT) | 4.66 | 80.4 | 25.2 | 50 |

TABLE 22B

Triacylglycerol (TAG) concentration (g/l) in the culture medium and calculated total TAG concentration (g/l), rate (mg/l/h) and yield (%) per used xylose in cultivation after 94 hours cultivation in xylose medium with C/N ratio of 103

| Strain | TAG (g/l) | Total TAG (g/l) | Yield total TAG (% used xylose) | total TAG mg/l/h |
|---|---|---|---|---|
| Control | 0.09 | 4.59 | 24.3 | 49 |
| Y23/101-57 (PDC) | 0.07 | 4.89 | 26.0 | 52 |
| Y23/81/101-4 (PDC + ALD) | 0.29 | 5.22 | 27.7 | 55 |
| Y23/85/101-13 (PDC + ALD + ACS) | 0.10 | 4.94 | 26.2 | 53 |
| Y23/86/101-23 (PDC + ACS) | 0.23 | 5.05 | 26.8 | 54 |
| Y23/95/101-1 (PDC + PDAT) | 0.07 | 4.86 | 26.1 | 52 |
| Y23/81/95/101-20 (PDC + ALD + PDAT) | 0.09 | 4.86 | 28.4 | 52 |
| Y23/85/95/101-8 (PDC + ALD + ACS + PDAT) | 0.10 | 4.76 | 25.7 | 51 |

This example shows that expression of PDC1, ALD6, ACS2 and PDAT genes in different combinations enhanced triacylglycerol and total lipid concentrations and rates of production and triacylglycerol and total lipid yields from used xylose or per dry weight in the yeast cell and/or in the culture medium with high C/N ratio in different stages of the cultivation.

Example 42

Aerobic Shake Flask Characterization of Strains Y23/101-57 (Ex. 37B), Y23/85/101-13 (Ex. 37B) and Y23/81/95/101-20 (Ex. 37B) in Xylose Medium with C/N Ratio of 20

Transformants were separately cultivated in 50 ml of Xylose-CN20 medium (pH 5.5, 20 g xylose, 0.3 g $(NH_4)_2SO_4$, 7.0 g $KH_2PO_4$, 2.5 g $Na_2HPO_4*2\ H_2O$, 1.5 g $MgSO_4*7H_2O$, 4.0 g Yeast extract, 51 mg $CaCl_2$, 8 mg $FeCl_3*6\ H_2O$ and 0.1 mg $ZnSO_4*7\ H_2O$ per liter). Each flask (250 ml) was inoculated to an $OD_{600}$ of 0.3 with cells grown on yeast peptone plus xylose plates. The cultivations were maintained at a temperature of 30° C. with shaking at 250 rpm. Samples for cell dry weight measurement, lipid extraction and HPLC analysis were withdrawn periodically during cultivation. *Cryptococcus curvatus* wild type strain Y23 was used as a control. Cell dry weight was determined and HPLC analysis was carried out as described in Example 22. Lipid extraction from the yeast cells and triacylglycerol measurements were carried out as described in Example 21 and lipid extraction from the culture medium as described in Example 39.

After 94 hours cultivation (Table 23A) transformants Y23/101-57 and Y23/85/101-13 produced 9 and 5% more triacylglycerol with higher rate, respectively, than the control strain in xylose medium. Also triacylglycerol yields on biomass and per used xylose were 2 to 10% and 4 to 8% higher with the transformants than the control strain, respectively. Triacylglycerol concentration in the culture medium with the transformants Y23/101-57, Y231851101-13 and Y23/81/95/101-20 was 163, 163 and 188% higher, respectively, than in the cultivations with the control strain (Table 21 B). Additionally, the total triacylglycerol yields per used xylose calculated from the intracellular triacylglycerol concentration and the triacylglycerol concentration detected from the culture medium were 4 to 12% higher with the transformants than with the control strain.

TABLE 23A

Triacylglycerol (TAG) concentration (g/l) and yield (%) per biomass (CDW) and used xylose in the yeast cells after 94 hours cultivation in xylose medium with C/N ratio of 20

| Strain | TAG (g/l) | Yield TAG (% CDW) | Yield TAG (% used xylose) |
|---|---|---|---|
| Control | 4.21 | 68.7 | 21.1 |
| Y23/101-57 (PDC) | 4.57 | 75.8 | 22.8 |
| Y23/85/101-13 (PDC + ALD + ACS) | 4.41 | 69.9 | 22.0 |

TABLE 23B

Triacylglycerol (TAG) concentration (g/l) in the culture medium and calculated total TAG concentration (g/l), rate (mg/l/h) and yield (%) per used xylose in cultivation after 94 hours cultivation in xylose medium with C/N ratio of 20

| Strain | TAG (g/l) | Total TAG (g/l) | Yield total TAG (% used xylose) | total TAG mg/l/h |
|---|---|---|---|---|
| Control | 0.08 | 4.28 | 21.4 | 46 |
| Y23/101-57 (PDC) | 0.21 | 4.78 | 23.9 | 51 |
| Y23/85/101-13 (PDC + ALD + ACS) | 0.21 | 4.61 | 23.1 | 49 |
| Y23/81/95/101-20 (PDC + ALD + PDAT) | 0.23 | 4.45 | 22.3 | 47 |

This example shows that expression of PDC1, ALD6, ACS2 and PDAT genes in different combinations enhanced triacylglycerol concentrations and rates of production and triacylglycerol yields from used xylose or per dry weight in the yeast cell and/or in the culture medium with low C/N ratio.

Example 43

Aerobic Shake Flask Characterization of Strains M22/94-16 (Ex. 16B) and M22/94/102-31 (Ex. 38B), in Xylose Medium with C/N Ratio of 21

Transformants were separately cultivated in 50 ml of mould C/N 21 medium (pH 5.5, 10 g glucose, 1.4 g yeast extract, 2.5 g $KH_2PO_4$, 0.3 g $(NH_4)_2SO_4$, 10 mg $ZnSO_4*7H_2O$, 2 mg $CuSO_4.5H_2O$, 10 mg $MnSO_4$, 0.5 g $MgSO_4*7 H_2O$, 0.1 g $CaCl_2$, 20 mg $FeCl_3*6H_2O$ per liter). Each flask (250 ml) was inoculated with $1*10^7$ spores. The cultivations were maintained at a temperature of 28° C. with shaking at 250 rpm. Samples for cell dry weight measurement, lipid extraction and HPLC analysis were withdrawn periodically during cultivation. *Mucor circinelloides* wild type strain M22 was used as a control. Cell dry weight was determined as described in Example 25 and HPLC analysis was carried out as described in Example 22. Lipid extraction and total lipid and triacylglycerol measurements as described in Example 21.

After 96 hours cultivation (Table 24) transformants M22/94-16 and M22/94/102-31 produced 18 and 30% more triacylglycerol with higher rate, respectively, than the control strain in xylose medium. Also triacylglycerol yields on biomass and per used xylose were 10 to 34% and 1 to 24% higher with the transformants than the control strain, respectively. Also total lipid concentration and yield on biomass were 15 to 16% and 6 to 33% higher in the transformants than in the control.

TABLE 24

Triacylglycerol (TAG) and total lipid concentrations (g/l), rates (mg/l/h) and yields (%) per biomass (CDW; cell dry weight) and used xylose after 96 hours cultivation in xylose medium with C/N ratio of 21

| Strain | TAG g/l | Yield TAG (% CDW) | Yield TAG (% used xylose) | TAG mg/l/h |
|---|---|---|---|---|
| Control | 0.60 | 34.9 | 13.9 | 6 |
| M22/94-16 (ALD + ACS) | 0.71 | 38.4 | 14.0 | 7 |
| M22/94/102-31 (PDC + ALD + ACS) | 0.78 | 53.2 | 17.2 | 8 |

| Strain | Lipid g/l | Yield lipid (% CDW) | Yield lipid (% used xylose) | Lipid mg/l/h |
|---|---|---|---|---|
| Control | 0.81 | 47.6 | 18.9 | 8 |
| M22/94-16 (ALD + ACS) | 0.94 | 50.5 | 18.5 | 10 |
| M22/94/102-31 (PDC + ALD + ACS) | 0.93 | 63.5 | 20.5 | 10 |

This example shows that expression of PDC1, ALD6 and ACS2 genes in different combinations enhanced triacylglycerol and total lipid concentrations and rates of production and triacylglycerol and total lipid yields from used xylose or per dry weight in the yeast cell culture mewith low C/N ratio.

Example 44

Production of Triacylglycerol or Lipid by Strains of *C. curvatus* Modified by Addition of Genes Encoding PDC and ALD and PDAT and ACS (Y23/85/95/101-8, Ex. 37B) in High Cell Density Cultures Grown on Glucose with C/N Ratio of 28

Transformant (Y23/85/95/101-8) was cultivated in Multifors bioreactors (max. working volume 500 ml, Infors HT, Switzerland) at pH 4.0, 30° C., in 500 ml medium containing 90 to 96 g glucose, 6.74 g $(NH_4)_2SO_4$, 1.2 g $KH_2PO_4$, 0.3 g $Na_2HPO_4.2H_2O$, 1.5 g $MgSO_4.7H_2O$, 0.1 g $CaCl_2.6H_2O$, 5.26 mg citric acid.$H_2O$, 5.26 mg $ZnSO_4.7H_2O$, 0.1 mg $MnSO_4.4H_2O$, 0.5 mg $CoCl_2.6H_2O$, 0.26 mg $CuSO_4.5H_2O$, 0.1 mg $Na_2MoO_4.2H_2O$, 1.4 mg $FeSO_4.7H_2O$, 0.1 mg $H_3BO_4$, 0.05 mg D-biotin, 1.0 mg CaPantothenate, 5.0 mg nicotinic acid, 25 mg myoinositol, 1.0 mg thiamine.HCl, 1.0 mg pyridoxine.HCl and 0.2 mg p-aminobenzoic acid per liter. The pH was maintained constant by addition of 1 M KOH or 1 M $H_2PO_4$. Cultures were agitated at 1000 rpm (2 Rushton turbine impellors) and aerated at 2 volumes air per volume culture per minute (vvm). Clerol FBA 3107 antifoaming agent (Cognis, Saint-Fargeau-Ponthierry Cedex France, 1 ml $l^{-1}$) was added to prevent foam accumulation. Bioreactors were inoculated to initial $OD_{600}$ of 0.5 to 4.0 with cells grown in the same medium (substituting 1.5 g urea per liter for $(NH_4)_2SO_4$ and omitting the $CaCl_2.6H_2O$) in 50 ml volumes in 250 ml flasks at 30° C. with shaking at 200 rpm for 24 to 42 h. Samples for cell dry weight measurement, lipid extraction and HPLC analysis were withdrawn periodically during cultivation. *Cryptococcus curvatus* wild type strain Y23 was used as the control.

Lipid extraction and triacylglycerol concentration measurements were carried out as described in Example 21. Lipid extraction from the culture medium was carried out as described in Example 39. Cell dry weight was determined as described in Example 30. HPLC analyses were carried out as described in Example 22.

Table 25A shows that a transformant containing the genes PDC, ALD, ACS and PDAT produced 58% more triacylglycerol than Y23, with a 67% and 185% increase in the yields on glucose consumed and on biomass, respectively. Additionally, the transformant containing the genes PDC, ALD, ACS and PDAT produced 20% more triacylglycerol than Y23, with a 111% increase in the yield on glucose consumed in the culture medium (Table 25B).

TABLE 25A

Triacylglycerol produced in pH controlled bioreactor culture of Y23 and transformant of Y23 expressing PDC + ALD + ACS + PDAT, with glucose as carbon source and C/N 28. Data is the average of 2 cultures ± standard error of the mean. Percentage increase is shown in parenthesis.

| Strain | TAG (g/l) | Yield TAG (% glucose consumed) | Yield TAG (% per CDW) |
|---|---|---|---|
| Y23 | 1.30 ± 0.06 | 1.22 ± 0.01 | 2.67 ± 0.14 |
| Y23/85/95/101-8 (PDC + ALD + ACS + PDAT) | 2.05 ± 0.34 (+58%) | 2.04 ± 0.22 (+67%) | 4.95 ± 0.33 (+185%) |

TABLE 25B

Triacylglycerol produced in the culture medium in pH controlled bioreactor culture of Y23 and transformant of Y23 expressing PDC + ALD + ACS + PDAT, with glucose as carbon source and C/N 28. Data is the average of 2 cultures ± standard error of the mean. Percentage increase is shown in parenthesis.

| Strain | TAG (g/l) | Yield TAG (% glucose consumed) |
|---|---|---|
| Y23 | 0.15 ± 0.04 | 0.18 ± 0.03 |
| Y23/85/95/101-8 (PDC + ALD + ACS + PDAT) | 0.18 ± 0.00 (+20%) | 0.38 ± 0.07 (+111%) |

This example shows that expression of PDC1, ALD6, ACS1 and PDAT enhanced triacylglycerol concentrations and triacylglycerol yields from used glucose or per dry weight in high cell density cultures in the yeast cell and/or in the culture medium.

Sequences Used:

SEQ ID NOs: 1 and 2 correspond to primers YeastTEF1 and YeastTEF4, respectively, used to isolate genomic fragment of the *C. curvatus* TEF gene.

SEQ ID NOs: 3 and 4 correspond to primers PCR linker I and PCR linker II, respectively, used in chromosome walk experiments.

SEQ ID NOs: 5, 6, 7 and 8 correspond to primers CC_TEF2, CC_TEF1, CC_TEF6 and CC_TEF5 respectively, used to isolate genomic fragments of the *C. curvatus* TEF promoter region in chromosome walk experiments.

SEQ ID NOs: 9 and 10 correspond to primers CC_TEF10 and CC_TEF11, respectively, used to isolate promoter of the *C. curvatus* TEF gene.

SEQ ID NOs: 11 and 12 correspond to primers CC_TEF3 and CC_TEF4, respectively, used to isolate genomic fragment of the *C. curvatus* TEF terminator region in chromosome walk experiments.

SEQ ID NOs: 13 and 14 correspond to primers CC_TEF7 and CC_TEF8, respectively, used to isolate terminator of the *C. curvatus* TEF gene.

SEQ ID NOs: 15 and 16 correspond to primers Yeast TPI5 and Yeast TPI8, respectively, used to isolate genomic fragment of the *C. curvatus* TPI gene.

SEQ ID NOs: 17 and 18 correspond to primers CC_TPI2 and CC_TPI1, respectively, used to isolate genomic fragment of the *C. curvatus* TPI promoter region in chromosome walk experiments.

SEQ ID NOs: 19 and 20 correspond to primers CC_TPI7 and CC_TPI9, respectively, used to isolate promoter of the *C. curvatus* TPI gene.

SEQ ID NOs: 21 and 22 correspond to primers CC_TPI4 and CC_TPI3, respectively, used to isolate genomic fragment of the *C. curvatus* TPI terminator region in chromosome walk experiments.

SEQ ID NOs: 23 and 24 correspond to primers CC_TPI5 and CC_TPI6, respectively, used to isolate terminator of the *C. curvatus* TPI gene.

SEQ ID NOs: 25 and 26 correspond to primers Yeast-ENO5 and YeastENO10, respectively, used to isolate genomic fragment of the *C. curvatus* ENO gene.

SEQ ID NOs: 27, 28, 29 and 30 correspond to primers CC_ENO$_2$, CC_ENO1, CC_ENO5 and CC_ENO6, respectively, used to isolate genomic fragments of the *C. curvatus* ENO promoter region in chromosome walk experiments.

SEQ ID NOs: 31 and 32 correspond to primers CC_ENO9 and CC_ENO10, respectively, used to isolate promoter of the *C. curvatus* ENO gene.

SEQ ID NOs: 33 and 34 correspond to primers CC_ENO4 and CC_ENO3, respectively, used to isolate genomic fragment of the *C. curvatus* ENO terminator region in chromosome walk experiments.

SEQ ID NOs: 35 and 36 correspond to primers CC_ENO7 and CC_ENO8, respectively, used to isolate terminator of the *C. curvatus* ENO gene.

SEQ ID NOs: 37 and 38 correspond to primers CC_GPD3 and CC_GPD4, respectively, used to isolate genomic fragment of the *C. curvatus* GPD terminator region in chromosome walk experiments.

SEQ ID NOs: 39 and 40 correspond to primers CC_GPD6 and CC_GPD7, respectively, used to isolate terminator of the *C. curvatus* GPD gene.

SEQ ID NOs: 41 and 42 correspond to primers Hph 5 and Hph 3, respectively, used to isolate *E. coli* hygromycin gene.

SEQ ID NOs: 43 and 44 correspond to primers Kan 5 and Kan 3, respectively, used to isolate *E. coli* G418 resistance gene.

SEQ ID NOs: 45 and 46 correspond to primers CERR 5 and CERR 3, respectively, used to isolate *S. cerevisiae* cerulenin resistance gene.

SEQ ID NO: 47 corresponds to the amino acid sequence of the *S. cerevisiae* ALD6 gene, with GenBank accession number AAB68304 (version number AAB68304.1).

SEQ ID NO: 48 corresponds to *S. cerevisiae* ALD6 protein encoding DNA codon optimized according to *Ustilago maydis*-fungus codon usage.

SEQ ID NO: 49 corresponds to *S. cerevisiae* ALD6 protein encoding DNA codon optimized according to *Rhizopus oryzae*-filamentous fungus codon usage.

SEQ ID NO: 50 corresponds to the amino acid sequence of the *S. cerevisiae* ACS2 gene, with GenBank accession number CAA97725 (version number CAA97725.1.

SEQ ID NO: 51 corresponds to *S. cerevisiae* ACS2 protein encoding DNA codon optimized according to *Ustilago maydis*-fungus codon usage.

SEQ ID NO: 52 corresponds to the amino acid sequence of the *Rhizopus oryzae* PDAT gene, encoded by gene with locus number RO3G_07851.3 in Broad Institute *Rhizopus oryzae* database.

SEQ ID NO: 53 corresponds to *Rhizopus oryzae* PDAT protein encoding DNA codon optimized according to *Ustilago maydis*-fungus codon usage.

SEQ ID NOs: 54 and 55 correspond to primers Mould TPI1 and mould TPI3, respectively, used to isolate genomic fragment of the *Mucor circinelloides* TPI gene.

SEQ ID NOs: 56 and 57 correspond to primers MC_TPI2 and MC_TPI1, respectively, used to isolate genomic fragment of the *Mucor circinelloides* TPI promoter region in chromosome walk experiments.

SEQ ID NOs: 58 and 59 correspond to primers MC_TPI7 and MC_TPI8, respectively, used to clone promoter of the *Mucor circinelloides* TPI gene.

SEQ ID NOs: 60 and 61 correspond to primers MC_TPI4 and MC_TPI3, respectively, used to isolate genomic fragment of the *Mucor circinelloides* TPI terminator region in chromosome walk experiments.

SEQ ID NOs: 62 and 63 correspond to primers MC_TPI5 and MC_TPI6, respectively, used to clone terminator of the *Mucor circinelloides* TPI gene.

SEQ ID NOs: 64 and 65 correspond to primers Mould TEF1 and Mould TEF4, respectively, used to isolate genomic fragment of the *Mucor circinelloides* TEF gene.

SEQ ID NOs: 66, 67, 68 and 69 correspond to primers MC_TEF2, MC_TEF1, MC_TEF6 and MC_TEF5, respectively, used to isolate genomic fragments of the *Mucor circinelloides* TEF promoter region in chromosome walk experiments.

SEQ ID NOs: 70 and 71 correspond to primers MC_TEF9 and MC_TEF10, respectively, used to clone promoter of the *Mucor circinelloides* TEF gene.

SEQ ID NOs: 72, 73, 74 and 75 correspond to primers MC_TEF4, MC_TEF3, MC_TEF8 and MC_TEF7, respectively, used to isolate genomic fragments of the *Mucor circinelloides* TEF terminator region in chromosome walk experiments.

SEQ ID NOs: 76 and 77 correspond to primers MC_TEF11 and MC_TEF12, respectively, used to clone terminator of the *Mucor circinelloides* TEF gene.

SEQ ID NOs: 78 and 79 correspond to primers Mould PGK4 and Mould PGK2, respectively, used to isolate genomic fragment of the *Mucor circinelloides* PGK gene.

SEQ ID NOs: 80, 81, 82 and 83 correspond to primers MC_PGK2, MC_PGK1, MC_PGK4 and MC_PGK3, respectively, used to isolate genomic fragments of the *Mucor circinelloides* PGK promoter region in chromosome walk experiments.

SEQ ID NOs: 84 and 85 correspond to primers MC_PGK5 and MC_PGK6, respectively, used to clone promoter of the *Mucor circinelloides* PGK gene.

SEQ ID NOs: 86, 87, 88 and 89 correspond to primers MC_GPD2, MC_GPD1, MC_GPD10 and MC_GPD9, respectively, used to isolate genomic fragment of the *Mucor circinelloides* GPD promoter region in chromosome walk experiments.

SEQ ID NOs: 90 and 91 correspond to primers MC_GPD11 and MC_GPD12, respectively, used to clone promoter of the *Mucor circinelloides* GPD gene.

SEQ ID NO: 92 corresponds to *S. cerevisiae* ACS2 protein encoding DNA codon optimized according to *Rhizopus oryzae*-fungus codon usage.

SEQ ID NO: 93 corresponds to *Rhizopus oryzae* PDAT protein encoding DNA codon optimised according to *Rhizopus oryzae*-fungus codon usage.

SEQ ID NO: 94 corresponds to *S. cerevisiae* PDC1 protein encoding DNA, with GenBank accession number X77316 (version number X77316.1).

SEQ ID NO: 95 corresponds to the amino acid sequence of the *S. cerevisiae* PDC1 gene, with GenBank accession number CAA54522 (version number CAA54522.1.

SEQ ID NO: 96 corresponds to *S. cerevisiae* PDC1 protein encoding DNA codon optimized according to *Ustilago maydis*-fungus codon usage.

SEQ ID NO: 97 corresponds to *S. cerevisiae* PDC1 protein encoding DNA codon optimized according to *Rhizopus oryzae*-fungus codon usage.

REFERENCES

Altschul, S. F., Madden, T. L., Schäffer, A. A., Zhang, J., Zhang, Z., Miller, W. and Lipman, D. J. 1997. Nucleic Acids Res. 25:3389-3402.

Boulton, C. A. and Ratledge, C. 1981. J. Gen. Microbiol. 127:169-176.

Folch J., Lees M. and Stqanley, G. H. S. J. Biol. Chem. 226:497-509 (1957)

van den Berg, M. A., de Jong-Gubbels, P., Steensma, H. Y., van Dijken, J. P. and Pronk, J. T. 1996. J. Biol. Chem. 271:28953-28959.

Connerton, I. F., Fincham, J. R. S., Sandeman, R. A. and Hynes, M. J. 1990. Mol. Microbiol. 4:451-460.

Dahlqvist, A., Ståhl, U., Lenman, M., Banas, A., Lee, M., Sandager, L., Ronne, H. and Stymne, S. 2000. PNAS 97:6487-6492

Flikweert, M. T., Van der Zanden, L., Janssen, W. M. TH. M., Steensma, H. Y., Van Dijken, J. P. and Pronk, J. T. 1996. Yeast 12:247-257.

Flipphi, M., Mathieu, M., Cirpus, I., Panozzo, C. and Felenbok, B. 2001. J. Biol. Chem. 276:6950-6958.

Hiesinger, M., Wagner, C. and Schuller, H.-J. 1997. FEBS Lett. 415:16-20.

Hynes, M. J. and Murray, S. L. 2010. Euk. Cell 9:1039-1048.

Mach, R. L., Schindler, M. and Kubicek, C. P. 1994. Curr Genet. 25, 567-570

Meesters, P. A. E. P., Springer, J. and Eggink, G. 1997. Appl. Microbiol. Biotechnol. 47:663-667.

Mueller, P. R. and Wold, B. 1989, "In vivo footprinting of a muscle specific enhancer by ligation mediated PCR." Science 246:780-786.

Nakazawa, N., Hashimoto, H., Harashima, S, and Oshima, Y. 1993. J. Ferm. Bioeng. 76:60-63.

Postma, E., Verduyn, C., Scheffers, W. A. and van Dijken, J. P. 1989. Appl. Environ. Microbiol. 55:468-477.

Pronk, J. T., Steensma, H. Y. and Van Dijken, J. P. 1996. Yeast 12:1607-1633.

Ratledge, C. and Wynn, J. P. 2002. Adv. Appl. Microbiol. 51:1-51. Saint-Prix, F., Bonquist, L. and Dequin, S. 2004. Microbiol. 150:2209-2220.

Sambrook, J. and Russell, D. W. 2001. Molecular cloning, a laboratory manual. Cold Spring Harbor Laboratory, New York, US.

Shiba, Y, Paradise, E M, Kirby J, Ro, D-K and Keasling J D. 2007. Metabolic Engineering 9; 160-168.

Skory, C. D. 2003. Curr. Microbiol. 47:59-64.

Sorger D. and Daum G. (2003) Appl. Microbiol. Biotechnol 61:289-299.

Takahashi, H., McCaffery, J. M., Irizarry, R. A. and Boeke, J. D. 2006. Mol. Cell. 23:207-217.

Tehlivets, O., Scheuringer K. and Kohlwein S. D. (1997) Biocim Biophys Acta 1771:255-270.

Wolff, A. M., Appel, K. F., Petersen, J. B., Poulsen, U. and Arnau, J. 2002 FEMS Yeast Res. 2:203-213

The invention claimed is:

1. A genetically modified oleaginous fungal cell comprising:
    a) a nucleic acid with enhanced expression encoding a pyruvate decarboxylase (PDC), and
    b) at least one nucleic acid with enhanced expression encoding an enzyme selected from the group consisting of acetaldehyde dehydrogenase (ALD), acetyl-CoA synthetase (ACS) and diacylglycerol acyltransferase (DAT), wherein said genetically modified oleaginous fungal cell has enhanced lipid production in an aerobic process compared to a genetically unmodified oleaginous fungal cell.

2. The genetically modified oleaginous fungal cell of claim 1, wherein the encoded PDC is a PDC of a Crabtree-positive organism.

3. The genetically modified oleaginous fungal cell of claim 2, wherein the encoded PDC is a PDC of *Saccharomyces cerevisiae*, preferably PDC 1 of *S. cerevisiae*.

4. The genetically modified oleaginous fungal cell of claim 1, wherein the nucleic acid encoding ACS is a gene that is not under glucose repression or its gene product is not subject to post-translational regulation.

5. The genetically modified oleaginous fungal cell of claim 4, wherein the encoded ACS is a fungal ACS, preferably *Saccharomyces cerevisiae* ACS2.

6. The genetically modified oleaginous fungal cell of claim 1, which is a yeast cell selected from the genera *Cryptococcus, Candida, Galactomyces, Hansenula, Lipomyces, Rhodosporidium, Rhodotorula, Trichosporon* and *Yarrowia*, preferably from the group consisting of *Candida* sp., *Cryptococcus curvatus, Cryptococcus albidus, Galactomyces geotrichum, Hansenula ciferri, Lipomyces lipofer, Lipomyces* ssp., *Lipomyces starkeyi, Lipomyces tetrasporus, Rhodosporidium toruloides, Rhodotorula glutinis, Trichosporon pullulans* and *Yarrowia lipolytica*, or a filamentous fungal cell selected from the genera *Aspergillus, Cunninghamella, Fusarium, Glomus, Humicola, Mortierella, Mucor, Penicillium, Pythium* and *Rhizopus*, preferably from the group consisting of *Aspergillus nidulans, Aspergillus oryzae, Aspergillus terreus, Aspergillus niger, Cuninghamella japonica, Fusarium oxysporum, Glomus caledonius, Humicola lanuginose, Mortierella isabellina, Mortierella pusilla, Mortierella vinacea, Mucor circinelloides, Mucor plumbeus, Mucor ramanniana, Penicillium lilacinum, Penicillium spinulosum, Pythium ultimum* and *Rhizopus oryzae*.

7. The genetically modified oleaginous fungal cell of claim 6, which is from the genera *Cryptococcus* or *Mucor*, preferably it is a cell of *Cryptococcus curvatus* or *Mucor circinelloides*.

8. A method of preparing an oleaginous fungal cell of claim 1, said method comprising transforming a fungal cell with
   a) a nucleic acid with enhanced expression encoding a pyruvate decarboxylase (PDC) enzyme, and
   b) at least one nucleic acid with enhanced expression encoding an enzyme selected from the group consisting of acetaldehyde dehydrogenase (ALD), acetyl-CoA synthetase (ACS) and diacylglycerol acyltransferase (DAT).

9. Use of a genetically modified fungal cell of claim 1 for producing lipids, precursors of functional fatty acids, functional fatty acids, biofuels, biodiesel, renewable diesel or lubricants.

10. The genetically modified oleaginous fungal cell of claim 3, where in the PDC1 is from *S. cerevisiae* which encodes the amino acid sequence SEQ ID NO: 95, SEQ ID NO: 96, or SEQ ID NO: 97.

11. The genetically modified oleaginous fungal cell of claim 5, where in the ACS2 is from *S. cerevisiae* which encodes the amino acid sequence SEQ ID NO: 50, SEQ ID NO: 51, or SEQ ID NO: 92.

12. The genetically modified oleaginous fungal cell of claim 1, wherein the at least one nucleic acid with enhanced expression encoding an enzyme is selected from the group consisting of acetyl-CoA synthetase (ACS) and diacylglycerol acyltransferase (DAT).

13. The genetically modified oleaginous fungal cell of claim 1, wherein said genetically modified oleaginous fungal cell has a 33% to 83% higher triacylglycerol yield on biomass compared to the genetically unmodified oleaginous fungal cell.

* * * * *

SEQUENCE LISTING

```
<160> NUMBER OF SEQ ID NOS: 97

<210> SEQ ID NO 1
<211> LENGTH: 24
<212> TYPE: DNA
<213> ORGANISM: Artificial Sequence
<220> FEATURE:
<223> OTHER INFORMATION: primer
```

<400> SEQUENCE: 1
tacaagtgyg gtggtatyga caag                                              24

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
tcwacggayt tgacttcagt ggt                                               23

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
gcggtgaccc gggagatctg aattc                                             25

<210> SEQ ID NO 4
<211> LENGTH: 12
<212> TYPE: DNA
<213> ORGANISM: Artificial Sequence
<220> FEATURE:
<223> OTHER INFORMATION: primer

<400> SEQUENCE: 4
gaattcagat ct                                                           12

<210> SEQ ID NO 5
<211> LENGTH: 17
<212> TYPE: DNA
<213> ORGANISM: Artificial Sequence
<220> FEATURE:
<223> OTHER INFORMATION: primer

<400> SEQUENCE: 5
cacgctcacg ctcggcc                                                      17

<210> SEQ ID NO 6
<211> LENGTH: 15
<212> TYPE: DNA
<213> ORGANISM: Artificial Sequence
<220> FEATURE:
<223> OTHER INFORMATION: primer

<400> SEQUENCE: 6
ccgaggtcgg cggcc                                                        15

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
ggcaggcgca aagctggac                                                    19

<210> SEQ ID NO 8
<211> LENGTH: 26
<212> TYPE: DNA
<213> ORGANISM: Artificial Sequence
<220> FEATURE:
<223> OTHER INFORMATION: primer

<400> SEQUENCE: 8
gcagtcactg tcattgtcgc actacc                                        26

<210> SEQ ID NO 9
<211> LENGTH: 32
<212> TYPE: DNA
<213> ORGANISM: Artificial Sequence
<220> FEATURE:
<223> OTHER INFORMATION: primer

<400> SEQUENCE: 9
tccccgcggg gatccatcac gcctgcccgt cc                                 32

<210> SEQ ID NO 10
<211> LENGTH: 47
<212> TYPE: DNA
<213> ORGANISM: Artificial Sequence
<220> FEATURE:
<223> OTHER INFORMATION: primer

<400> SEQUENCE: 10
gctctagagc ctgcaggttt ttataggttc tgcgaatggt tagtacg                 47

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
cctccaggac gtctacaaga tcggc                                         25

<210> SEQ ID NO 12
<211> LENGTH: 16
<212> TYPE: DNA
<213> ORGANISM: Artificial Sequence
<220> FEATURE:
<223> OTHER INFORMATION: primer

<400> SEQUENCE: 12
cccgtcggcc gtgtcg                                                   16

<210> SEQ ID NO 13
<211> LENGTH: 38
<212> TYPE: DNA
<213> ORGANISM: Artificial Sequence
<220> FEATURE:
<223> OTHER INFORMATION: primer

<400> SEQUENCE: 13
tcccccgggg cctgcaggtt gtagagccct cggttctg                           38

<210> SEQ ID NO 14
<211> LENGTH: 31
<212> TYPE: DNA
<213> ORGANISM: Artificial Sequence
<220> FEATURE:
<223> OTHER INFORMATION: primer

```
<400> SEQUENCE: 14
ggaattccgg aggcttgtca tcatacgaga c                                 31

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
ggtaactkka agatgaacgg ctc                                          23

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
gckccrccga craggaawcc rtc                                          23

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gggaagttgg cgctgtggac                                              20

<210> SEQ ID NO 18
<211> LENGTH: 17
<212> TYPE: DNA
<213> ORGANISM: Artificial Sequence
<220> FEATURE:
<223> OTHER INFORMATION: primer

<400> SEQUENCE: 18
cgctgagctt ggcgtcg                                                 17

<210> SEQ ID NO 19
<211> LENGTH: 29
<212> TYPE: DNA
<213> ORGANISM: Artificial Sequence
<220> FEATURE:
<223> OTHER INFORMATION: primer

<400> SEQUENCE: 19
cgggatcccg gaattcctga ccacccgcg                                    29

<210> SEQ ID NO 20
<211> LENGTH: 39
<212> TYPE: DNA
<213> ORGANISM: Artificial Sequence
<220> FEATURE:
<223> OTHER INFORMATION: primer

<400> SEQUENCE: 20
tgtgtgcctg caggcttgga tatgctgttt taggtttgg                         39
```

```
<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
aagcgcgtct cgcagaagg                                                19

<210> SEQ ID NO 22
<211> LENGTH: 17
<212> TYPE: DNA
<213> ORGANISM: Artificial Sequence
<220> FEATURE:
<223> OTHER INFORMATION: primer

<400> SEQUENCE: 22
acggcggctc cgtcaac                                                  17

<210> SEQ ID NO 23
<211> LENGTH: 35
<212> TYPE: DNA
<213> ORGANISM: Artificial Sequence
<220> FEATURE:
<223> OTHER INFORMATION: primer

<400> SEQUENCE: 23
gctctagagc ctgcagggat gaggcgtggc atagg                              35

<210> SEQ ID NO 24
<211> LENGTH: 26
<212> TYPE: DNA
<213> ORGANISM: Artificial Sequence
<220> FEATURE:
<223> OTHER INFORMATION: primer

<400> SEQUENCE: 24
cgggatcccg cagctgacga caggct                                        26

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
cccgtcacct cycagaagga gattg                                         25

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
cggtctcacc ggatcggtg                                                19

<210> SEQ ID NO 27
<211> LENGTH: 16
<212> TYPE: DNA
<213> ORGANISM: Artificial Sequence
<220> FEATURE:
<223> OTHER INFORMATION: primer
```

<400> SEQUENCE: 27
ttggcagcgg cctcgg                                                          16

<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
ccaaggatgg cgttggcg                                                        18

<210> SEQ ID NO 29
<211> LENGTH: 19
<212> TYPE: DNA
<213> ORGANISM: Artificial Sequence
<220> FEATURE:
<223> OTHER INFORMATION: primer

<400> SEQUENCE: 29
cgtgctcctg cccaggagg                                                       19

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
cgatgctctc ggcagttgcg                                                      20

<210> SEQ ID NO 31
<211> LENGTH: 29
<212> TYPE: DNA
<213> ORGANISM: Artificial Sequence
<220> FEATURE:
<223> OTHER INFORMATION: primer

<400> SEQUENCE: 31
cggaattctg tctgtacgag tctgtacac                                            29

<210> SEQ ID NO 32
<211> LENGTH: 38
<212> TYPE: DNA
<213> ORGANISM: Artificial Sequence
<220> FEATURE:
<223> OTHER INFORMATION: primer

<400> SEQUENCE: 32
ggaattcctg caggtttgag gtgaggttgt tgttttgg                                  38

<210> SEQ ID NO 33
<211> LENGTH: 17
<212> TYPE: DNA
<213> ORGANISM: Artificial Sequence
<220> FEATURE:
<223> OTHER INFORMATION: primer

<400> SEQUENCE: 33
ggcgtgcaac gccctcc                                                         17

<210> SEQ ID NO 34
<211> LENGTH: 21

<212> TYPE: DNA
<213> ORGANISM: Artificial Sequence
<220> FEATURE:
<223> OTHER INFORMATION: primer

<400> SEQUENCE: 34
ccatccaggc gtgggtactg a                                          21

<210> SEQ ID NO 35
<211> LENGTH: 32
<212> TYPE: DNA
<213> ORGANISM: Artificial Sequence
<220> FEATURE:
<223> OTHER INFORMATION: primer

<400> SEQUENCE: 35
cccaagcttc ctgcagggtg cgcgtagtgc gc                              32

<210> SEQ ID NO 36
<211> LENGTH: 29
<212> TYPE: DNA
<213> ORGANISM: Artificial Sequence
<220> FEATURE:
<223> OTHER INFORMATION: primer

<400> SEQUENCE: 36
cccaagcttg ggacgccgag gagcatctc                                  29

<210> SEQ ID NO 37
<211> LENGTH: 21
<212> TYPE: DNA
<213> ORGANISM: Artificial Sequence
<220> FEATURE:
<223> OTHER INFORMATION: primer

<400> SEQUENCE: 37
cgtcggtctt tgacgccaag g                                          21

<210> SEQ ID NO 38
<211> LENGTH: 23
<212> TYPE: DNA
<213> ORGANISM: Artificial Sequence
<220> FEATURE:
<223> OTHER INFORMATION: primer

<400> SEQUENCE: 38
cgtggtacga caacgagtac ggc                                        23

<210> SEQ ID NO 39
<211> LENGTH: 43
<212> TYPE: DNA
<213> ORGANISM: Artificial Sequence
<220> FEATURE:
<223> OTHER INFORMATION: primer

<400> SEQUENCE: 39
gctctagagc ctgcaggatc ccttcgagga tgtagttagg ttg                  43

<210> SEQ ID NO 40
<211> LENGTH: 31
<212> TYPE: DNA
<213> ORGANISM: Artificial Sequence
<220> FEATURE:
<223> OTHER INFORMATION: primer

<400> SEQUENCE: 40
cgggatcccg tggaggtgtc tgtgatgacg a                                    31

<210> SEQ ID NO 41
<211> LENGTH: 38
<212> TYPE: DNA
<213> ORGANISM: Artificial Sequence
<220> FEATURE:
<223> OTHER INFORMATION: primer

<400> SEQUENCE: 41
ggactagtcc tgcaggatga aaaagcctga actcaccg                             38

<210> SEQ ID NO 42
<211> LENGTH: 37
<212> TYPE: DNA
<213> ORGANISM: Artificial Sequence
<220> FEATURE:
<223> OTHER INFORMATION: primer

<400> SEQUENCE: 42
ggactagtcc tgcaggctat tcctttgccc tcggacg                              37

<210> SEQ ID NO 43
<211> LENGTH: 35
<212> TYPE: DNA
<213> ORGANISM: Artificial Sequence
<220> FEATURE:
<223> OTHER INFORMATION: primer

<400> SEQUENCE: 43
ggactagtcc tgcaggatga gccatattca acggg                                35

<210> SEQ ID NO 44
<211> LENGTH: 39
<212> TYPE: DNA
<213> ORGANISM: Artificial Sequence
<220> FEATURE:
<223> OTHER INFORMATION: primer

<400> SEQUENCE: 44
ggactagtcc tgcaggttag aaaaactcat cgagcatca                            39

<210> SEQ ID NO 45
<211> LENGTH: 38
<212> TYPE: DNA
<213> ORGANISM: Artificial Sequence
<220> FEATURE:
<223> OTHER INFORMATION: primer

<400> SEQUENCE: 45
acacaccctg caggatgagt gtgtctaccg ccaagagg                             38

<210> SEQ ID NO 46
<211> LENGTH: 34
<212> TYPE: DNA
<213> ORGANISM: Artificial Sequence
<220> FEATURE:
<223> OTHER INFORMATION: primer

<400> SEQUENCE: 46
gtgtgtcctg caggttaatt tgcggccggt accg                                 34

<210> SEQ ID NO 47
<211> LENGTH: 500
<212> TYPE: PRT
<213> ORGANISM: Saccharomyces cerevisiae

<400> SEQUENCE: 47

| | | | | | | | | | | | | | | |
|---|---|---|---|---|---|---|---|---|---|---|---|---|---|---|
|Met|Thr|Lys|Leu|His|Phe|Asp|Thr|Ala|Glu|Pro|Val|Lys|Ile|Thr|Leu|
|1| | | |5| | | | |10| | | | |15| |

Pro Asn Gly Leu Thr Tyr Glu Gln Pro Thr Gly Leu Phe Ile Asn Asn
                20                  25                  30

Lys Phe Met Lys Ala Gln Asp Gly Lys Thr Tyr Pro Val Glu Asp Pro
            35                  40                  45

Ser Thr Glu Asn Thr Val Cys Glu Val Ser Ser Ala Thr Thr Glu Asp
    50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys

```
                    405                 410                 415
Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500

<210> SEQ ID NO 48
<211> LENGTH: 1506
<212> TYPE: DNA
<213> ORGANISM: Artificial Sequence
<220> FEATURE:
<223> OTHER INFORMATION: S. cerevisiae codon optimized to Ustilago
      maydis

<400> SEQUENCE: 48
atgaccaagc tccacttcga caccgccgag cccgtcaaga tcaccctccc caacggcctc      60
acctacgagc agcccaccgg cctcttcatc aacaacaagt tcatgaaggc ccaggacggc     120
aagacctacc ccgtcgagga cccctcgacc gagaacaccg tctgcgaggt cagctcggcc     180
accaccgagg acgtggagta cgccatcgag tgcgccgacc gcgccttcca cgacaccgag     240
tgggccaccc aggaccctcg cgagcgcggt cgcctcctct ccaaactcgc cgacgaactc     300
gagtcgcaga tcgacctcgt cagctcgatc gaggccctca caacggcaa gaccctcgcc      360 ctcgctcgcg gcgacgtgac gatcgccatc aactgcctcc gcgacgccgc tgcctacgcc     420
gacaaggtca acggccgcac catcaacacc ggcgacggct acatgaactt caccaccctc     480
gagcccatcg gcgtctgcgg ccagatcatc ccctggaact cccccatcat gatgctcgcc     540
tggaagatcg ccccctgccct cgccatgggc aacgtctgca tcctcaagcc tgccgccgtc     600
acccccctca cgccctcta cttcgcctcg ctctgcaaga aggtcggcat ccctgccggc      660
gtcgtcaaca tcgtccctgg ccctggccgc accgtcggcg ctgccctcac caacgaccc      720 cgcatccgca agctcgcctt caccggctcg accgaggtcg gcaagtcggt cgccgtcgac     780
tcgtcggagt cgaacctcaa gaagatcacg ctcgaactcg cggcaagtc ggcccacctc      840 gtgtttgacg acgccaacat caagaaaacc ctccctaacc tcgtcaacgg catcttcaag     900
aacgccggcc agatctgctc gtcgggctcg cgcatctacg tccaggaagg catctacgac     960
gaactcctcg ccgccttcaa ggcctacctc gaaaccgaga tcaaggtcgg caacccttc     1020 gacaaggcca acttccaggg cgccatcacc aacgccagc agttcgacac catcatgaac     1080
tacatcgaca tcggcaagaa ggaaggcgct aagatcctca cgggcggtga aaaggtcggc    1140
gacaagggct acttcatccg ccccaccgtc ttttacgacg tgaacgagga catgcgcatc    1200
gtcaaggaag agatcttcgg ccccgtcgtc accgtcgcca agttcaagac cctcgaagag    1260
ggcgtcgaga tggctaactc gagcgaattt ggcctcggct cgggcatcga aaccgagtcg    1320
ctctcgaccg gcctcaaggt cgccaagatg ctcaaggccg gcaccgtctg gatcaacacc    1380
tacaacgact cgactcgcg cgtccccttc ggcggcgtca gcagtcggg ctacggccgc     1440
```

| gagatgggcg aggaagtcta ccacgcctac accgaggtca aggccgtccg catcaagctc | 1500 |
| tgatga | 1506 |

<210> SEQ ID NO 49
<211> LENGTH: 1506
<212> TYPE: DNA
<213> ORGANISM: Artificial Sequence
<220> FEATURE:
<223> OTHER INFORMATION: S. cerevisiae codon optimized to Rhizopus oryzae

<400> SEQUENCE: 49

| atgacaaaac ttcattttga tacagctgaa ccagttaaaa tcacacttcc aaatggtctt | 60 |
| acttatgaac aaccaacagg tcttttttatc aacaacaaat ttatgaaagc tcaggatggt | 120 |
| aaaacatatc cagttgaaga tccatcaaca gaaaatacag tttgtgaagt ttcatcagct | 180 |
| acaacagagg atgttgaata tgctattgaa tgtgctgatc gagcttttca tgatacagaa | 240 |
| tgggctacac aagatccacg agaacgaggt cgacttcttt caaaacttgc tgatgaactt | 300 |
| gaatcacaaa ttgatcttgt ttcatcaatc gaagctcttg ataatggtaa acacttgct | 360 |
| cttgctcgag gtgatgttac aattgctatc aattgtttgc gagatgctgc tgcttatgct | 420 |
| gataaagtta atggtcgaac aattaataca ggtgatggtt atatgaattt tacaacgctt | 480 |
| gaaccaattg gtgtttgtgg tcaaattatt ccatggaact ttccaattat gatgcttgct | 540 |
| tggaaaattg ctccagctct tgctatgggt aatgtttgta ttcttaaacc agctgctgtt | 600 |
| acaccactta atgcactttta ttttgcttca ctttgtaaaa aagttggtat tccagctggt | 660 |
| gttgttaata ttgttccagg tccaggtcga acagttggtg ctgctcttac aaatgatcca | 720 |
| cgtattcgaa aacttgcttt tacaggttca acagaagttg gtaaatcagt tgctgttgat | 780 |
| tcatcagagt caaacttgaa aaaaatcact cttgaacttg gtggtaaatc agctcatctt | 840 |
| gtctttgatg atgctaacat caaaaaaaca cttccaaacc ttgtcaatgg tatctttaaa | 900 |
| aacgctggtc aaatttgttc atcaggttca cgaatttatg tccaagaggg tatctatgat | 960 |
| gaacttcttg ctgcttttaa agcatatctt gagacagaaa ttaaagtcgg taacccattt | 1020 |
| gataaagcta atttttcaagg tgctatcaca atcgacaac aatttgatac gatcatgaac | 1080 |
| tatattgata tcggtaaaaa agaaggtgct aaaattctta caggtggtga aaaagttggt | 1140 |
| gataaaggtt attttatccg accaacagtc ttttatgatg tcaatgaaga tatgcgaatt | 1200 |
| gtcaaagaag aaattttttgg tccagttgtt acagttgcta aattcaagac acttgaagag | 1260 |
| ggtgttgaaa tggctaattc atcagaattt ggtcttggtt caggtattga aacagaatca | 1320 |
| ctttcaacag gtcttaaagt cgctaaaatg cttaaagctg gtacagtttg gattaacacg | 1380 |
| tataacgatt tgattcacg agttccattt ggtggtgtta acaatcagg ttatggtcga | 1440 |
| gaaatgggtg aagaagttta tcacgcttat acagaagtta agctgtccg aatcaaactt | 1500 |
| taataa | 1506 |

<210> SEQ ID NO 50
<211> LENGTH: 683
<212> TYPE: PRT
<213> ORGANISM: Saccharomyces cerevisiae

<400> SEQUENCE: 50

Met Thr Ile Lys Glu His Lys Val Val Tyr Glu Ala His Asn Val Lys
1               5                   10                  15

Ala Leu Lys Ala Pro Gln His Phe Tyr Asn Ser Gln Pro Gly Lys Gly

```
                20                  25                  30
Tyr Val Thr Asp Met Gln His Tyr Gln Glu Met Tyr Gln Gln Ser Ile
                    35                  40                  45
Asn Glu Pro Glu Lys Phe Phe Asp Lys Met Ala Lys Glu Tyr Leu His
 50                  55                  60
Trp Asp Ala Pro Tyr Thr Lys Val Gln Ser Gly Ser Leu Asn Asn Gly
 65                  70                  75                  80
Asp Val Ala Trp Phe Leu Asn Gly Lys Leu Asn Ala Ser Tyr Asn Cys
                 85                  90                  95
Val Asp Arg His Ala Phe Ala Asn Pro Asp Lys Pro Ala Leu Ile Tyr
                100                 105                 110
Glu Ala Asp Asp Glu Ser Asp Asn Lys Ile Ile Thr Phe Gly Glu Leu
            115                 120                 125
Leu Arg Lys Val Ser Gln Ile Ala Gly Val Leu Lys Ser Trp Gly Val
            130                 135                 140
Lys Lys Gly Asp Thr Val Ala Ile Tyr Leu Pro Met Ile Pro Glu Ala
145                 150                 155                 160
Val Ile Ala Met Leu Ala Val Ala Arg Ile Gly Ala Ile His Ser Val
                165                 170                 175
Val Phe Ala Gly Phe Ser Ala Gly Ser Leu Lys Asp Arg Val Val Asp
            180                 185                 190
Ala Asn Ser Lys Val Val Ile Thr Cys Asp Glu Gly Lys Arg Gly Gly
            195                 200                 205
Lys Thr Ile Asn Thr Lys Lys Ile Val Asp Glu Gly Leu Asn Gly Val
        210                 215                 220
Asp Leu Val Ser Arg Ile Leu Val Phe Gln Arg Thr Gly Thr Glu Gly
225                 230                 235                 240
Ile Pro Met Lys Ala Gly Arg Asp Tyr Trp Trp His Glu Glu Ala Ala
                245                 250                 255
Lys Gln Arg Thr Tyr Leu Pro Pro Val Ser Cys Asp Ala Glu Asp Pro
            260                 265                 270
Leu Phe Leu Leu Tyr Thr Ser Gly Ser Thr Gly Ser Pro Lys Gly Val
        275                 280                 285
Val His Thr Thr Gly Gly Tyr Leu Leu Gly Ala Ala Leu Thr Thr Arg
        290                 295                 300
Tyr Val Phe Asp Ile His Pro Glu Asp Val Leu Phe Thr Ala Gly Asp
305                 310                 315                 320
Val Gly Trp Ile Thr Gly His Thr Tyr Ala Leu Tyr Gly Pro Leu Thr
                325                 330                 335
Leu Gly Thr Ala Ser Ile Ile Phe Glu Ser Thr Pro Ala Tyr Pro Asp
            340                 345                 350
Tyr Gly Arg Tyr Trp Arg Ile Gln Arg His Lys Ala Thr His Phe
        355                 360                 365
Tyr Val Ala Pro Thr Ala Leu Arg Leu Ile Lys Arg Val Gly Glu Ala
        370                 375                 380
Glu Ile Ala Lys Tyr Asp Thr Ser Ser Leu Arg Val Leu Gly Ser Val
385                 390                 395                 400
Gly Glu Pro Ile Ser Pro Asp Leu Trp Glu Trp Tyr His Glu Lys Val
                405                 410                 415
Gly Asn Lys Asn Cys Val Ile Cys Asp Thr Met Trp Gln Thr Glu Ser
            420                 425                 430
Gly Ser His Leu Ile Ala Pro Leu Ala Gly Ala Val Pro Thr Lys Pro
        435                 440                 445
```

```
Gly Ser Ala Thr Val Pro Phe Phe Gly Ile Asn Ala Cys Ile Ile Asp
    450                 455                 460

Pro Val Thr Gly Val Glu Leu Glu Gly Asn Asp Val Glu Gly Val Leu
465                 470                 475                 480

Ala Val Lys Ser Pro Trp Pro Ser Met Ala Arg Ser Val Trp Asn His
            485                 490                 495

His Asp Arg Tyr Met Asp Thr Tyr Leu Lys Pro Tyr Pro Gly His Tyr
        500                 505                 510

Phe Thr Gly Asp Gly Ala Gly Arg Asp His Asp Gly Tyr Tyr Trp Ile
    515                 520                 525

Arg Gly Arg Val Asp Asp Val Val Asn Val Ser Gly His Arg Leu Ser
530                 535                 540

Thr Ser Glu Ile Glu Ala Ser Ile Ser Asn His Glu Asn Val Ser Glu
545                 550                 555                 560

Ala Ala Val Val Gly Ile Pro Asp Glu Leu Thr Gly Gln Thr Val Val
                565                 570                 575

Ala Tyr Val Ser Leu Lys Asp Gly Tyr Leu Gln Asn Asn Ala Thr Glu
            580                 585                 590

Gly Asp Ala Glu His Ile Thr Pro Asp Asn Leu Arg Arg Glu Leu Ile
        595                 600                 605

Leu Gln Val Arg Gly Glu Ile Gly Pro Phe Ala Ser Pro Lys Thr Ile
    610                 615                 620

Ile Leu Val Arg Asp Leu Pro Arg Thr Arg Ser Gly Lys Ile Met Arg
625                 630                 635                 640

Arg Val Leu Arg Lys Val Ala Ser Asn Glu Ala Glu Gln Leu Gly Asp
                645                 650                 655

Leu Thr Thr Leu Ala Asn Pro Glu Val Val Pro Ala Ile Ile Ser Ala
            660                 665                 670

Val Glu Asn Gln Phe Phe Ser Gln Lys Lys Lys
        675                 680

<210> SEQ ID NO 51
<211> LENGTH: 2052
<212> TYPE: DNA
<213> ORGANISM: Artificial Sequence
<220> FEATURE:
<223> OTHER INFORMATION: S.cerevisiae codon optimized to Ustilago maydis

<400> SEQUENCE: 51
atgaccatca aggagcacaa ggtcgtctac gaggcccaca cgtcaaggc cctcaaggct      60 ccccagcact tctacaactc gcagcccggc aagggctacg tcaccgacat gcagcactac    120
caggagatgt accagcagtc gatcaacgag cccgagaagt tcttcgacaa gatggccaag    180
gagtacctcc actgggacgc ccctacacc aaggtccagt cgggctcgct caacaacggc    240
gatgtcgcct ggttcctcaa cggcaagctc aacgcctcgt acaactgcgt cgaccgccac    300
gccttcgcca ccccgacaa gcccgccctc atctacgagg ccgacgacga gtcggacaac    360
aagatcatca ccttcggcga actcctccgc aaggtctcgc agatcgccgg cgtcctcaag    420
tcgtggggcg tcaagaaggg cgacaccgtc gccatctacc tccccatgat ccccgaggcc    480
gtcatcgcca tgctcgccgt cgcccgcatc ggcgccatcc actcggtcgt ctttgccggc    540
ttctcggccg gctcgctcaa ggaccgcgtc gtcgatgcca actcgaaggt cgtcatcacc    600
tgcgacgagg gcaagcgcgg tggcaagacc atcaacacca agaagatcgt cgacgaaggc    660
ctcaacggcg tcgacctcgt ctcgcgcatc ctcgtctttc agcgcaccgg caccgagggc    720
```

```
atcccccatga aggctggccg cgactactgg tggcacgagg aggccgccaa gcagcgcacc      780
tacctccccc ctgtctcgtg cgacgccgag accccctct tcctcctcta cacctcgggc       840
tcgaccggca gccctaaggg cgtcgtccat acgaccggcg gctacctcct cggcgctgcc      900
ctcaccaccc gctacgtctt tgacatccac cccgaggacg tgctcttcac cgctggcgac      960
gtgggctgga tcaccggcca cacctacgcc ctctacggcc ccctcaccct cggcaccgcc     1020
tcgatcatct tcgagtcgac ccccgcctac cccgactacg ccgctactg cgcatcatc       1080 cagcgccaca aggccaccca cttctacgtc gccccaccg ccctccgcct catcaagcgc       1140
gtcggcgagg ccgagatcgc caagtacgac acctcgtcgc tccgcgtcct cggctcggtc     1200
ggcgagccca tctcgcccga cctctgggag tggtatcacg agaaggtcgg caacaagaac     1260
tgcgtcatct gcgacaccat gtggcagacc gagtcgggtt cgcacctcat cgccccctc     1320 gctggcgccg tccctaccaa gcctggctcg gccaccgtcc ctttcttcgg catcaacgcc    1380
tgcatcatcg accccgtcac cggcgtcgaa ctcgagggca cgacgtgga gggcgtcctc     1440 gccgtcaagt cgccctggcc ctcgatggcc cgcagcgtct ggaaccacca cgaccgctac     1500
atggacacct acctcaagcc ctaccccggc cactacttca ccggcgacgg cgctggtcgc    1560
gatcacgatg gctactactg gattcgcggt cgcgtcgacg atgtcgtcaa cgtctcgggc    1620
caccgcctct cgacctcgga gatcgaggcc agcatcagca accacgagaa cgtctcggag    1680
gccgccgtcg tcggcatccc cgacgaactc accggccaga ccgtcgtcgc ctacgtctcg    1740
ctcaaggacg gctacctcca gaacaacgcc accgagggcg acgccgagca catcacccc    1800 gacaacctcc gccgcgaact catcctccag gtccgcggcg agatcggccc cttcgcctcg    1860
cccaagacca tcatcctcgt ccgcgacctc cctcgcaccc gctcgggcaa gatcatgcgc    1920
cgcgtcctcc gcaaggtcgc ctcgaacgag gccgagcagc ttggtgacct caccacccta    1980
gccaaccctg aggtcgtccc cgccatcatc tcggccgtcg agaaccagtt cttctcgcaa    2040
aagaagaagt ga                                                        2052
```

<210> SEQ ID NO 52
<211> LENGTH: 611
<212> TYPE: PRT
<213> ORGANISM: Rhizopus oryzae

<400> SEQUENCE: 52

Met Ser Lys Leu Arg Arg Arg Lys Gln Glu Lys Thr Thr Lys Thr Asn
1               5                   10                  15

Asp Gln Glu Leu Pro Glu Asp Ile Met Ala Asp Ser Ala Ala Asn Val
            20                  25                  30

Phe Lys Glu Lys Arg Pro Phe Trp Gly Arg Lys Arg Phe Asn Phe Ile
        35                  40                  45

Val Gly Leu Ser Val Gly Leu Leu Ala Met Tyr Ala Ala Ser Thr Thr
    50                  55                  60

Pro Val Ala Gln Ser His Ile Asn Ser Leu Gln His Tyr Leu Leu Leu
65                  70                  75                  80

Gln Leu Ala Asp Ile Asp Leu Ala Ser Ile Leu Pro Ala Thr Glu Met
            85                  90                  95

Val Asp Glu Phe Leu Gly Asn Phe Thr Asn Leu Ile Thr Pro Thr Pro
            100                 105                 110

Ala Thr Glu Met Ser Phe Met Pro Ala Leu Glu Tyr Lys Glu Ser Leu
        115                 120                 125

-continued

```
Asp Leu Lys Pro Gln Phe Pro Val Val Met Ile Pro Ala Met Val Arg
    130                 135                 140
Ser Val Leu Leu Asp Lys Glu Ser Trp Thr Glu His Ile Met Leu Asp
145                 150                 155                 160
Pro Glu Thr Gly Leu Asp Pro Pro Gly Tyr Lys Val Arg Ala Val His
                165                 170                 175
Glu Lys Lys Gly Val Glu Ala Ala Asp Tyr Phe Ile Thr Gly Tyr Trp
            180                 185                 190
Val Trp Ala Lys Val Ile Glu Asn Leu Ala Thr Ile Gly Tyr Asp Thr
        195                 200                 205
Asn Asn Met Tyr Phe Ala Ser Tyr Asp Trp Arg Leu Ser Phe Ser Asn
    210                 215                 220
Leu Glu Val Arg Asp Gly Tyr Phe Ser Lys Leu Lys His Thr Ile Glu
225                 230                 235                 240
Leu Ser Lys Lys Gln Ser Gly Gln Lys Ser Val Ile Thr His Ser
                245                 250                 255
Met Gly Gly Thr Met Phe Pro Tyr Phe Leu Lys Trp Val Glu Ser Lys
            260                 265                 270
Gly His Gly Gln Gly Gly Gln Lys Trp Val Asp Glu His Ile Glu Ser
        275                 280                 285
Phe Val Asn Ile Ala Ala Pro Leu Val Gly Val Pro Lys Ala Val Thr
    290                 295                 300
Ser Leu Leu Ser Gly Glu Thr Arg Asp Thr Met Ala Leu Gly Ser Phe
305                 310                 315                 320
Gly Ala Tyr Val Leu Glu Lys Phe Phe Ser Arg Arg Glu Arg Ala Lys
                325                 330                 335
Leu Met Arg Ser Trp Met Gly Ala Ser Met Leu Pro Lys Gly Gly
            340                 345                 350
Glu Ala Ile Trp Gly Arg Gly Gly Asn Ala Pro Asp Asp Glu Glu Asp
        355                 360                 365
Glu Lys Tyr Gln Ser Phe Gly Asn Met Ile Ser Phe Val Pro Arg Pro
    370                 375                 380
Glu Gly Phe Asn Glu Asn Ser Thr Asp Ile Pro Ser Asn Ser Gly Asp
385                 390                 395                 400
Pro Leu Val Arg Asn Tyr Thr Val Gln Gly Ser Ile Gln Leu Leu Thr
                405                 410                 415
Lys Asn Ala Asp Ile Lys Phe Gly Lys Gln Leu Tyr Ala Asn Tyr Ser
            420                 425                 430
Phe Gly Leu Thr Thr Ser Ser Lys Gln Leu Lys Arg Asn Glu Asn Asp
        435                 440                 445
Pro Thr Lys Trp Ser Asn Pro Leu Glu Ser Arg Leu Pro Asn Ala Pro
    450                 455                 460
Asn Met Lys Ile Tyr Cys Phe Tyr Gly Ile Glu Val Pro Thr Glu Arg
465                 470                 475                 480
Ser Tyr Tyr Tyr Ala Ile Leu Asn Glu Asn Met Asp Gln Glu Cys Gly
                485                 490                 495
His Ser Asn Ser Thr Ala Glu Cys Thr Thr Glu Gln Asn Ala Glu Pro
            500                 505                 510
Asn Ser Ser Pro Ala Val Ala Lys Thr Ser Ser Ala Ala Phe Pro Asp
        515                 520                 525
Lys Thr Pro Ser Leu His Ile Asp Ala Ser Ile Asn Asp Pro Val Gln
    530                 535                 540
Arg Ile Glu Thr Gly Ile Arg Phe Ser Asn Gly Asp Gly Thr Val Pro
```

```
                        545                 550                 555                 560
Leu Leu Ser Leu Gly Tyr Met Cys Ala Pro Ser Gly Gly Trp Arg Lys
                565                 570                 575

His Ala Asp Leu Tyr Asn Pro Gly His Ser Pro Val Val Leu Arg Glu
            580                 585                 590

Tyr Lys His Glu Val Ser Thr Ser Lys Leu Asp Val Arg Gly Gly Trp
        595                 600                 605

Ile Ser Tyr
    610

<210> SEQ ID NO 53
<211> LENGTH: 1836
<212> TYPE: DNA
<213> ORGANISM: Artificial Sequence
<220> FEATURE:
<223> OTHER INFORMATION: Rhizopus oryzae codon optimized to Ustilago
      maydis

<400> SEQUENCE: 53
atgtcgaagc tccgccgtcg caagcaggaa aagaccacca agaccaacga ccaggaactc      60
cccgaggaca tcatggctga ctcggccgcc aacgtcttta aggagaagcg cccccttctgg    120 ggccgcaagc gcttcaactt catcgtcggc ctcagcgtcg gcctcctcgc catgtacgcc     180
gccagcacca cccctgtcgc ccagtcgcac atcaactcgc tccagcacta cctcctcctc     240
caactcgccg acatcgacct cgcctcgatc ctccccgcca ccgagatggt cgacgagttc     300
ctcggcaact tcaccaacct catcacccc accctgcta cggagatgtc gttcatgccc      360
gccctcgagt acaaggagtc gctcgacctc aagccccagt tccccgtcgt catgatcccc     420
gctatggtcc gctcggtcct cctcgacaag gaaagctgga ccgagcacat catgctcgac    480
cccgaaacgg gcctcgaccc accccggctac aaggtccgcg ccgtccacga agaaggggc    540 gtcgaggccg ccgactactt catcaccggc tactgggtct gggccaaggt catcgagaac    600
ctcgccacca tcggctacga caccaacaac atgtacttcg cctcgtacga ctggcgcctc    660
tcgttctcga acctcgaagt ccgcgacggc tacttctcga agctcaagca caccatcgaa    720
ctctcgaaga agcagtcggg ccagaagtcg gtcatcatca cccactcgat gggcggcacc    780
atgttccctt actttctcaa gtgggtcgag tcgaagggcc acggccaggg cggtcagaag    840
tgggtcgaca gcacatcga gtcgttcgtc aacatcgctg cccccctcgt cggcgtcccc     900
aaggccgtca cctcgctcct ctcgggcgag acccgcgaca ccatggccct cggctcgttc    960
ggcgcctacg tcctcgagaa gttcttctcg cgtcgagagc gcgccaagct catgcgctcg   1020
tggatgggcg gtgcctcgat gctccccaag ggcggcgagg ctatctgggg tcgcggcggt   1080
aacgcccccg acgacgagga ggacgagaag taccaatcgt tcggtaacat gatctcgttc   1140
gtccctcgcc ccgagggctt caacgagaac tcgaccgaca tccctcgaa ctcgggcgac    1200 cccctcgtcc gcaactacac cgtccagggc tcgatccagc tcctcaccaa gaacgccgac   1260
atcaagttcg gcaagcagct ctacgccaac tactcgttcg gcctcaccac ctcgtcgaag   1320
cagctcaagc gcaacgagaa cgaccccacc aagtggtcga accccctcga gtcgcgcctc   1380
cccaacgccc ccaacatgaa gatctactgc ttctacggca tcgaggtccc caccgaacgc   1440
tcgtactact acgccatcct caacgagaac atggaccagg agtgcggcca ctcgaactcg   1500
accgccgagt gcaccaccga gcagaacgcc gagcccaact cgtcgcctgc tgtcgccaag   1560
acctcgtcgg ccgccttccc cgacaagacc ccttcgctcc acatcgacgc ctcgatcaac   1620
```

```
gaccctgtcc agcgcatcga gaccggcatc cgcttctcga acggcgacgg caccgtcccg    1680
ctcctctcgc tcggctacat gtgcgccccc tcgggcggtt ggcgcaagca cgccgacctc    1740
tacaaccccg gccactcgcc cgtcgtcctc cgcgagtaca agcacgaggt ctcgacctcg    1800
aagctcgatg tccgcggtgg ctggatctcg tactga                              1836
```

<210> SEQ ID NO 54
<211> LENGTH: 22
<212> TYPE: DNA
<213> ORGANISM: Artificial Sequence
<220> FEATURE:
<223> OTHER INFORMATION: primer

<400> SEQUENCE: 54

```
gaggtygtcg tykcycctcc yg                                             22
```

<210> SEQ ID NO 55
<211> LENGTH: 25
<212> TYPE: DNA
<213> ORGANISM: Artificial Sequence
<220> FEATURE:
<223> OTHER INFORMATION: primer

<400> SEQUENCE: 55

```
gcgaccttrc crgtrccgat rgccc                                          25
```

<210> SEQ ID NO 56
<211> LENGTH: 25
<212> TYPE: DNA
<213> ORGANISM: Artificial Sequence
<220> FEATURE:
<223> OTHER INFORMATION: primer

<400> SEQUENCE: 56

```
aacaacccaa tcaacaccca tatcc                                          25
```

<210> SEQ ID NO 57
<211> LENGTH: 24
<212> TYPE: DNA
<213> ORGANISM: Artificial Sequence
<220> FEATURE:
<223> OTHER INFORMATION: primer

<400> SEQUENCE: 57

```
ttttgagcag caaccttgat ttcc                                           24
```

<210> SEQ ID NO 58
<211> LENGTH: 42
<212> TYPE: DNA
<213> ORGANISM: Artificial Sequence
<220> FEATURE:
<223> OTHER INFORMATION: primer

<400> SEQUENCE: 58

```
cgggatcccg gaattccagc ctctctaaac gagagttatc cc                       42
```

<210> SEQ ID NO 59
<211> LENGTH: 50
<212> TYPE: DNA
<213> ORGANISM: Artificial Sequence
<220> FEATURE:
<223> OTHER INFORMATION: primer

<400> SEQUENCE: 59

```
tcccccgggg cctgcagggt tgaatatata aagttttttt ttagaaaaaa               50
```

```
<210> SEQ ID NO 60
<211> LENGTH: 25
<212> TYPE: DNA
<213> ORGANISM: Artificial Sequence
<220> FEATURE:
<223> OTHER INFORMATION: primer

<400> SEQUENCE: 60
ggtgtctccg tcattgcctg tattg                                          25

<210> SEQ ID NO 61
<211> LENGTH: 25
<212> TYPE: DNA
<213> ORGANISM: Artificial Sequence
<220> FEATURE:
<223> OTHER INFORMATION: primer

<400> SEQUENCE: 61
gtcgctcgtc aaatgaaggc tattg                                          25

<210> SEQ ID NO 62
<211> LENGTH: 36
<212> TYPE: DNA
<213> ORGANISM: Artificial Sequence
<220> FEATURE:
<223> OTHER INFORMATION: primer

<400> SEQUENCE: 62
gctctagagc ctgcagggtt gcttcgctcc cctccc                              36

<210> SEQ ID NO 63
<211> LENGTH: 33
<212> TYPE: DNA
<213> ORGANISM: Artificial Sequence
<220> FEATURE:
<223> OTHER INFORMATION: primer

<400> SEQUENCE: 63
cgggatcccg cactgccaga ctaaacgcca gag                                 33

<210> SEQ ID NO 64
<211> LENGTH: 24
<212> TYPE: DNA
<213> ORGANISM: Artificial Sequence
<220> FEATURE:
<223> OTHER INFORMATION: primer

<400> SEQUENCE: 64
cggtaagggt tcyttcaagt acgc                                           24

<210> SEQ ID NO 65
<211> LENGTH: 19
<212> TYPE: DNA
<213> ORGANISM: Artificial Sequence
<220> FEATURE:
<223> OTHER INFORMATION: primer

<400> SEQUENCE: 65
ggaagacgga grggcttgt                                                 19

<210> SEQ ID NO 66
<211> LENGTH: 25
<212> TYPE: DNA
<213> ORGANISM: Artificial Sequence
<220> FEATURE:
```

<223> OTHER INFORMATION: primer

<400> SEQUENCE: 66
ttgtacttgg gggtctcgaa cttcc                                          25

<210> SEQ ID NO 67
<211> LENGTH: 22
<212> TYPE: DNA
<213> ORGANISM: Artificial Sequence
<220> FEATURE:
<223> OTHER INFORMATION: primer

<400> SEQUENCE: 67
gataccacgc tcagcttcag cc                                             22

<210> SEQ ID NO 68
<211> LENGTH: 26
<212> TYPE: DNA
<213> ORGANISM: Artificial Sequence
<220> FEATURE:
<223> OTHER INFORMATION: primer

<400> SEQUENCE: 68
ggatggatgg atggatgcat agtatg                                         26

<210> SEQ ID NO 69
<211> LENGTH: 27
<212> TYPE: DNA
<213> ORGANISM: Artificial Sequence
<220> FEATURE:
<223> OTHER INFORMATION: primer

<400> SEQUENCE: 69
cacaacactt ctccaaatct gagaagc                                        27

<210> SEQ ID NO 70
<211> LENGTH: 33
<212> TYPE: DNA
<213> ORGANISM: Artificial Sequence
<220> FEATURE:
<223> OTHER INFORMATION: primer

<400> SEQUENCE: 70
cccaagcttg ggagcaatgc taaaaaagcc tgg                                 33

<210> SEQ ID NO 71
<211> LENGTH: 53
<212> TYPE: DNA
<213> ORGANISM: Artificial Sequence
<220> FEATURE:
<223> OTHER INFORMATION: primer

<400> SEQUENCE: 71
tgtgtgcctg caggtttgaa taactatagt atagattttt agtacatcga tgg           53

<210> SEQ ID NO 72
<211> LENGTH: 23
<212> TYPE: DNA
<213> ORGANISM: Artificial Sequence
<220> FEATURE:
<223> OTHER INFORMATION: primer

<400> SEQUENCE: 72
gggatggaac aaggagacca agg                                            23

```
<210> SEQ ID NO 73
<211> LENGTH: 23
<212> TYPE: DNA
<213> ORGANISM: Artificial Sequence
<220> FEATURE:
<223> OTHER INFORMATION: primer

<400> SEQUENCE: 73
gactctcctc gaagccatcg atg                                              23

<210> SEQ ID NO 74
<211> LENGTH: 14
<212> TYPE: DNA
<213> ORGANISM: Artificial Sequence
<220> FEATURE:
<223> OTHER INFORMATION: primer

<400> SEQUENCE: 74
ccaaggccgc cgcc                                                        14

<210> SEQ ID NO 75
<211> LENGTH: 25
<212> TYPE: DNA
<213> ORGANISM: Artificial Sequence
<220> FEATURE:
<223> OTHER INFORMATION: primer

<400> SEQUENCE: 75
gcccttgtat aaagtgtgct tttgg                                            25

<210> SEQ ID NO 76
<211> LENGTH: 42
<212> TYPE: DNA
<213> ORGANISM: Artificial Sequence
<220> FEATURE:
<223> OTHER INFORMATION: primer

<400> SEQUENCE: 76
tcccccgggg cctgcaggat tgctacctgc tagttttttc tt                         42

<210> SEQ ID NO 77
<211> LENGTH: 32
<212> TYPE: DNA
<213> ORGANISM: Artificial Sequence
<220> FEATURE:
<223> OTHER INFORMATION: primer

<400> SEQUENCE: 77
ggaattccaa aagtcttttt gggtgtcttt ag                                    32

<210> SEQ ID NO 78
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (14)..(14)
<223> OTHER INFORMATION: n is a, c, g, or t

<400> SEQUENCE: 78
tcaccaacaa cmancgtaty gt                                               22

<210> SEQ ID NO 79
<211> LENGTH: 23
<212> TYPE: DNA
```

<213> ORGANISM: Artificial Sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n is a, c, g, or t

<400> SEQUENCE: 79
tggaaacgma ggttytcnar aag                                           23

<210> SEQ ID NO 80
<211> LENGTH: 19
<212> TYPE: DNA
<213> ORGANISM: Artificial Sequence
<220> FEATURE:
<223> OTHER INFORMATION: primer

<400> SEQUENCE: 80
caacagcctc accgttggg                                                19

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
gcagcacctt gttcaagggc                                               20

<210> SEQ ID NO 82
<211> LENGTH: 29
<212> TYPE: DNA
<213> ORGANISM: Artificial Sequence
<220> FEATURE:
<223> OTHER INFORMATION: primer

<400> SEQUENCE: 82
gacactgttt tgaaatgcct aacccatac                                     29

<210> SEQ ID NO 83
<211> LENGTH: 24
<212> TYPE: DNA
<213> ORGANISM: Artificial Sequence
<220> FEATURE:
<223> OTHER INFORMATION: primer

<400> SEQUENCE: 83
gtacggaaaa cagagtcatg gtgc                                          24

<210> SEQ ID NO 84
<211> LENGTH: 35
<212> TYPE: DNA
<213> ORGANISM: Artificial Sequence
<220> FEATURE:
<223> OTHER INFORMATION: primer

<400> SEQUENCE: 84
tccccgcggg gatcccaagg cactaccact acttc                              35

<210> SEQ ID NO 85
<211> LENGTH: 48
<212> TYPE: DNA
<213> ORGANISM: Artificial Sequence
<220> FEATURE:
<223> OTHER INFORMATION: primer -continued

<400> SEQUENCE: 85
gctctagagc ctgcagggat taattatatg attcaatgat gaagataa    48

<210> SEQ ID NO 86
<211> LENGTH: 21
<212> TYPE: DNA
<213> ORGANISM: Artificial Sequence
<220> FEATURE:
<223> OTHER INFORMATION: primer

<400> SEQUENCE: 86
ctcgacggaa ccatcgaaac g    21

<210> SEQ ID NO 87
<211> LENGTH: 26
<212> TYPE: DNA
<213> ORGANISM: Artificial Sequence
<220> FEATURE:
<223> OTHER INFORMATION: primer

<400> SEQUENCE: 87
gaaggacaat acgaccaata cgaccg    26

<210> SEQ ID NO 88
<211> LENGTH: 32
<212> TYPE: DNA
<213> ORGANISM: Artificial Sequence
<220> FEATURE:
<223> OTHER INFORMATION: primer

<400> SEQUENCE: 88
ggcttctttc cttggtgaat aaagtgagtt ac    32

<210> SEQ ID NO 89
<211> LENGTH: 28
<212> TYPE: DNA
<213> ORGANISM: Artificial Sequence
<220> FEATURE:
<223> OTHER INFORMATION: primer

<400> SEQUENCE: 89
cggaaattat ccgttcaaac tatcgccc    28

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
agccaaaagt tgaattcgac    20

<210> SEQ ID NO 91
<211> LENGTH: 59
<212> TYPE: DNA
<213> ORGANISM: Artificial Sequence
<220> FEATURE:
<223> OTHER INFORMATION: primer

<400> SEQUENCE: 91
cccaagcttc ctgcaggttt tagaatttat gaaatatata tatataaaga tataatatg    59

<210> SEQ ID NO 92

<211> LENGTH: 2052
<212> TYPE: DNA
<213> ORGANISM: Artificial Sequence
<220> FEATURE:
<223> OTHER INFORMATION: S.cerevisiae codon optimized to Rhizopus oryzae

<400> SEQUENCE: 92

```
atgacaatta agaacataa agtcgtttat gaagctcata atgttaaagc tcttaaagca      60
ccacaacatt tctataattc acaaccaggt aaaggttatg tcacagatat gcagcattat     120
caagaaatgt atcaacaatc aatcaacgaa ccagagaaat ttttcgataa gatggctaaa     180
gaatatcttc attgggatgc tccatataca aaagttcaat caggttcact taacaatggt     240
gatgttgctt ggtttcttaa tggtaaactt aacgcttcat ataattgtgt tgatcgacat     300
gcttttgcta atccagataa accagctctt atctatgaag ctgatgatga atcagataac     360
aaaatcatca catttggtga acttttgcga aaagtttcac aaattgctgg tgttcttaaa     420
tcatggggtg ttaaaaaagg tgatacagtt gctatctatc ttccaatgat tcctgaagct     480
gttattgcta tgcttgctgt tgctcgaatt ggtgctattc attcagttgt ttttgctggt     540
ttttcagctg gttcacttaa agatcgagtt gttgatgcta attcaaaagt tgttatcaca     600
tgtgatgaag taaacgagg tggtaaaaca attaacacga aaaaaatcgt tgatgaaggt     660
cttaatggtg ttgatcttgt ttcacgtatt cttgtttttc aacgaacagg tactgaaggt     720
attccaatga aagctggtcg agattattgg tggcatgaag aagctgctaa caacgaaca     780
tatcttccac cagtttcatg tgatgctgaa gatccacttt ttcttttgta tacatctggt     840
tcaacaggtt ctccaaaagg tgttgttcat acaacaggtg ttatcttct ggtgctgct      900
cttacaacac gatatgtctt tgatattcat ccagaagatg ttctttttac agcaggtgat     960
gttggttgga ttacaggtca tacttatgca ctttatggtc cacttacact tggtacagct    1020
tcaattatct ttgaatcaac gccagcttat ccagattatg gtcgatattg gcgaattatt    1080
caacgacata aagctacaca tttttatgtc gctccaacag cacttcgact tattaaacga    1140
gttggtgaag ctgaaattgc aaaatatgat acatcatcac ttcgagttct ggttcagtt     1200
ggtgaaccaa tttcaccaga tctttgggaa tggtatcatg aaaaagttgg taacaaaat     1260
tgtgttatct gtgatacaat gtggcaaaca gaatcaggtt ctcatcttat tgctccactt    1320
gctggtgctg ttccaacaaa accaggttca gctacagttc cattttttgg tatcaatgct    1380
tgtattattg atccagttac aggtgttgaa cttgaaggta atgatgttga aggtgttctt    1440
gctgttaaat caccatggcc atcaatggct cgatcagttt ggaatcatca tgatcgttat    1500
atggatacgt atcttaaacc atatccaggt cactatttta caggtgatgg tgcaggtcga    1560
gatcatgatg ttattattg gattcgaggt cgagttgatg atgttgttaa tgtttcaggt    1620
catcgacttt caacatcaga aattgaagca tcaattcaa accatgaaaa tgtttcagaa    1680
gctgctgttg ttggtattcc agatgaactt acaggtcaaa cagttgttgc ttatgtctct    1740
cttaaagatg gttatcttca aaacaatgct actgaaggtg atgctgaaca tattaccca     1800
gataatcttc gacgagaact tattcttcaa gttcgaggtg aaattggtcc atttgcttca    1860
ccaaaaacaa ttattcttgt tcgagatctt ccacgaacac gatcaggtaa atcatgcga    1920
cgagttcttc gaaaagttgc ttcaaatgaa gctgaacaac ttggtgatct tacaacactt    1980
gcaaatccag aagttgttcc agctattatt tcagctgtcg aaaaccagtt tttctcacag    2040
aaaaagaagt aa                                                         2052
```

<210> SEQ ID NO 93
<211> LENGTH: 1836
<212> TYPE: DNA
<213> ORGANISM: Artificial Sequence
<220> FEATURE:
<223> OTHER INFORMATION: Rhizopus oryzae codon optimized to Rhizopus oryzae

<400> SEQUENCE: 93

```
atgtcaaaac ttcgacgacg aaaacaagaa aaacaacga  aaacaaacga tcaagaactt      60
cctgaagata ttatggctga ttcagctgct aatgtcttta aagagaaacg accattttgg     120
ggtcgaaaac gatttaactt tatcgttggt ctttcagttg gtcttttggc aatgtatgct     180
gcttcaacaa caccagttgc tcaatcacat attaactcac ttcagcacta tcttttgctt     240
caacttgctg atattgatct tgcttcaatt cttccagcta cagaaatggt tgatgaattt     300
cttggtaact ttacaaatct tatcacacca acaccagcaa cagaaatgtc atttatgcca     360
gctcttgaat ataaagagtc acttgatctt aaaccacaat ttccagttgt tatgattcca     420
gctatggttc gatcagttct tcttgataaa gaatcatgga cagaacatat tatgcttgat     480
ccagaaacag gtcttgatcc accaggttat aaagttcgag ctgtccatga aaaaaaaggt     540
gttgaagctg ctgattattt cattacaggt tattgggttt gggctaaagt tattgaaaat     600
cttgctacga ttggttatga tacgaacaac atgtattttg cttcatatga ttggcgactt     660
tcattttcaa atcttgaagt ccgagatggt tattttttcaa aacttaaaca cacgatcgag     720
ctttcaaaaa aacaatcagg tcagaaatca gtcattatca cacattcaat gggtggtaca     780
atgttccat atttcttaa atgggtcgaa tcaaaaggtc atggtcaagg tggtcaaaaa     840
tgggttgatg aacatattga atcatttgtc aatattgctg ctccacttgt tggtgttcca     900
aaagctgtta catcacttct ttcaggtgaa acacgagata caatggctct tggttcattt     960
ggtgcttatg tccttgagaa attcttttca cgacgagaac gagctaaact tatgcgatca    1020
tggatgggtg gtgcatcaat gcttccaaaa ggtggtgaag caatttgggg tcgaggtggt    1080
aatgctccag atgatgaaga agatgagaaa tatcagtcat ttggtaacat gatttcattt    1140
gttccacgac cagaaggttt taacgaaaat tcaacggata ttccatcaaa ttcaggtgat    1200
ccacttgttc gaattatac agtccaaggt tcaattcaac ttcttacgaa aaacgctgat    1260
atcaaatttg gtaaacagct ttatgctaac tattcatttg gtcttacaac atcatcaaaa    1320
cagcttaaac gaaatgaaaa cgatccaaca aaatggtcaa atccacttga atcacgactt    1380
ccaaatgctc caaacatgaa aatctattgt ttttatggta ttgaagttcc aacagagcga    1440
tcatattatt atgctatcct taacgaaaat atggatcaag aatgtggtca ttcaaattca    1500
acagctgaat gtacaacaga acaaaatgct gaaccaaatt catcaccagc tgttgctaaa    1560
acatcatcag ctgcttttcc agataaaaca ccatcacttc atattgatgc ttcaattaat    1620
gatccagtcc aacgaattga aacaggtatt cgatttcaa atggtgatgg tacagttcca    1680
cttcttttcac ttggttatat gtgtgctcca tcaggtggtt ggcgaaaaca tgctgatttg    1740
tataatccag gtcattcacc agttgttctt cgagaatata acatgaagt ctcaacgtca    1800
aaacttgatg ttcgaggtgg ttggatttca tattaa                              1836
```

<210> SEQ ID NO 94
<211> LENGTH: 1701
<212> TYPE: DNA
<213> ORGANISM: Saccharomyces cerevisiae

<400> SEQUENCE: 94

```
atgtctgaaa ttactttggg taaatatttg ttcgaaagat taaagcaagt caacgttaac      60
accgttttcg gtttgccagg tgacttcaac ttgtccttgt tggacaagat ctacgaagtt     120
gaaggtatga gatgggctgg taacgccaac gaattgaacg ctcgttacgc cgctgatggt     180
tacgctcgta tcaagggtat gtcttgtatc atcaccacct tcggtgtcgg tgaattgtct     240
gctttgaacg gtattgccgg ttcttacgct gaacacgtcg gtgttttgca cgttgttggt     300
gtcccatcca tctcttctca agctaagcaa ttgttgttgc accacacctt gggtaacggt     360
gacttcactg ttttccacag aatgtctgcc aacatttctg aaaccactgc tatgatcact     420
gacatctgta ccgccccagc tgaaattgac agatgtatca gaaccactta cgtcacccaa     480
agaccagtct acttaggttt gccagctaac ttggtcgact gaacgtccc agctaagttg     540
ttgcaaactc caattgacat gtctttgaag ccaaacgatg ctgaatccga aaaggaagtc     600
attgacacca tcttggtctt ggctaaggat gctaagaacc cagttatctt ggctgatgct     660
tgttgttcca gacacgacgt caaggctgaa actaagaagt tgattgactt gactcaattc     720
ccagctttcg tcaccccaat gggtaagggt tccattagcg aacaacaccc aagatacggt     780
ggtgtttacg tcggtacctt gtccaagcca gaagttaagg aagccgttga atctgctgac     840
ttgatttttgt ctgtcggtgc tttgttgtct gatttcaaca ccggttcttt ctcttactct     900
tacaagacca gaacattgt cgaattccac tccgaccaca tgaagatcag aaacgccact     960
ttcccaggtg tccaaatgaa attcgttttg caaaagttgt tgaccaatat tgctgacgcc    1020
gctaagggtt acaagccagt tgctgtccca gctagaactc cagctaacgc tgctgtccca    1080
gcttctaccc cattgaagca agaatggatg tggaaccaat tgggtaactt cttgcaagaa    1140
ggtgatgttg tcattgctga accggtacc tccgctttcg gtatcaacca aaccactttc    1200
ccaaacaaca cctacggtat ctctcaagtc ttatggggtt ccattggttt caccactggt    1260
gctaccttgg gtgctgcttt cgctgctgaa gaaattgatc aaagaagag agttatctta    1320
ttcattggtg acggttcttt gcaattgact gttcaagaaa tctccaccat gatcagatgg    1380
ggcttgaagc atacttgtt cgtcttgaac aacgatggtt acaccattga aaagttgatt    1440
cacggtccaa aggctcaata caacgaaatt caaggttggg accacctatc cttgttgcca    1500
actttcggtg ctaaggacta cgaaacccac agagtcgcta ccaccggtga atgggacaag    1560
ttgacccaag acaagtcttt caacgacaac tctaagatca gaatgattga ggttatgttg    1620
ccagtcttcg atgctccaca aaacttggtt gaacaagcta agttgactgc tgctaccaac    1680
gctaagcaat aagcgattta a                                              1701
```

<210> SEQ ID NO 95
<211> LENGTH: 563
<212> TYPE: PRT
<213> ORGANISM: Saccharomyces cerevisiae

<400> SEQUENCE: 95

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Arg Tyr Ala Ala Asp Gly Tyr Ala Arg Ile
    50                  55                  60

-continued

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
            85                  90                  95

His Val Gly Val Pro Ser Ile Ser Ser Gln Ala Lys Gln Leu Leu
    100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Cys Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
                180                 185                 190

Asp Ala Glu Ser Glu Lys Glu Val Ile Asp Thr Ile Leu Val Leu Ala
        195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Ser Glu Gln His
                245                 250                 255

Pro Arg Tyr Gly Gly Val Tyr Val Gly Thr Leu Ser Lys Pro Glu Val
                260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Asn
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
            355                 360                 365

Trp Met Trp Asn Gln Leu Gly Asn Phe Leu Gln Glu Gly Asp Val Val
370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

```
His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
        500                 505                 510

Ala Thr Thr Gly Glu Trp Asp Lys Leu Thr Gln Asp Lys Ser Phe Asn
            515                 520                 525

Asp Asn Ser Lys Ile Arg Met Ile Glu Val Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 96
<211> LENGTH: 1692
<212> TYPE: DNA
<213> ORGANISM: Saccharomyces cerevisiae

<400> SEQUENCE: 96
atgtcggaga tcaccctcgg caagtacctc ttcgagcgcc tcaagcaggt caacgtcaac      60
accgtctttg gcctcccggg cgacttcaac ctctcgctcc tcgacaagat ctacgaggtc     120
gagggcatgc gctgggccgg caacgccaac gaactcaacg ccgcctacgc cgccgacggc     180
tacgcccgca tcaagggcat gtcgtgcatc atcaccacct tcggtgtcgg cgaactctcg     240
gccctcaacg gtatcgccgg ctcgtacgct gagcacgtcg gcgtcctcca cgtcgtcggc     300
gtcccttcga tctcggccca ggccaagcag ctcctcctcc accacccct cggtaacggc     360 gacttcaccg tctttcaccg catgtcggcc aacatctcgg aaaccaccgc catgatcacc     420
gatatcgcca ccgccctgc cgagatcgac cgctgcatcc gcaccaccta cgtcacccag     480
cgccccgtct acctcggcct ccccgccaac ctcgtcgacc tcaacgtccc cgccaagctc     540
ctccagaccc ccatcgacat gtcgctcaag cccaacgacg ccgagtcgga gaaggaagtc     600
atcgacacca tcctcgccct cgtcaaggac gccaagaacc ccgtcatcct cgccgacgcc     660
tgctgctcgc gccacgacgt caaggccgaa acgaagaagc tcatcgatct cacccagttc     720
cccgccttcg tcacccccat gggcaagggc tcgatcgacg agcagcaccc ccgctacggc     780
ggcgtctacg tcggcaccct ctcgaagccc gaggtcaagg aagccgtcga gtcggccgac     840
ctcatcctct cggtcggcgc actcctctcg gacttcaaca ccggctcgtt ctcgtactcg     900
tacaagacca gaacatcgt cgagttccac tcggaccaca tgaagatccg caacgccacc     960
ttccccggcg tccagatgaa gttcgtcctc cagaagctcc tcaccacgat cgccgacgcc    1020
gccaagggct acaagcccgt cgccgtccct gcccgcacac cagccaacgc agccgtccct    1080
gcctcgaccc ccctcaagca agagtggatg tggaaccagc tcggcaactt cctccaagag    1140
ggcgacgtcg tgatcgccga aaccggcacc tcggccttcg gcatcaacca gaccaccttc    1200
cccaacaaca cctacggcat ctcgcaggtc tctgggggct cgatcggctt caccaccggc    1260
gccaccctcg gcgctgcctt cgcagctgag gaaatcgacc caagaagcg tgtcatcctc    1320 ttcatcggcg acggctcgct ccagctcacc gtccaagaga tctcgaccat gatccgctgg    1380
ggcctcaagc cctacctctt cgtcctcaac aacgacggct acaccatcga aagctcatc    1440 cacggcccca ggcccagta caacgagatc cagggctggg accacctctc gctcctccct    1500
accttcggcg ccaaggacta cgaaacccac cgcgtcgcca aaccggcga gtgggacaag    1560 ctcacccagg acaagtcgtt caacgacaac tcgaagatcc gcatgatcga gatcatgctc    1620
```

-continued

```
cccgtctttg acgcccccca gaacctcgtc gagcaggcca agctcaccgc cgccaccaac    1680
gccaagcagt ga                                                        1692

<210> SEQ ID NO 97
<211> LENGTH: 1692
<212> TYPE: DNA
<213> ORGANISM: Saccharomyces cerevisiae

<400> SEQUENCE: 97
atgtcagaaa tcacgcttgg taaatatctt ttcgagcgac ttaaacaggt caatgtcaat      60
actgtctttg gtttgccagg tgatttcaac ctttcacttc ttgacaagat ctatgaagtc     120
gaaggtatgc gttgggcagg taatgcaaat gaacttaatg cagcatatgc agcagatggt     180
tatgcacgaa tcaaaggtat gtcatgtatc atcacaacgt ttggtgtcgg tgaactttca     240
gcacttaatg gtattgcagg ttcatatgca gaacatgttg gtgttcttca tgttgttggt     300
gttccatcaa tttcagctca agcaaaacag cttcttcttc atcatacact tggtaacggt     360
gattttacgg tctttcatcg aatgtcagca acatctcag aaacaacagc aatgatcaca     420
gatattgcaa cagcaccagc agaaattgat cgatgtatcc gaacaacata tgtcacacaa     480
cgaccagttt atttgggttt gccagcaaat cttgtcgatc ttaatgtccc agcaaaactt     540
cttcagacac caattgacat gtcacttaaa cctaacgatg ccgaatcaga aaagaagtc      600 atcgataaca tccttgcact tgtcaaagat gcaaaaaacc cagttatcct tgcagatgca     660
tgttgttcac gacatgatgt caaagcagaa acgaagaaac ttatcgatct tacacagttt     720
ccagcatttg ttacgccaat gggtaaaggt tcaatcgatg aacaacatcc acgatatggt     780
ggtgtttatg ttggtacact ttcaaaacca gaggtcaaag aagcagttga atcagcagat     840
cttatccttt cagttggtgc acttctttca gattttaaca cgggttcatt ctcatattct     900
tataagacga agaacatcgt cgagtttcac tcagatcata tgaagatccg aaacgcaaca     960
tttccaggtg tccaaatgaa gtttgtcctt cagaaacttc ttacgacaat gcagatgca     1020 gccaaaggtt ataagccagt tgcagttcca gcacgaacac cagcaaatgc agcagttcca    1080
gcttcaacac cacttaaaca agaatggatg tggaatcagc ttggtaactt tcttcaagag    1140
ggtgatgttg ttatcgcaga aacaggtaca tcagcatttg gtatcaacca gacaacgttt    1200
ccaaacaaca cgtatggtat ctcacaagtt ctttggggtt caatcggttt tacaacaggt    1260
gcaacacttg gtgcagcatt tgctgcagaa gaaatcgatc caaaaaagcg agtcatcctt    1320
tttatcggtg atggttcact tcagcttaca gttcaagaaa tctctacaat gatccgatgg    1380
ggtcttaagc catatctttt tgtccttaac aacgacggtt atacgatcga aaaacttatc    1440
catggtccaa aggcacagta taacgaaatt caaggttggg atcacctttc acttttgcca    1500
acatttggtg caaaggatta tgagacacat cgagttgcaa caacaggtga atgggacaaa    1560
cttacacagg ataagtcatt caacgacaac tcaaagatcc gaatgatcga aattatgctt    1620
ccagtctttg atgcaccaca aaatcttgtt gagcaggcaa aacttacagc agcaacaaat    1680
gccaaacagt aa                                                        1692
```